(12) United States Patent
Yun et al.

(10) Patent No.: US 11,850,215 B2
(45) Date of Patent: Dec. 26, 2023

(54) RECOMBINANT ADENOVIRUSES AND STEM CELLS COMPRISING SAME

(71) Applicant: GENEMEDICINE CO., LTD., Seoul (KR)

(72) Inventors: Chae Ok Yun, Seoul (KR); Yan Li, Seoul (KR)

(73) Assignee: GENEMEDICINE CO., LTD., Seongdong-gu seoul (KR)

( * ) Notice: Subject to any disclaimer, the term of this patent is extended or adjusted under 35 U.S.C. 154(b) by 406 days.

(21) Appl. No.: 16/772,033

(22) PCT Filed: Dec. 12, 2018

(86) PCT No.: PCT/KR2018/015800
§ 371 (c)(1),
(2) Date: Jun. 11, 2020

(87) PCT Pub. No.: WO2019/117632
PCT Pub. Date: Jun. 20, 2019

(65) Prior Publication Data
US 2021/0069253 A1    Mar. 11, 2021

(30) Foreign Application Priority Data
Dec. 13, 2017    (KR) .......................... 10-2017-0171539

(51) Int. Cl.
| | |
|---|---|
| *A61K 35/28* | (2015.01) |
| *A61P 35/00* | (2006.01) |
| *C12N 7/00* | (2006.01) |
| *C12N 15/86* | (2006.01) |
| *C12N 5/0775* | (2010.01) |

(52) U.S. Cl.
CPC .............. *A61K 35/28* (2013.01); *A61P 35/00* (2018.01); *C12N 5/0663* (2013.01); *C12N 7/00* (2013.01); *C12N 15/86* (2013.01); *C12N 2710/10322* (2013.01); *C12N 2710/10332* (2013.01); *C12N 2710/10343* (2013.01); *C12N 2710/10345* (2013.01); *C12N 2830/008* (2013.01)

(58) Field of Classification Search
CPC combination set(s) only.
See application file for complete search history.

(56) References Cited

U.S. PATENT DOCUMENTS

| | | | |
|---|---|---|---|
| 9,689,000 B2 | 6/2017 | Yun et al. | |
| 2006/0062764 A1 | 3/2006 | Police et al. | |
| 2007/0010016 A1* | 1/2007 | McCelland ............ | C12N 15/86 435/235.1 |
| 2010/0047208 A1 | 2/2010 | Ke | |
| 2013/0323206 A1 | 12/2013 | Yun et al. | |
| 2014/0199688 A1 | 7/2014 | Mizuguchi et al. | |

FOREIGN PATENT DOCUMENTS

| | | |
|---|---|---|
| CN | 101068933 A | 11/2007 |
| JP | 2020532737 A | 11/2020 |
| KR | 10-2012-0036688 A | 4/2012 |
| KR | 10-2012-0099317 A | 9/2012 |
| KR | 10-2014-0049593 A | 4/2014 |
| KR | 10-2015-0136818 A | 12/2015 |

OTHER PUBLICATIONS

Knaän-Shanzer, Shoshan, et al. "Endowing human adenovirus serotype 5 vectors with fiber domains of species B greatly enhances gene transfer into human mesenchymal stem cells." Stem Cells 23.10 : 1598-1607. (Year: 2005).*
Suzuki, Takeo, et al. "Mesenchymal stem cells are efficiently transduced with adenoviruses bearing type 35-derived fibers and the transduced cells with the IL-28A gene produces cytotoxicity to lung carcinoma cells co-cultured." BMC cancer 14.1: 1-10. (Year: 2014).*
Int'l Search Report and Written Opinion dated Mar. 18, 2019 in Int'l Application No. PCT/KR2018/015800, English translation of Search Report only.
Suzuki et al, "Mesenchymal stem cells are efficiently transduced with adenoviruses bearing type 35-derived fibers and the transduced cells with the IL-28A gene produces cytotoxicity to lung carcinoma cells co-cultured," BMC Central, vol. 14, No. 713, pp. 1-10 (2014).
Jang et al, "Effect of Function-Enhanced Mesenchymal Stem Cells Infected With Decorin-Expressing Adenovirus on Hepatic Fibrosis," Stem Cells Translational Medicine, vol. 5, pp. 1247-1256 (Jun. 30, 2016).
Kim et al, "Enhanced antitumor immunotherapeutic effect of B-cell-based vaccine transduced with modified adenoviral vector containing type 35 fiber structures," Gene Therapy, vol. 21, pp. 106-114 (2014).
Office Action dated Nov. 22, 2019 in KR Application No. 10-2018-0160424.
Hai et al., "Application of mesenchymal stem cells as a vehicle to deliver replication-competent adenovirus for treating malignant glioma", Chinese Journal of Cancer, vol. 31, Issue 5, pp. 233-240, 2012.

(Continued)

*Primary Examiner* — Marcia S Noble
*Assistant Examiner* — Josephine M Gonzales
(74) *Attorney, Agent, or Firm* — Panitch Schwarze Belisario & Nadel LLP; Stephany G. Small

(57) ABSTRACT

The present invention relates to: recombinant adenoviruses, which have an excellent ability to be introduced into stem cells and can be easily introduced into stem cells even at a low concentration; stem cells comprising the same; a gene delivery composition; and a pharmaceutical composition. Stem cells into which adenoviruses are introduced, of the present invention, have excellent in vivo survivability and a treatment effect on tumor cells, and, when used as an anticancer drug, do not cause problems with respect to in vivo survival, hepatotoxicity and the like of stem cells so as to be particularly usable for systemic administration, and have an excellent anticancer effect even in small doses, thereby being widely usable as an anticancer drug using adenoviruses.

8 Claims, 39 Drawing Sheets

Specification includes a Sequence Listing.

(56) References Cited

OTHER PUBLICATIONS

Li et al., "Mesenchymal stem cells as delivery vectors for anti-tumor therapy" Stem Cell Investigation, 2:6, 2015.
Tagawa Masatoshi, "Mesenchymal stem cells infected with modified adenoviruses as carrier cells that target human gastrointestinal tumors", Cancer Gene Therapy, 249, 5 pages, 2010 (English Abstract Only).
Office Action dated Jan. 4, 2023, in corresponding Chinese Patent Application No. 2018800811421.

* cited by examiner

1: dE1/LacZ
2: dE1-K35/LacZ
3: dE1-RGD/LacZ

X-gal stained at 2 days after viral infection

MSC: 1x10⁶ cells/mouse
Ad : 5MOI(5x10⁸ VP)
Ad-MSC: (Ha2bm-d19-k35/sLRP6, 5 MOI)
IV injection 1. PBS
2. MSC
3. HCC-oAd-WNTi (naked Ad)
4. HCC-oAd-WNTi/MSC (Ad-MSC)

1. PBS
2. MSC
3. HCC-oAd-WNTi (naked Ad)
4. HCC-oAd-WNTi/MSC (Ad-MSC)

1. untreated  2. MSC  3. HCC-oAd-WNTi  4. HCC-oAd-WNTi/MSC

SEQUENCE LISTING

<160> NUMBER OF SEQ ID NOS: 9

<210> SEQ ID NO 1
<211> LENGTH: 570
<212> TYPE: DNA
<213> ORGANISM: Artificial
<220> FEATURE:
<223> OTHER INFORMATION: K35 Fiber

<400> SEQUENCE: 1

```
tggaccggaa taaaccctcc acctaactgt caaattgtgg aaaacactaa tacaaatgat      60
ggcaaactta ctttagtatt agtaaaaaat ggagggcttg ttaatggcta cgtgtctcta     120
gttggtgtat cagacactgt gaaccaaatg ttcacacaaa agacagcaaa catccaatta     180
agattatatt ttgactcttc tggaaatcta ttaactgagg aatcagactt aaaaattcca     240
cttaaaaata aatcttctac agcgaccagt gaaactgtag ccagcagcaa agcctttatg     300
ccaagtacta cagcttatcc cttcaacacc actactaggg atagtgaaaa ctacattcat     360
ggaatatgtt actacatgac cagttatgat agaagtctat ttcccttgaa catttctata     420
atgctaaaca gccgtatgat ttcttccaat gttgcctatg ccatacaatt tgaatggaat     480
ctaaatgcaa gtgaatctcc agaaagcaac atagctacgc tgaccacatc cccctttttc     540
ttttcttaca ttacagaaga cgacgaataa                                      570
```

<210> SEQ ID NO 2
<211> LENGTH: 302
<212> TYPE: DNA
<213> ORGANISM: Artificial
<220> FEATURE:
<223> OTHER INFORMATION: HRE domain comprising 6copy of HRE

<400> SEQUENCE: 2

```
acgcgttatc gataccgtct acctcgagcc acagtgcata cgtgggctcc aacaggtcct    60
cttgtcgagc cacagtgcat acgtgggctc caacaggtcc tcttgtcgag ccacagtgca   120
tacgtgggct ccaacaggtc ctcttgtcga gccacagtgc atacgtgggc tccaacaggt   180
cctcttgtcg agccacagtg catacgtggg ctccaacagg tcctcttgtc gagccacagt   240
gcatacgtgg gctccaacag gtcctcttgt cgacgggggg cccgctacca cgcgttatcg   300
at                                                                  302

<210> SEQ ID NO 3
<211> LENGTH: 367
<212> TYPE: DNA
<213> ORGANISM: Artificial
<220> FEATURE:
<223> OTHER INFORMATION: Enhancer A

<400> SEQUENCE: 3
cagattgaat tatttgcctg tcatacagct aataattgac cataagacaa ttagatttaa    60
attagttttg aatctttcta ataccaaagt tcagtttact gttccatgtt gcttctgagt   120
ggcttcacag acttatgaaa aagtaaacgg aatcagaatt acatcaatgc aaaagcattg   180
ctgtgtgaac tctgtactta ggactaaact ttgagcaata acacacatag attgaggatt   240
gtttgctgtt agcatacaaa ctctggttca aagctcctct ttattgcttg tcttggaaaa   300
tttgctgttc ttcatggttt ctcttttcac tgctatctat ttttctcaac cactcacatg   360
gctacaa                                                             367

<210> SEQ ID NO 4
<211> LENGTH: 193
<212> TYPE: DNA
<213> ORGANISM: Artificial
<220> FEATURE:
<223> OTHER INFORMATION: Enhancer B

<400> SEQUENCE: 4
cctgattaat aattcacta agtcaatagg catagagcca ggactgtttg ggtaaactgg     60
tcactttatc ttaaactaaa tatatccaaa actgaacatg tacttagtta ctaagtcttt   120
gactttatct cattcatacc actcagcttt atccaggcca cttatttgac agtattattg   180
cgaaaacttc cta                                                      193

<210> SEQ ID NO 5
<211> LENGTH: 301
<212> TYPE: DNA
<213> ORGANISM: Artificial
<220> FEATURE:
<223> OTHER INFORMATION: AFP promoter

<400> SEQUENCE: 5
tctctttgaa agatctgtag tttgaggaga atatttgtta tatttgcaaa ataaaataag    60
tttgcaagtt tttttttttct gccccaaaga gctctgtgtc cttgaacata aaatacaaat  120
aaccgctatg ctgttaatta ttggcaaatg tcccattttc aacctaagga aataccaaaa   180
gtaacagata taccaacaaa aggttactag ttaacaggca ttgcctgaaa agagtataaa   240
agaatttcag catgattttc catattgtgc ttccaccact gccaataaca taagcttact   300
g                                                                   301

<210> SEQ ID NO 6
```

```
<211> LENGTH: 41
<212> TYPE: DNA
<213> ORGANISM: Artificial
<220> FEATURE:
<223> OTHER INFORMATION: HRE(hypoxia-response elements) domain

<400> SEQUENCE: 6
ccacagtgca tacgtgggct ccaacaggtc ctcttgtcga g                           41

<210> SEQ ID NO 7
<211> LENGTH: 176
<212> TYPE: DNA
<213> ORGANISM: Artificial
<220> FEATURE:
<223> OTHER INFORMATION: 5myc

<400> SEQUENCE: 7
gtcgacggta tcgatgtcga gggatctctc cgctggggcc ctcgctggcg tccctgcacc        60
ctgggagcgc gagcggcgcg cgggcgggga agcgcggccc agaccccggg gtccgcccgg       120
agcagctgac cacgtggtac cacgtggtac cacgtggtac cacgtggtac cacgtg          176

<210> SEQ ID NO 8
<211> LENGTH: 772
<212> TYPE: DNA
<213> ORGANISM: Artificial
<220> FEATURE:
<223> OTHER INFORMATION: mTERT

<400> SEQUENCE: 8
gtctgcgctg tcggggccag gccgggctcc cagtggattc gcgggcacag acgcccagga        60
ccgcgcttcc cacgtggcgg agggactggg gacccgggca ccgtcctgc cccttcacct       120 tccagctccg cctcctccgc gcggaccccg ccccgtcccg accctcccg ggtcccggc        180 ccagccccct ccgggccctc ccagccctc cccttccttt ccgcggcccc gccctctcct       240
cgcggcgcga gtttcaggca gcgctgcgtc ctgctgcgca cgtgggaagc cctggccccg       300 ggcaccccg cgaagcttag gccgattcga gatctctccg ctggggccct cgctggcgtc       360
cctgcaccct gggagcgcga gcggcgcgcg gcggggaag cgcggcccag accccgggt       420 ccgcccggag cagctgcgct gtcggggcca ggccgggctc ccagtggatt cgcgggcaca       480
gacgcccagg accgcgctcc ccacgtggcg gagggactgg ggacccgggc accgtcctg       540 ccccttcacc ttccagctcc gcctcctccg cgcggacccc gccccgtccc gacccctccc       600
gggtccccgg cccagccccc tccgggccct ccagcccct ccccttcctt tccgcggccc       660
cgccctctcc tcgcggcgcg agtttcaggc agcgctgcgt cctgctgcgc acgtgggaag       720
ccctggcccc gggcaccccc gcgaagcttc gaatcgcgaa ttcgccctcg ag              772

<210> SEQ ID NO 9
<211> LENGTH: 2687
<212> TYPE: DNA
<213> ORGANISM: Artificial
<220> FEATURE:
<223> OTHER INFORMATION: Rd19 Sequence

<400> SEQUENCE: 9
atgagacata ttatctgcca cggaggtgtt attaccgaag aaatggccgc cagtcttttg        60
gaccagctga tcgaagaggt actggctgat aatcttccac ctcctagcca ttttgaacca       120
cctaccctcc acggactgta tgatttagac gtgacggccc ccgaagatcc caacgaggag       180
gcggtttcgc agattttttcc cgactctgta atgttggcgg tgcaggaagg gattgactta       240
```

-continued

```
ctcactttc cgccggcgcc cggttctccg gagccgcctc acctttcccg gcagcccgag      300
cagccggagc agagagcctt gggtccggtt tctatgccaa accttgtacc ggaggtgatc      360
ggtggtggcg gaggcggggg tggctttcca cccagtgacg acgaggatga agagggtgag      420
gagtttgtgt tagattatgt ggagcacccc gggcacggtt gcaggtcttg tcattatcac      480
cggaggaata cggggaccc agatattatg tgttcgcttt gctatatgag gacctgtggc       540
atgtttgtct acagtaagtg aaaattatgg gcagtgggtg atagagtggt gggtttggtg      600
tggtaatttt tttttaatt tttacagttt tgtggtttaa agaattttgt attgtgattt       660
ttttaaaagg tcctgtgtct gaacctgagc ctgagcccga ccagaaccg gagcctgcaa       720 gacctacccg ccgtcctaaa atggcgcctg ctatcctgag acgcccgaca tcacctgtgt      780
ctagagaatg caatagtagt acggatagct gtgactccgg tccttctaac acacctcctg      840
agatacaccc ggtggtcccg ctgtgcccca ttaaaccagt tgccgtgaga gttggtgggc      900
gtcgccaggc tgtggaatgt atcgaggact tgcttaacga gcctgggcaa cctttggact      960
tgagctgtaa acgccccagg ccataaggtg taaacctgtg attgcgtgtg tggttaacgc     1020
ctttgtttgc tgaatgagtt gatgtaagtt taataaaggg tgagataatg tttaacttgc     1080
atggcgtgtt aaatgggcg gggcttaaag ggtatataat gcgccgtggg ctaatcttgg      1140
ttacatctga cctcctgtag gctagctgtt gcttttttga gttttataaa ggataaatgg     1200
agcgaagaaa cccatctgag cgggggtac ctgctggatt ttctggccat gcatctgtgg      1260
agagcggttg tgagacacaa gaatcgcctg ctactgttgt cttccgtccg cccggcgata     1320
ataccgacgg aggagcagca gcagcagcag gaggaagcca ggcggcggcg gcaggagcag     1380
agcccatgga acccgagagc cggcctggac cctcgggaat gaatgttgta caggtggctg     1440
aactgtatcc agaactgaga cgcatttga caattacaga ggatgggcag gggctaaagg     1500
gggtaaagag ggagcggggg gcttgtgagg ctacagagga ggctaggaat ctagctttta     1560
gcttaatgac cagacaccgt cctgagtgta ttacttttca acagatcaag gataattgcg     1620
ctaatgagct tgatctgctg gcgcagaagt attccataga gcagctgacc acttactggc     1680
tgcagccagg ggatgatttt gaggaggcta ttagggtata tgcaaaggtg gcacttaggc     1740
cagattgcaa gtacaagatc agcaaacttg taaatatcag gaattgttgc tacatttctg     1800
ggaacggggc cgaggtggag atagatacgg aggataggt ggcctttaga tgtagcatga     1860
taaatatgtg gccggggtg cttggcatgg acggggtggt tattatgaat gtaaggttta     1920
ctggccccaa ttttagcggt acggttttcc tggccaatac caaccttatc ctacacggtg     1980
taagcttcta tgggtttaac aatacctgtg tggaagcctg gaccgatgta agggttcggg     2040
gctgtgcctt ttactgctgc tggaaggggg tggtgtgtcg ccccaaaagc agggcttcaa      2100
ttaagaaatg cctctttgaa aggtgtacct tgggtatcct gtctgagggt aactccaggg     2160
tgcgccacaa tgtggcctcc gactgtggtt gcttcatgct agtgaaaagc gtggctgtga     2220
ttaagcataa catggtatgt ggcaactgcg aggacagggc ctctcagatg ctgacctgct     2280
cggacggcaa ctgtcacctg ctgaagacca ttcacgtagc cagccactct cgcaaggcct     2340
ggccagtgtt tgagcataac atactgaccc gctgttcctt gcatttgggt aacaggaggg     2400
gggtgttcct accttaccaa tgcaatttga gtcacactaa gatattgctt gagcccgaga     2460
```

-continued

| | | | | | |
|---|---|---|---|---|---|
| gcatgtccaa | ggtgaacctg | aacgggtgt | ttgacatgac | catgaagatc | tggaaggtgc | 2520 |
| tgaggtacga | tgagacccgc | accaggtgca | gaccctgcga | gtgtggcggt | aaacatatta | 2580 |
| ggaaccagcc | tgtgatgctg | gatgtgaccg | aggagctgag | gcccgatcac | ttggtgctgg | 2640 |
| cctgcacccg | cgctgagttt | ggctctagcg | atgaagatac | agattga | | 2687 |

RECOMBINANT ADENOVIRUSES AND STEM CELLS COMPRISING SAME

TECHNICAL FIELD

The present invention relates to a recombinant adenovirus having an excellent ability to regulate the expression of cancer-specific genes and to be introduced into stem cells, a stem cell into which the recombinant adenovirus is introduced, and gene delivery and cancer-specific therapeutic agent using the same.

BACKGROUND ART

As numerous advantages of adenoviruses as a gene delivery vector have been highlighted, the frequency of use of adenoviruses in cancer gene therapy continues to increase. When cancer is treated with gene therapy, there is an advantage that the long-term and continuous expression of therapeutic genes is not required. In addition, since immune responses of a host, induced by a virus used as a vector, are not very problematic or rather act as an advantage, adenoviruses have been spotlighted as gene carriers for cancer treatment. In particular, cancer cell (tumor)-selective killing adenoviruses (Oncolytic adenovirus), which are capable of proliferating only in cancer cells, do not affect normal cells and can selectively kill only cancer cells, and thus are receiving attention as a next-generation therapeutic agent.

However, when an adenovirus is administered systemically as a gene therapeutic agent, the adenovirus accumulates in liver tissue to induce toxicity, or has a short in-vivo retention time due to a neutralizing antibody produced in the blood, thus reducing the efficiency of delivering the adenovirus to a target tumor site. Therefore, there is an unmet need to develop a gene therapeutic agent that, in gene therapy, maintains the advantages of an adenovirus and exhibits an enhanced ability to target a tumor site and enhanced transduction efficiency.

One of the carriers of a gene therapeutic agent is mesenchymal stem cells (MSCs). MSCs can be easily isolated from various tissues such as bone marrow and are easily cultured and proliferated in vitro. In addition, when administered into the body, MSCs move to a damaged site and replace damaged cells, and secrete various growth factors and cytokines, thereby providing the effects of suppressing disease and promoting the regeneration of the damaged site. In addition, MSCs possess the ability to migrate to tumors due to tumor tropism characteristics thereof, and do not express co-stimulatory molecules, resulting in reduced or no immune rejection responses, and thus can be administered systemically, and MSCs are also advantageous in that both self-treatment and allogeneic therapy for many patients are possible.

Thus, efforts have been actively made to develop various regenerative stem cell therapies using these MSCs, which have no immunogenicity and have the ability to target tumors. As a part of the efforts, attempts have been made to develop a cell/gene therapyusing MSCs and an adenovirus-mediated gene therapeutic agent, but there is a problem in that specific receptor-deficient MSCs are not infected with an adenovirus, and thus, until now, there are difficulties in using MSCs as an adenovirus carrier.

Moreover, there is a continuous need to develop a therapeutic agent that can be used for allogeneic treatment for many patients, rather than autogenous treatment, for the development of the gene therapeutics industry, and to develop a preparation method capable of increasing quality consistency and reducing manufacturing costs.

DESCRIPTION OF EMBODIMENTS

Technical Problem

The inventors of the present invention had continuously researched a method that can address the disadvantages of conventional adenoviruses, which cannot be administered systemically and have low efficiency of introduction into stem cells, and that can deliver, after injected into the body, adenoviruses to a target site with high efficiency, and as a result, developed adenoviruses exhibiting an excellent capacity of being introduced into stem cells even at a low concentration and an excellent ability to regulate the expression of cancer-specific genes, and stem cells into which the adenoviruses are introduced, and confirmed that, when the stem cells were used, systemic administration of an adenovirus was possible, the stem cells did not cause problems such as hepatotoxicity due to an excellent ability thereof to target cancer and had an excellent cancer cell-specific killing effect, thus completing the present invention.

Technical Solution

According to an aspect of the present invention, there is provided a recombinant adenovirus comprising a serotype 35 fiber knob and exhibiting an enhanced ability to be introduced into stem cells.

The serotype 35 fiber knob may consist of a sequence of SEQ ID NO: 1

The recombinant adenovirus may further comprise a gene expression regulatory sequence that regulates the expression of a target gene, and the target gene.

Specifically, the recombinant adenovirus may comprise: a gene expression regulatory sequence comprising, in a 5' to 3' direction, (a) a sequence of 6 copies of a hypoxia-response element (HRE), (b) a sequence of 2 copies of alpha-fetoprotein (AFP) enhancer A, (c) a sequence of one copy of AFP promoter enhancer B, and (d) an AFP promoter sequence; a target gene that is operatively linked to the gene expression regulatory sequence; and a serotype 35 fiber knob sequence.

The present invention also provides a mesenchymal stem cell (MSC) comprising the recombinant adenovirus.

The mesenchymal stem cell may be a mesenchymal stem cell, for treating a cancer, comprising a recombinant adenovirus comprising a target gene and a sequence of SEQ ID NO: 1.

The recombinant adenovirus may further comprise a gene expression regulatory sequence that regulates the expression of the target gene.

The gene expression regulatory sequence may comprise an AFP promoter sequence of SEQ ID NO: 5 or a TERT promoter sequence of SEQ ID NO: 8.

The mesenchymal stem cell may be infected for 50 hours or less with a recombinant adenovirus comprising a target gene and a sequence of SEQ ID NO: 1 at a concentration of greater than 0.01 MOI to less than 100 MOI.

The composition is for systemic administration or local administration.

Advantageous Effects of Invention

A recombinant adenovirus of the present invention has an excellent ability to be introduced into stem cells and to regulate the expression of a specific gene, and thus has a characteristic capable of being introduced into stem cells even at a low concentration. In particular, when the adenovirus of the present invention is used, stem cells are highly transfected therewith even at a low concentration, and thus the proportion of stem cells that die in an adenovirus transduction process is low, resulting in enhanced preparation efficiency of a gene therapeutic agent. In addition, an adenovirus-introduced stem cell of the present invention has further enhanced viability and cancer cell-killing capacity. The adenovirus of the present invention loaded in the stem cell is able to self-proliferate, and thus, when applied to gene therapy, the stem cell can exhibit enhanced therapeutic effects. Further, the injected stem cells do not remain in the body, thus not causing side effects. In addition, an adenovirus-loaded stem cell of the present invention and a composition comprising the same are more suitable for systemic administration compared to other adenovirus therapeutic agents, do not cause hepatotoxicity, can be enable allogeneic therapy due to no occurrence of immune responses, and can reduce therapeutic agent costs.

BRIEF DESCRIPTION OF DRAWINGS

FIGS. 6A to 6D illustrate experimental results of liver cancer cell lines, FIG. 6E illustrates the results of a normal cell line, and FIG. 6F illustrates the results of a lung cancer cell line (A549).

FIGS. 10A, 10B, 10C, 10D, and 10E are graphs showing the results of confirming the killing effects of oncolytic adenoviruses with liver cancer-specific promoters constructed according to an embodiment of the present invention, depending on the type of cell line, wherein FIGS. 10A, 10B, and 10C illustrate HCC-specific killing effects in liver cancer cell lines, and FIGS. 10D and 10E illustrate the presence or absence of killing in a normal cell line and killing effects under a normoxia condition and under a hypoxia condition, respectively.

FIGS. 24A and 24B illustrate the results of comparing gene transduction efficiencies according to adenovirus fiber modification in mesenchymal stem cells in which adenoviruses constructed according to an embodiment of the present invention were loaded, wherein FIG. 24B illustrates efficient induction of the expression of the Luc gene through proliferation of the adenoviruses in mesenchymal stem cells in which adenoviruses constructed according to an embodiment of the present invention were loaded.

FIGS. 38A, 38B, 38C, and 38D illustrate the results of confirming the structure and characteristics of WNTi-expressing HCC-targeting oAd according to an embodiment of the present invention, wherein FIG. 38A illustrates the structure of HCC-oAd-WNTi, FIG. 38B illustrates the results of confirming the expression of a Wnt signaling pathway-related gene, FIG. 38C illustrates the results showing the HCC-killing effect of HCC-oAd-WNTi, and FIG. 38D is a graph showing the HCC-killing potency of HCC-oAd-WNTi under hypoxic and normoxic conditions.

BEST MODE

Figure 1:
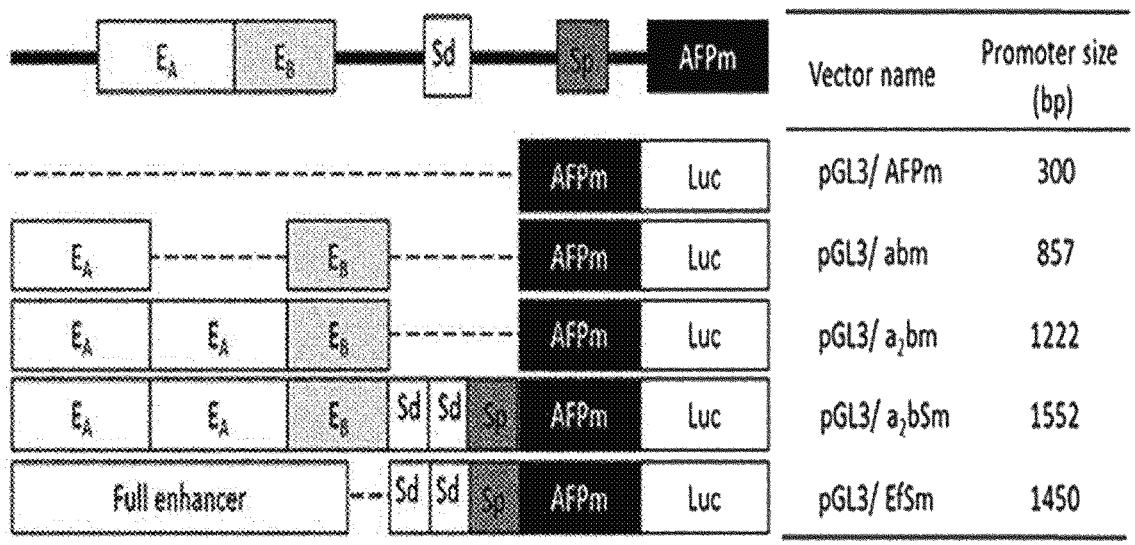
FIG. 1 illustrates the promoter regions and sizes of plasmids in which luciferase expression is regulated by a recombinant AFP promoter produced according to an embodiment of the present invention.

The present invention provides a mesenchymal stem cell with a recombinant adenovirus loaded therein (Ad-MSC), the recombinant adenovirus having an excellent ability to be introduced into a mesenchymal stem cell even at a low concentration due to an excellent ability to deliver a gene into the mesenchymal stem cell, and exhibiting an excellent ability to regulate the expression of the gene, a composition for delivering a gene, comprising the mesenchymal stem cell (Ad-MSC) of the present invention, and a composition for treating cancer comprising the mesenchymal stem cell (Ad-MSC) of the present invention.

Hereinafter, the present invention will be described in more detail.

As the present invention allows for various changes and numerous forms, particular embodiments set forth herein and descriptions are provided only to facilitate the understanding of the present invention, and are not intended to limit the present invention to particular forms of disclosure. The scope of the present invention should be understood as encompassing all changes, equivalents, and substitutes that fall within the technical spirit and scope of the present invention.

According to an embodiment of the present invention, there is provided a recombinant adenovirus comprising a fiber sequence of SEQ ID NO: 1. The present invention also provides a mesenchymal stem cell with the recombinant adenovirus introduced thereinto (Ad-MSC).

Adenoviruses are widely used as a gene delivery vector due to an intermediate sized genome, ease of manipulation, high titer, a wide range of target cells, and high infectivity. Both ends of the genome have a 100-200 bp inverted terminal repeat (ITR), which is a cis-element necessary for DNA replication and packaging. The E1region (E1A and E1B) of the genome encodes proteins responsible for the regulation of transcription and transcription of host cell genes. The E2 region (E2A and E2B) encodes proteins involved in viral DNA replication. Among currently developed adenoviruses, E1 region-deleted replication-incompetent adenoviruses are widely used. Meanwhile, the E3 region is removed from a general adenovirus vector to provide a site into which a foreign gene is inserted (Thimmappaya, B. et al., Cell, 31:543-551(1982); and Riordan, J. R. et al., Science, 245:1066-1073(1989)).

The adenovirus of the present invention comprises the fiber sequence of SEQ ID NO: 1. Conventionally, the availability of adenoviruses as a carrier for gene or cell therapy has been researched, but these adenoviruses are rapidly removed in the blood or cause other immune responses, thus reducing therapeutic efficiency. To address this, loading of an adenovirus in a mesenchymal stem cell has been proposed, but the efficiency of introduction of an adenovirus into a mesenchymal stem cell is very low, and, when stem cells are infected with an adenovirus at a high concentration in order to enhance the introduction efficiency of the adenovirus, the viability of the stem cells is reduced, thus causing problems such as death of the stem cells before reaching a tumor site, and therefore, it is difficult to actually use adenovirus-loaded mesenchymal stem cells as a therapeutic agent.

However, in the case of a recombinant adenovirus comprising the fiber sequence of SEQ ID NO: 1 of the present invention, the efficiency of introduction thereof into a mesenchymal stem cell is significantly high, and the adenovirus has the ability to be introduced into the stem cell well even at a low virus concentration. Thus, in view that the disadvantages of adenoviruses and low efficiency of introduction into stem cells, which have been problems in conventional gene therapies, have been addressed, the present invention has very important patentability.

Figure 17:
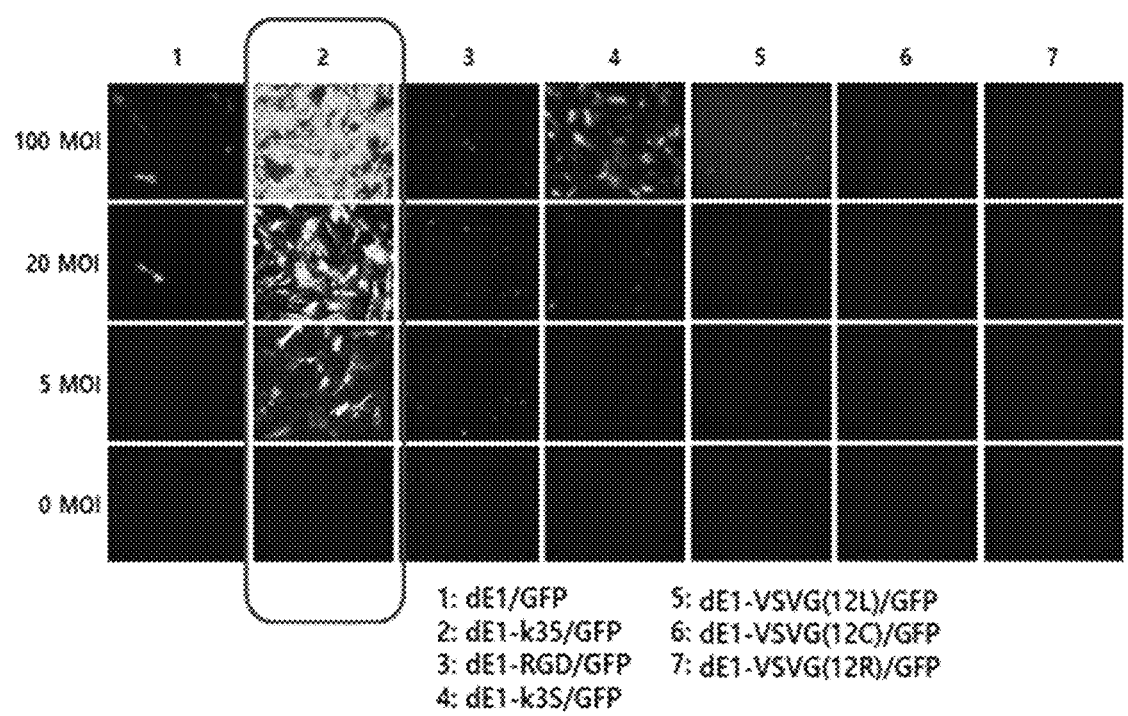
FIG. 17 illustrates the results of confirming the gene delivery efficiencies of recombinant adenoviruses constructed according to an embodiment of the present invention according to adenovirus fiber modification.
Figure 18:
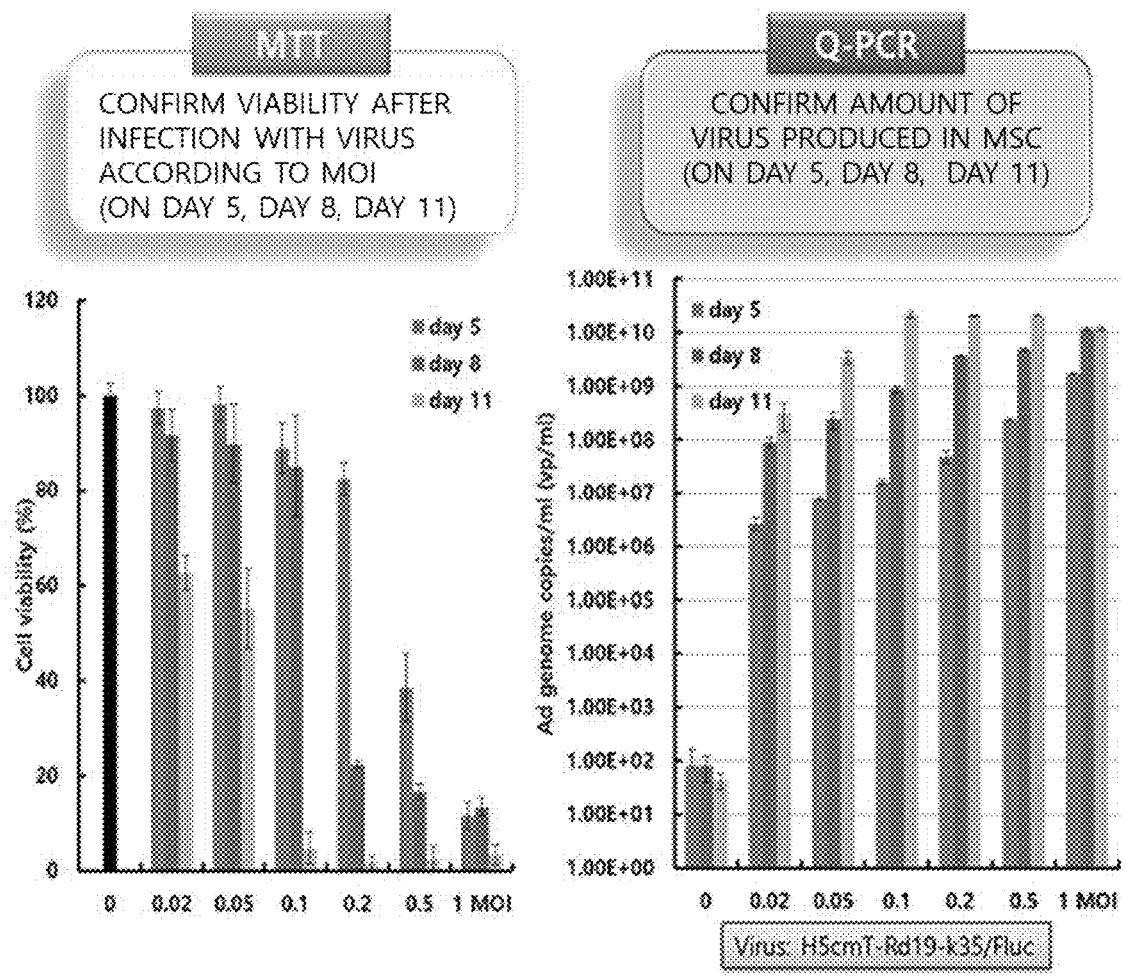
FIG. 18 is a set of graphs showing the results of confirming, through MTT assay, the cancer cell-killing efficacy by an oncolytic adenovirus loaded in mesenchymal stem cells, constructed according to an embodiment of the present invention and the results of confirming, through Q-PCR, the viral proliferative capacity thereof in mesenchymal stem cells.

In one embodiment of the present invention, when the adenovirus of the present invention was introduced into a mesenchymal stem cell, it was confirmed that the viral vector was well introduced into the mesenchymal stem cell even at 0.02 MOI (see FIG. 18). In addition, in the case of using other vectors, viral vectors were not well introduced even at 100 MOI or 500 MOI (see FIGS. 17 and 24), whereas, in the case of using the recombinant adenovirus of the present invention, the viral vector was introduced very well even at 5 MOI.

In the Ad-loaded mesenchymal stem cell of the present invention, to optimize anticancer effects using the same and the effect of delivering the Ad-loaded MSC to a target site, the amount of adenovirus (Ad) loaded in a stem cell may be adjusted.

Specifically, MSCs may be infected for 50 hours or less using an adenovirus at greater than 0.001 MOI to less than 100 MOI. Preferably, MSCs may be infected therewith at 0.01 MOI to 100 MOI. More particularly, MSCs may be infected for 50 hours or less with serotype 35 knob-comprising Ad at a concentration of 50 MOI or less, greater than 0.01 MOI to 50 MOI, or 2 MOI to 10 MOI, thereby loading the adenovirus in the mesenchymal stem cells. In this case, problems such as reduced viability of MSCs themselves due to an excessive amount of an adenovirus, can be addressed and the proliferation of Ad in MSCs can be optimized, and thus, when MSCs injected into the body reach a target site, a stronger anticancer effect may be obtained by the proliferation of Ad, thereby producing Ad-loaded MSCs with optimal conditions that make a balance between viral proliferation and MSC viability.

The adenovirus of the present invention may further comprise a gene expression regulatory sequence. The gene expression regulatory sequence may be comprised in conventional adenoviruses, and any gene expression regulatory sequence known in the art to which the present invention pertains falls within the scope of the present invention without limitation.

The gene expression regulatory sequence may be inserted into a promoter sequence position of the E1A gene to regulate the expression of the E1A gene. In addition, a gene expression regulatory sequence-expressing gene cassette of the present invention is preferably inserted into a deleted E1 region (E1A region and/or E1B region, preferably an E1B region) and/or a deleted E3 region, more preferably, into a deleted E1 region. In addition, the gene expression regulatory sequence-expressing gene cassette of the present invention may also be inserted into a deleted E4 region. The term "deletion" as used herein with regard to viral genomic sequences means that the corresponding sequence is completely or partially deleted.

In a specific embodiment, when the gene expression regulatory sequence of the present invention is located upstream of the E1A gene, i.e., when the gene expression regulatory sequence of the present invention is operatively linked to the E1A gene (HRE-Ea-Eb-AFPm-E1A), the replication of the recombinant adenovirus is regulated by the gene expression regulatory sequence of the present invention. When the gene expression regulatory sequence of the present invention is located in a deleted E3 gene region, the gene expression regulatory sequence may be inserted, in the form of a "gene expression regulatory sequence-target gene"-expressing cassette, into the deleted E3 gene region. When the gene expression regulatory sequence of the present invention is located in a deleted E4 gene region, the gene expression regulatory sequence may be inserted, in the form of a "gene expression regulatory sequence-target gene"-expressing cassette, into the deleted E4 gene region.

A target gene, which is to be inserted into the recombinant adenovirus, may be inserted in the form of a cassette expressing promoter-target gene. In this case, as the promoter, the gene expression regulatory sequence of the present invention (e.g., Ea-Eb-AFPm, Ea2-Eb-AFPm, or HRE6-Ea2-Eb-AFPm) or a general promoter may be used. The general promoter which binds to the target gene may act on preferably animal cells, more preferably mammalian cells and regulate the transcription of the target gene, and comprises promoters derived from mammalian viruses and promoters derived from the genomes of mammalian cells, for example, a U6 promoter, a H1 promoter, a cytomegalovirus (CMV) promoter, an adenovirus late promoter, a vaccinia virus 7.5K promoter, a SV40 promoter, a tk promoter of HSV, a RSV promoter, an EF1-α promoter, a metallothionein promoter, a β-actin promoter, a human IL-2 gene promoter, a human IFN gene promoter, a human IL-4 gene promoter, a human lymphotoxin gene promoter, a human GM-CSF gene promoter, an inducible promoter, cancer cell-specific promoters (e.g., a TERT promoter, a PSA promoter, a PSMA promoter, a CEA promoter, an E2F promoter, and an AFP promoter), and tissue-specific promoters (e.g., an albumin promoter), but the present invention is not limited thereto.

In an expression construct for expressing the target gene, a polyadenylation sequence is preferably bound downstream of the target gene. The polyadenylation sequence comprises a bovine growth hormone terminator (Gimmi, E. R., et al., Nucleic Acids Res. 17:6983-6998(1989)), a SV40-derived polyadenylation sequence (Schek, N, et al., Mol. Cell Biol. 12:5386-5393(1992)), HIV-1 polyA (Klasens, B. I. F., et al., Nucleic Acids Res. 26:1870-1876(1998)), β-globin polyA (Gil, A., et al, Cell 49:399-406(1987)), HSV TK polyA (Cole, C. N. and T. P. Stacy, Mol. Cell. Biol. 5:2104-2113 (1985)), or polyomavirus polyA (Batt, D. B and G. G. Carmichael, Mol. Cell. Biol. 15:4783-4790(1995)), but the present invention is not limited thereto.

In addition, since an adenovirus can pack up to about 105% of the wild-type genome, about 2 kb can be additionally packed (Ghosh-Choudhury et al., *EMBO J.,* 6:1733-1739(1987)). Therefore, the foreign sequences described above, which are inserted into the adenovirus, may be further linked to the genome of the adenovirus.

Foreign genes delivered by an adenovirus are replicated in the same manner as episomes, and the genetic toxicity against host cells is very low. Therefore, it is determined that gene therapy using the adenovirus gene delivery system of the present invention is very safe.

The term "K35 fiber" as used herein refers to an adenovirus serotype 35 fiber protein or a nucleotide sequence encoding the protein. Adenoviruses are 70-90 nm nonenveloped viruses with a capsid, wherein the capsid consists of the hexon, fiber, and penton base, which are three main exposed structural proteins, and a knob-type protein which protrudes from a penton region, which is each of the vertexes of the capsid, is referred to as fiber. An adenovirus binds to a receptor of a cell to be infected or the like via the fiber protein, and is known to exhibit different infections and symptoms according to serotype.

The sequence of the K35 fiber may comprise a nucleotide sequence of SEQ ID NO: 1, and preferably, may consist of a nucleotide sequence of SEQ ID NO: 1.

In one embodiment of the present invention, as a result of converting the fiber of an adenovirus that delivers a target gene into K35, it was confirmed that the gene was well introduced into a mesenchymal stem cell (MSC) even with a low concentration of the adenovirus. It was also confirmed that, in the case of mesenchymal stem cells infected with an excessive concentration of a virus in order to introduce the adenovirus into the mesenchymal stem cells, the mesenchymal stem cells rather died, showing low viability, whereas, in the case of mesenchymal stem cells infected with a low concentration of the adenovirus, the adenovirus proliferated in the mesenchymal stem cells after loading of the adenovirus, and thus when administered, the stem cells exhibited a further enhanced anticancer effect.

In one embodiment, the gene expression regulatory sequence comprised in the adenovirus of the present invention may further comprise: a gene expression regulatory sequence comprising, in a 5' to 3' direction, (a) a hypoxia-response element (HRE) domain sequence, (b) an alpha-fetoprotein (AFP) promoter enhancer A sequence, (c) an AFP promoter enhancer B sequence, and (d) an AFP promoter sequence; and a target gene that is operatively linked to the gene expression regulatory sequence.

Therefore, the adenovirus of the present invention may be an adenovirus comprising: a gene expression regulatory sequence comprising, in a 5' to 3' direction, (a) a sequence of 6 copies of the hypoxia-response element (HRE), (b) a sequence of 2 copies of alpha-fetoprotein (AFP) enhancer A, (c) a sequence of one copy of AFP promoter enhancer B, and (d) an AFP promoter sequence; a target gene that is operatively linked to the gene expression regulatory sequence; and a serotype 35 fiber knob sequence.

In another embodiment, the adenovirus of the present invention may comprise a gene expression regulatory sequence comprising a 5MMTERT promoter and a target gene that is operatively linked to the gene expression regulatory sequence.

The gene expression regulatory sequence refers to a sequence capable of regulating expression so that the target gene can be expressed only under specific conditions.

As used herein, the term "AFP promoter" refers to a promoter that promotes the expression of the alpha-fetoprotein (AFP) protein, which is a serum protein highly expressed in the liver during yolk sac and fetal development stages. Since the AFP protein is rarely detected except for adult liver cancer patients, it is used as a useful marker for liver cancer, and the level of AFP expression in serum considerably varies due to the difference in activity between enhancers that regulate the expression thereof. Therefore, when an expression regulatory sequence consisting of a specific combination of AFP promoters and enhancers is used, a target/therapeutic gene to be delivered may be allowed to be specifically expressed in cancer cells. The sequence of the AFP promoter may comprise a nucleotide sequence of SEQ ID NO: 5.

As used herein, the term "HRE domain sequence" refers to a hypoxic-reactive enhancer sequence. Under hypoxic conditions, the expression of specific genes in a cell is regulated (Bunn and Poyton Physiol. Rev. 76:839-885 (1996); Dachs and Stratford Br. J. Cancer 74:5126-5132 (1996); Guillemin and Krasnow Cell 89:9-12(1997)). Most tumor cells receive an inadequate blood supply because tumor cells typically grow faster than endothelial cells that form blood vessels, which causes hypoxia in tumors. These hypoxic conditions, which occur in most solid tumors, result in the production of survival factors such as glycolytic enzymes and proangiogenic factors, making them resistant to radiation and chemotherapy. The primary mediator of the hypoxic response is transcriptional complex hypoxia inducible factor (HIF)-1α, which interacts with HRE at regulatory sites of various genes, and the genes comprise, for example, the vascular endothelial growth factor (VEGF) gene, and glycolytic enzyme-encoding genes such as enolase-1 and glyceraldehyde-3-phosphate dehydrogenase (GAPDH). The present invention may use HRE, which is a sequence that regulates the expression of genes in hypoxic conditions and interacts with HIF-1α. In the present invention, the HRE not only can greatly enhance tumor cell selectivity of a recombinant adenovirus, but also serves to enhance the proliferative capacity of an adenovirus.

According to an exemplary embodiment of the present invention, the gene expression regulatory sequence of the present invention may comprise a HRE sequence, and preferably, may comprise a HRE repeat sequence in order to enhance transcriptional activity by the HRE sequence. More preferably, the gene expression regulatory sequence of the present invention may comprise 1 to 10 repeats, further more preferably 3 to 8 repeats, and most preferably 5 to 7 repeats, of the nucleotide sequence of SEQ ID NO: 6. In one embodiment, the 6 copies of a hypoxia-response element (HRE) domain sequence may comprise a sequence of SEQ ID NO: 2.

The gene expression regulatory sequence may comprise an enhancer A sequence of SEQ ID NO: 3 to improve the expression efficiency of a gene to be delivered, and the enhancer A sequence may be comprised in the form of a repeat sequence. In the repeat sequence of the present invention, the same sequence may be continuously repeated (immediately adjacent), or may also be discontinuously repeated with a linker nucleotide of an appropriate length interposed therebetween within a range that does not affect the activity of a promoter or enhancer.

Preferably, the enhancer A sequence comprised in the gene expression regulatory sequence of the present invention may be a sequence in which the nucleotide sequence of SEQ ID NO: 3 is repeated 1 to 10 times, further more preferably, repeated 2 to 6 times, and most preferably, repeated 3 to 5 times.

According to an exemplary embodiment of the present invention, the gene expression regulatory sequence of the present invention comprises, in the 5' to 3' direction, a HRE domain sequence, an enhancer A sequence, an enhancer B sequence, and an AFP promoter sequence. In addition, preferably, the HRE sequence may be repeated six times, and the enhancer A sequence may be repeated twice.

According to an exemplary embodiment of the present invention, the recombinant adenovirus of the present invention may further comprise a target gene that is operatively linked to the gene expression regulatory sequence.

As used herein, the term "operatively linked" refers to functional binding between a nucleic acid expression regulatory sequence (e.g., an array of promoters, signal sequences, or transcriptional regulator binding sites) and other nucleic acid sequences, and the regulatory sequence thereby regulates transcription and/or translation of the other nucleic acid sequences. The type of gene (target gene) to be expressed, which is operatively linked to the gene expression regulatory sequence of the present invention, is not particularly limited.

The gene to be expressed may also be referred to as a target gene in terms of a gene to express the function of the gene at the target site, and the target gene may be a therapeutic gene. The therapeutic gene may also be referred to as the term "therapeutic transgene" in the specification of the present invention. As used herein, the term "therapeutic transgene" refers to a nucleotide sequence exhibiting the effect of alleviating or treating diseases or symptoms. The therapeutic transgene may be, for example, a nucleotide sequence that is expressed in cancer cells and exhibits a therapeutic effect.

The target gene may be selected from the group consisting of, for example, a tumor suppressor gene, a suicide gene, an antigenic gene, an immune-enhancing gene, a cytotoxic gene, a cell proliferation inhibitory gene, an apoptotic gene, anti-angiogenic gene, a metastasis inhibitory gene, an antibody gene, an immunomodulatory gene, and nucleotides that can be delivered by the vector of the present invention.

As used herein, the term "tumor suppressor gene" refers to a nucleotide sequence that can be expressed in target cells to inhibit tumor phenotype or induce apoptosis. Tumor suppressor genes useful in the practice of the present invention comprise the p53 gene, the APC gene, the DPC-4/Smad4 gene, the BRCA-1 gene, the BRCA-2 gene, the WT-1 gene, retinoblastoma genes (Lee et al., Nature, 1987, 329,642), the MMAC-1 gene, adenomatous polyposis coil protein (U.S. Pat. Publication No. 5,783,66), deleted colorectal carcinoma (DCC) genes, the MMSC-2 gene, the NF-1 gene, a nasopharyngeal cancer suppressor gene located on chromosome 3p21.3 (Cheng et al. Proc. Nat. Acad. Sci, 95:3042-3047(1998)), the MTS1 gene, the CDK4 gene, the NF-1 gene, the NF-2 gene, and the VHL gene.

In the present invention, the foreign gene sequence to be delivered by an antitumor adenovirus into a cell is a cancer treatment gene that induces the death of cancer cells and ultimately degenerates tumors. Examples of the cancer treatment gene comprise, but are not limited to, tumor suppressor genes, immunomodulatory genes [e.g., cytokine genes, chemokine genes, and costimulatory factors (auxiliary molecules necessary for T cell activation, such as B7.1 and B7.2)], antigenic genes, suicide genes, cytotoxic genes, cytostatic genes, pro-apoptotic genes, and anti-angiogenic genes.

A suicide gene is a nucleic acid sequence that expresses a substance for inducing a cell to be easily killed by an external factor or induces toxic conditions in a cell. A gene well-known as such a suicide gene is the thymidine kinase (TK) gene (U.S. Pat. Nos. 5,631,236 and 5,601,818). TK gene product-expressing cells are susceptible to selective killing by administration of gancyclovir. A tumor suppressor gene refers to a gene encoding a polypeptide that inhibits tumorigenesis. The tumor suppressor gene is a naturally occurring gene in mammals, and the deletion or inactivation of this gene is believed to be a prerequisite for tumorigenesis. Examples of tumor suppressor genes comprise APC, DPC4, NF-1, NF-2, MTS1, WT1, BRCA1, BRCA2, VHL, p53, Rb, MMAC-1, MMSC-2, retinoblastoma genes (Lee et al. Nature, 329:642(1987)), the adenomatous polyposis coli protein (U.S. Pat. No. 5,783,666), the nasopharyngeal cancer suppressor gene that is located on chromosome 3p21.3 (Cheng et al. Proc. Nat. Acad. Sci., 95:3042-3047(1998)), deleted colon carcinoma (DCC) genes, MTS1, CDK4, VHL, p110Rb, and members of the INK4 family of tumor suppressor genes comprising p16 and p21, and therapeutically effective fragments thereof (e.g., p56Rb, p94Rb, and the like). It will be understood by one of ordinary skill in the art that other known antitumor genes, in addition to the above-listed genes, may be used.

The term "antigenic gene" as used herein refers to a nucleotide sequence which is expressed in target cells to produce cell-surface antigenic proteins that can be recognized by the immune system. Examples of such antigenic genes comprise carcinoembryonic antigens (CEAs), HER-2, prostate specific antigens (PSAs), and p53 (Levine, A., WO 94/02167). To facilitate recognition of the antigenic gene by the immune system, the antigenic gene may be bound to a MHC I-type antigen.

The term "cytotoxic gene" as used herein refers to a nucleotide sequence exhibiting toxic effects through expression in a cell. Examples of the cytotoxic genes comprise nucleotide sequences encoding *Pseudomonas* exotoxin, ricin toxin, diphtheria toxin, cytosine deaminase (CD), super-cytosine deaminase (Super-CD), thymidine kinase (TK), and the like.

The term "cytostatic gene" as used herein refers to a nucleotide sequence which is expressed in cells to stop a cell cycle during the same. Examples of such cytostatic genes comprise, but are not limited to, p21, retinoblastoma genes, E2F-Rb-fused protein genes, cyclin-dependent kinase inhibitor-encoding genes (e.g., p16, p15, p18, and p19), and growth arrest specific homeobox (GAX) genes (WO 97/16459 and WO 96/30385).

The term "apoptotic gene" as used herein refers to a nucleotide sequence that is expressed, resulting in programmed cell death. Examples of these pro-apoptotic genes comprise p53, TRAIL, MDA-7(IL-24), adenovirus E3-11.6K (derived from Ad2 and Ad45) or adenovirus E3-10.5K (derived from Ad), an adenovirus E4 gene, p53 pathway genes, and genes encoding caspases.

The term "anti-angiogenic gene" as used herein refers to a nucleotide sequence that is expressed, resulting in the extracellular secretion of anti-angiogenic factors. Non-limiting examples of anti-angiogenic factors comprise vastatin, angiostatin, inhibitors of vascular endothelial growth factor (VEGF) such as Tie 2 (PNAS, 95:8795-800(1998)), endostatin, VEGF decoy proteins, VEGF Trap, and VEGF siRNA.

"Metastasis inhibitory gene," which inhibits metastasis caused by infiltration, comprises, for example, BRMS1, CRSP3, DRG1, KAI1, KISS1, NM23, and various tissue inhibitors of metalloproteinase (TIMP).

As used herein, the term "antibody gene" refers to a nucleotide sequence that produces a specific antibody capable of inducing apoptosis of cancer cells by binding to antigens preferentially or exclusively expressed in cancer cells, unlike normal cells. Examples of these antibody genes comprise nucleotide sequences encoding anti-DR4/DR5, anti-CTLA-4, anti-PD-1, anti-PD-L1, anti-Her2/neu, anti-VEGF, anti-VEGFR, anti-cMet, anti-Survivin, anti-EGFR, anti-Wnt, anti-Ly49, and the like.

As used herein, the term "immune-related gene (immune-modulating gene)" refers to all genes that regulate the expression of immune-related factors, and examples thereof comprise genes encoding cytokines (e.g., interferon-α, interferon-β, interferon-γ and interferon-δ), interleukins (e.g., IL-1, IL-2, IL-4, IL-6, IL-7, IL-10, IL-12, IL-17, IL-18, IL-19, IL-20, and IL-23), and colony-stimulating factors (e.g., GM-CSF and G-CSF), a chemokine group (monocyte chemotactic protein 1 (MCP-1), monocyte chemotactic protein 2 (MCP-2), monocyte chemotactic protein 3 (MCP-3)), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), an EBI1-ligand chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), an eotaxin, I-309, human protein HCC-1/NCC-2, human protein HCC-3, mouse protein C10), and costimulatory factors (auxiliary molecules necessary for T cell activation, such as B7.1 and B7.2).

In addition, the nucleotides that can be delivered by the vector of the present invention comprise CD44v3/6, adenovirus death proteins (ADPs), IFN-γ, HIF-1α siRNA, idolamine 2,3-dioxygenase2 (IDO2) siRNA, Wnt decoy proteins, VEGF decoy proteins, cMet siRNA, microRNA (microRNA-26A), miR-99a, miR-143, miR-193a-3p, miR-206, miR-506 (fokhead box Q1), shAktl, shMYO6, sodium-iodine symporter (NIS), HSV-TK, LMP2A/LMP1, IP-10/CXCL10, PF-4var/CXCL4L1, oncostatin M, CD 147-targeted human-mouse chimeric antibodies, humanized antibodies, Lin28-targeted zinc finger proteins, VEGF-targeted zinc finger proteins, cMet-targeted zinc finger proteins, the Cas 9 protein and guiding RNA, the TALEN protein, the TRAIL protein, or phosphatase and tensin homolog protein (PTEN)-encoding genes, and the therapeutic transgene of the present invention is not limited thereto.

The above-described miR-99a targets mTOR, AKT1, and FGFR3, and the miR-193a-3p targets the PSEN1 gene.

According to one embodiment of the present invention, the recombinant adenovirus of the present invention may further comprise fluorescent protein-encoding nucleotides in a capsid protein-encoding nucleotide. In this case, it is possible to provide a recombinant adenovirus whose location is easy to track in a cell into which the adenovirus is inserted.

According to the present invention, when a fluorescent marker protein is inserted into a protein constituting the capsid of an adenovirus, it is possible to track the path and distribution of the virus in real time. When a label gene is inserted into the gene of a virus, the expression of the protein is confirmed only after the DNA is converted to the protein, whereas, in the case of a virus with the label protein bound to the IX protein, regardless of the viral infection pathway, it is possible to track the expression of the protein and the location of the virus from the initial stage of viral infection. Therefore, the present invention may be used as a useful non-invasive molecular imaging tool.

According to an exemplary embodiment of the present invention, the capsid protein of the present invention may be pIX.

According to an exemplary embodiment of the present invention, the fluorescent protein of the present invention may be selected from the group consisting of green fluorescent protein (GFP), red fluorescent protein (RFP), cyan fluorescent protein (CFP), yellow fluorescent protein (YFP), blue fluorescent protein (BFP), enhanced green fluorescent protein (EGFP), enhanced cyan fluorescent protein (ECFP), enhanced yellow fluorescent protein (EYFP), enhanced red fluorescent protein (ERFP), enhanced blue fluorescent protein (EBFP), and luciferase.

Mesenchymal stem cells (MSCs) are a type of adult stem cell and have been reported to be capable of differentiating into various cells such as adipocytes, osteoblasts, and chondrocytes. Mesenchymal stem cells have been actively studied as one of the gene carriers, but lack specific receptors, or the like, and thus are not infected with an adenovirus, which makes it difficult to be used as a gene carrier.

However, the recombinant adenovirus of the present invention has an improved ability to be introduced into mesenchymal stem cells by modification of fiber proteins, and thus can be effectively used as a gene carrier that delivers a target gene to a desired site in the body.

In the case of mesenchymal stem cells, it was difficult to load an adenovirus therein, and thus a large number of adenoviruses was required to load the adenovirus to a level that can be used as a gene therapeutic agent. However, in this case, the mesenchymal stem cells exhibit deteriorated viability and characteristics due to an adenovirus, and there is a problem that causes rapid death of the mesenchymal stem cells. However, it was experimentally confirmed that, when the recombinant adenovirus comprising the sequence of SEQ ID NO: 1 of the present invention is loaded in a mesenchymal stem cell, the adenovirus was loaded well even at a low concentration (MOI). Accordingly, the recombinant adenovirus-loaded stem cell (Ad-MSC) of the present invention has higher viability than that of other stem cells, acts as a culture in which the loaded adenovirus can proliferate, and inherently does not cause immunogenicity, and thus may be used as an excellent gene carrier for gene therapy.

In one embodiment of the present invention, the stem cells may be administered systemically or locally. For example, the systemic administration may be intravenous administration, intraperitoneal administration, intrapulmonary administration, and intravesical injection, but the present invention is not limited thereto. In conventional gene therapies, when an adenovirus is itself used as a gene carrier, there is a problem in that the adenovirus disappears or causes hepatotoxicity before reaching a target site after being injected into the body, due to immunogenicity thereof or the like. However, the adenovirus-loaded stem cell (Ad-MSC) of the present invention can be administered systemically due to reduced or no immunogenicity thereof, and has an excellent ability to target tumor cells, thus not causing hepatotoxicity.

In this regard, a composition for gene delivery of the present invention may be for systemic administration. When a conventional adenovirus vector is used alone as a gene carrier, it is impossible to systemically administer the vector, and the adenovirus vector disappears due to immune cells and the like in the body before reaching a target site, making it difficult to deliver a gene into the target site. However, the adenovirus-loaded stem cell (Ad-MSC) of the present invention exhibits reduced or no immune responses other than cancer-specific characteristics, can be administered systemically, has an excellent ability to target tumor cells, and does not cause hepatotoxicity, thus significantly enhancing gene delivery efficiency.

The mesenchymal stem cells may be isolated from bone marrow and the like, and patient's own mesenchymal stem cells or allogeneic mesenchymal stem cells using the database of a blood bank may be used. Thus, when the adenovirus-loaded stem cells of the present invention are used as a gene carrier, both self-treatment and allogeneic therapy are possible, thus further reducing gene therapy costs.

A method of loading, in a mesenchymal stem cell, the adenovirus of the present invention comprising a gene expression regulatory sequence and a target gene may be performed using various methods known in the art. In particular, the loading of the gene may be performed using a virus infection method known in the art.

A recombinant adenovirus comprising a gene expression regulatory sequence, a target gene, and a K35 fiber, according to the present invention, is the same as described above, and the descriptions thereof will be omitted herein to avoid the repetition of the description.

According to another embodiment of the present invention, there is provided a composition for gene delivery, comprising a mesenchymal stem cell (MSC) with the recombinant adenovirus comprising a sequence of SEQ ID NO: 1 loaded therein.

The composition for gene delivery of the present invention may be a composition for cancer-specific gene delivery.

According to one embodiment of the present invention, the gene expression regulatory sequence comprised in the adenovirus may be designed as a promoter and enhancer capable of specifically expressing genes in liver cancer cells, and also comprises a HRE domain sequence so that gene expression is excellent under hypoxic conditions. Thus, in a specific embodiment of the present invention, it was confirmed that gene expression occurred specifically both in AFP-positive liver cancer cells and AFP-negative liver cancer cells, and a target gene was not expressed in normal cells.

According to another embodiment of the present invention, in view of the disclosure of the present invention that tumor tissue-specific therapeutic effects are exhibited using pan-cancer specific oncolytic Ads that can be used for treatment regardless of the type of carcinoma, the effect of the composition for gene delivery of the present invention may vary depending on the type of target gene, and thus the type of cancer is not limited.

The descriptions of the recombinant adenovirus and stem cell of the present invention will be omitted herein to avoid the repetition of contents of the foregoing descriptions, and the above descriptions can be applied mutatis mutandis.

Another embodiment of the present invention provides a pharmaceutical composition comprising a pharmaceutically effective amount of mesenchymal stem cells (MSCs) with a recombinant adenovirus loaded therein, the recombinant adenovirus comprising: a gene expression regulatory sequence comprising, in a 5' to 3' direction, (a) a hypoxia-response element (HRE) domain sequence, (b) an alpha-fetoprotein (AFP) enhancer A sequence, (c) an AFP promoter enhancer B sequence, and (d) an AFP promoter sequence; a therapeutic gene that is operatively linked to the gene expression regulatory sequence; and a serotype 35 (K35) fiber knob-encoding sequence.

The pharmaceutical composition may be for cancer treatment. In the present invention, the type of cancer to be treated may vary depending on the type of therapeutic gene to be inserted into the adenovirus of the present invention, the type of promoter, and the like, and thus the type of cancer is not limited. Specifically, examples of cancer comprise, but are not limited to, gastric cancer, lung cancer, liver cancer, cervical cancer, leukemia, pancreatic cancer, pediatric solid cancer, colon cancer, skin cancer, ovarian cancer, endometrial cancer, bladder cancer, kidney cancer, head and neck cancer, brain cancer, osteosarcoma, prostate cancer, soft tissue cancer, thyroid cancer, nasopharyngeal cancer, esophageal cancer, ocular cancer, breast cancer, and biliary tract cancer.

In one embodiment of the present invention, the effect of the adenovirus as a pan-cancer-specific oncolytic adenovirus was confirmed, and thus the type of carcinoma is not limited. In addition, a gene for liver cancer treatment was inserted into the adenovirus and the effect thereof was confirmed, and thus the pharmaceutical composition may be for liver cancer treatment.

The cancer may be cancer cells or tumor tissue. In one embodiment of the present invention, the adenovirus-loaded stem cells can exhibit cancer cell-killing ability through the expression of a therapeutic gene both in AFP-positive liver cancer cells and AFP-negative liver cancer cells, and thus, regardless of the phenotype of liver cancer cells, the adenovirus-loaded stem cell of the present invention may be used for treatment.

When used for cancer treatment, the adenovirus-loaded stem cell (Ad-MSC) of the present invention enables cancer-specific expression of a therapeutic gene, thus not affecting other normal cells, can be administered systemically due to reduced or no immune responses, and has an excellent ability to target tumor cells, and does not cause hepatotoxicity, thus significantly enhancing gene delivery efficiency. In addition, the MSC itself dies due to the adenovirus after being injected into the body, and thus may prevent the occurrence of side effects caused by the retention of the MSC in the body.

As used herein, the term "treatment" means all actions that inhibit or alleviate and beneficially change clinical situations related to diseases. Treatment may also mean increased survival compared to the expected viability when not treated. The treatment may simultaneously comprise preventive means other than therapeutic means. In the present invention, treatment may mean, for example, death or killing of tumor cells.

As used herein, "individual" may be vertebrates, preferably mammals, for example, dogs, cats, mice, and humans.

The composition of the present invention may be formulated by further comprising a pharmaceutically acceptable carrier. As used herein, the term "pharmaceutically acceptable carrier" refers to a carrier or diluent that does not significantly stimulate an organism and does not inhibit the biological activity and properties of an administered ingredient. The pharmaceutically acceptable carrier of the present invention may be one selected from saline, sterile water, Ringer's solution, buffered saline, a dextrose solution, a maltodextrin solution, glycerol, and ethanol, or a mixture of two or more thereof. As necessary, other commonly used additives such as an antioxidant, a buffer, and a bacteriostatic agent may be added to the composition and formulated into an injectable form suitable for injection into tissues or organs. In addition, an isotonic sterile solution or, in some cases, sterile water or physiological saline may be added to the composition and may also be formulated into a dried preparation (particularly, a freeze-dried preparation) that can become an injectable solution.

In addition, preferably, the composition of the present invention may further comprise a filler, an excipient, a disintegrating agent, a binder, a lubricant, and the like. In addition, the compositions of the present invention may be formulated using methods known in the art so as to provide, after administration to mammals, rapid, sustained or delayed release of the active ingredient.

As used herein, the term "administration" refers to introduction of the composition of the present invention into a patient in any suitable way, and the administration route of the composition of the present invention may comprise various routes such as oral and parenteral routes as long as the composition is able to reach a target tissue. Examples of administration routes comprise, but are not limited to, intraperitoneal administration, intravenous administration, intramuscular administration, subcutaneous administration, intradermal administration, oral administration, local administration, intranasal administration, intrapulmonary administration, and intrarectal administration, preferably intravenous administration.

As used herein, "effective amount" refers to an amount necessary to delay or completely stop the onset or progression of a particular disease to be treated. In the present invention, the composition may be administered in a pharmaceutically effective amount. It is obvious to those of ordinary skill in the art that a suitable total daily dosage can be determined by a prescriber within the proper medical determination range. For the objectives of the present invention, it is preferable that a specific therapeutically effective amount for a particular patient varies depending on various factors comprising the type and degree of reaction to be achieved, specific compositions, comprising whether or not other agents are used in some cases, the age, body weight of a patient, general health conditions, gender and diet, administration time, administration route, the excretion rate of a composition, treatment period, and drugs used together or simultaneously with specific compositions, and similar factors well known in the medical field.

Hereinafter, the present invention will be described in detail with reference to the following preparation examples and experimental examples. These examples and experimental examples are provided for illustrative purposes only and are not intended to limit the scope of the present invention.

EXAMPLED

[Preparation Example] Experimental Preparation and Experimental Methods

1. Experimental Materials and Preparation

Cell lines used in the experiments of the present invention, such as HEK293 (human embryonic kidney cell line expressing adenovirus E1 region), A549 (human lung cancer cell line), AFP-positive HCC (Hep3B), and AFP-negative HCC (Hep1) were purchased from ATCC (USA) unless otherwise specifically stated herein and used. The cells were cultured in Dulbecco's Modified Eagle's Medium (Gibco BRL, Gaithersburg, MD) supplemented with 10% fetal bovine serum (FBS: Gibco BRL), penicillin (100 IU/mL), and gentamicin (20 μg/mL). All cell lines were stored in a humidified incubator at 37° C. under a 5% $CO_2$ atmosphere. Human MSCs, which were isolated from bone marrow after aspiration from healthy adult male donors, were provided by Pharmicell Co., Ltd. (Seongnam, Korea). Cryopreserved MSCs were thawed and used in the study. MSCs were incubated in low-glucose Dulbecco's Modified Eagle's Medium comprising 10% FBS (Gibco BRL), penicillin (100 IU/mL), streptomycin (50 mg/mL), and gentamicin (20 μg/mL) in a humidified incubator at 37° C. under a 5% $CO_2$ atmosphere.

In the present invention, $Ha_2bm$-d19-k35/sLRP6, $Ha_2bm$-d19-k35/WNTi, or HCC-oAd-WNTi was used interchangeably for liver cancer-specific WNTi-expressing adenoviruses.

2. Statistical Analysis

Data was expressed as mean±standard deviation (SD). Statistical significance was determined by a bilateral Student T-test or One-way Anova test (SPSS 13.0 software, SPSS, Chicago, IL). A P value of less than 0.05 was considered statistically significant.

Example 1

Construction of Liver Cancer-Specific Oncolytic Adenoviruses

Experimental Example 1-1

Construction of Liver Cancer-Specific Promoters Through Recombination of Enhancer and Silencer Regions of AFP Promoter To develop liver cancer-specific adenoviruses, first, promoter regions of the AFP protein, which is highly expressed in patients with liver cancer, were subjected to recombination and the activities of respective promoters were compared.

Specifically, from phAFP5.1 into which a 5.1 Kb AFP promoter region was inserted, enhancer A (365 bp, SEQ ID NO: 3), enhancer B (193 bp, SEQ ID NO: 4), a distal silencer (90 bp), a proximal silencer (156 bp), and an AFP minimal promoter (300 bp, SEQ ID NO: 5) regions were respectively amplified by PCR to obtain DNA fragments and the respective fragments were sequentially inserted into a pGL3-Basic vector into which luciferase was inserted as a marker gene, thereby constructing modified AFP promoters (see FIG. 1).

Experimental Example 1-2

Figure 2:
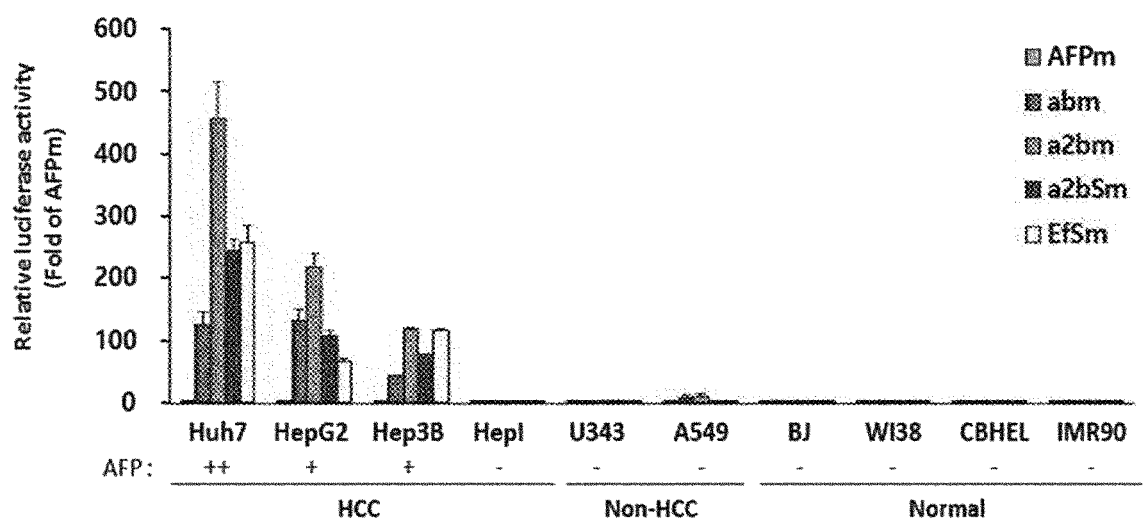
FIG. 2 is a graph showing the results of confirming the liver cancer-specific activity of a recombinant AFP promoter produced according to an embodiment of the present invention.

Comparison Between Activities of Liver Cancer-Specific Promoters Constructed Through Recombination of Enhancer and Silencer Regions of AFP Promoter To confirm the activity of tissue-specific luciferase by the AFP promoters constructed according to Experimental Example 1-1, HCC cell lines Huh7 with high AFP expression, Hep3B and HepG2 exhibiting a middle level of AFP expression, and Hep1 with no AFP expression, cancer cells of other tissues except for liver cancer, i.e., U343, which is a brain cancer cell line, and A549, which is a lung cancer cell line, and human normal cell lines BJ, WI38, CBHEL, and IMR90 were transformed with each DNA and lysed for 48 hours to perform luciferase activity assay (see FIG. 2).

As illustrated in FIG. 2, luciferase activity was high in the HCC cell lines expressing AFP, the Huh7, Hep3B, and HepG2 cell lines, and almost no luciferase activity was shown in hep1 with no AFP expression, cancer cells of other tissues, and normal cells. Among the promoters used in the experiment, the activity of the luciferase linked to $a_2bm$ in which 2 copies of enhancer A and one copy of enhancer B are bound to a minimal promoter was highest, and it was confirmed that the plasmid also had tissue specificity expressed specifically in liver cancer.

Experimental Example 1-3

Construction of Adenovirus Shuttle Vectors in which Gene Expression is Regulated by Modified AFP Promoters Based on the results of the experiment (luciferase assay) using plasmids in which luciferase expression was regulated by various recombinant promoters of Experimental Example 1-2, $a_2bm$ and $a_2bSm$, which are promoters exhibiting the highest gene delivery efficiency, were selected, AFPm was used as a negative control, and each promoter was inserted into the gene of a non-replicable adenovirus, thereby constructing viruses.

Figure 3:
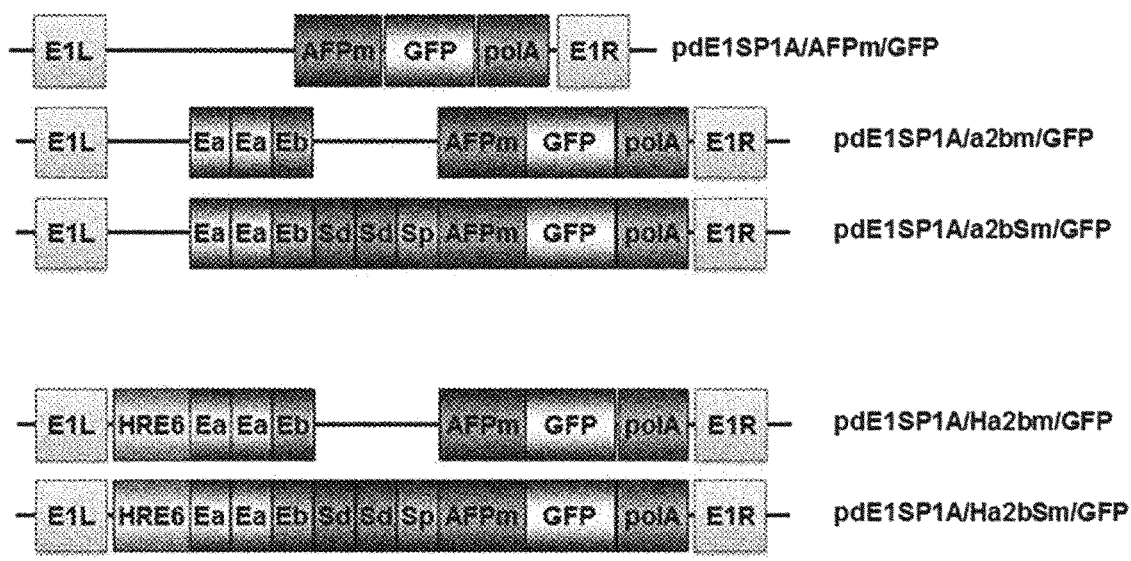
FIG. 3 illustrates the structures of shuttle vectors of adenovirus into which a promoter is inserted and in which gene expression is regulated produced according to an embodiment of the present invention.

For the non-replicable adenovirus, first, the GFP gene was inserted into adenovirus E1 shuttle vector pΔE1sp1A by using restriction enzymes HindIII and EcoRI, thereby constructing a pΔE1sp1A/GFP shuttle vector. The constructed vector was cleaved with XhoI and BglII and each AFPm promoter was inserted thereinto, thereby constructing pΔE1sp1A/AFPm/GFP into which the AFPm promoter was inserted, pΔE1sp1A/$a_2bm$/GFP into which the $a_2bm$ promoter was inserted, and pΔE1sp1A/$a_2bSm$/GFP into which the $a_2bSm$ promoter was inserted, respectively. In addition, to prevent the inhibition of viral activity even in a hypoxic state, 6 copy repeats of the HRE domain of VEGF, which is a vascular endothelial growth factor, were inserted into an upstream M1uI region of the AFP promoter, thereby constructing pΔE1sp1A/$Ha_2bm$/GFP and pΔE1sp1A/$Ha_2bSm$/GFP shuttle vectors (see FIG. 3).

Experimental Example 1-4

Figure 4:
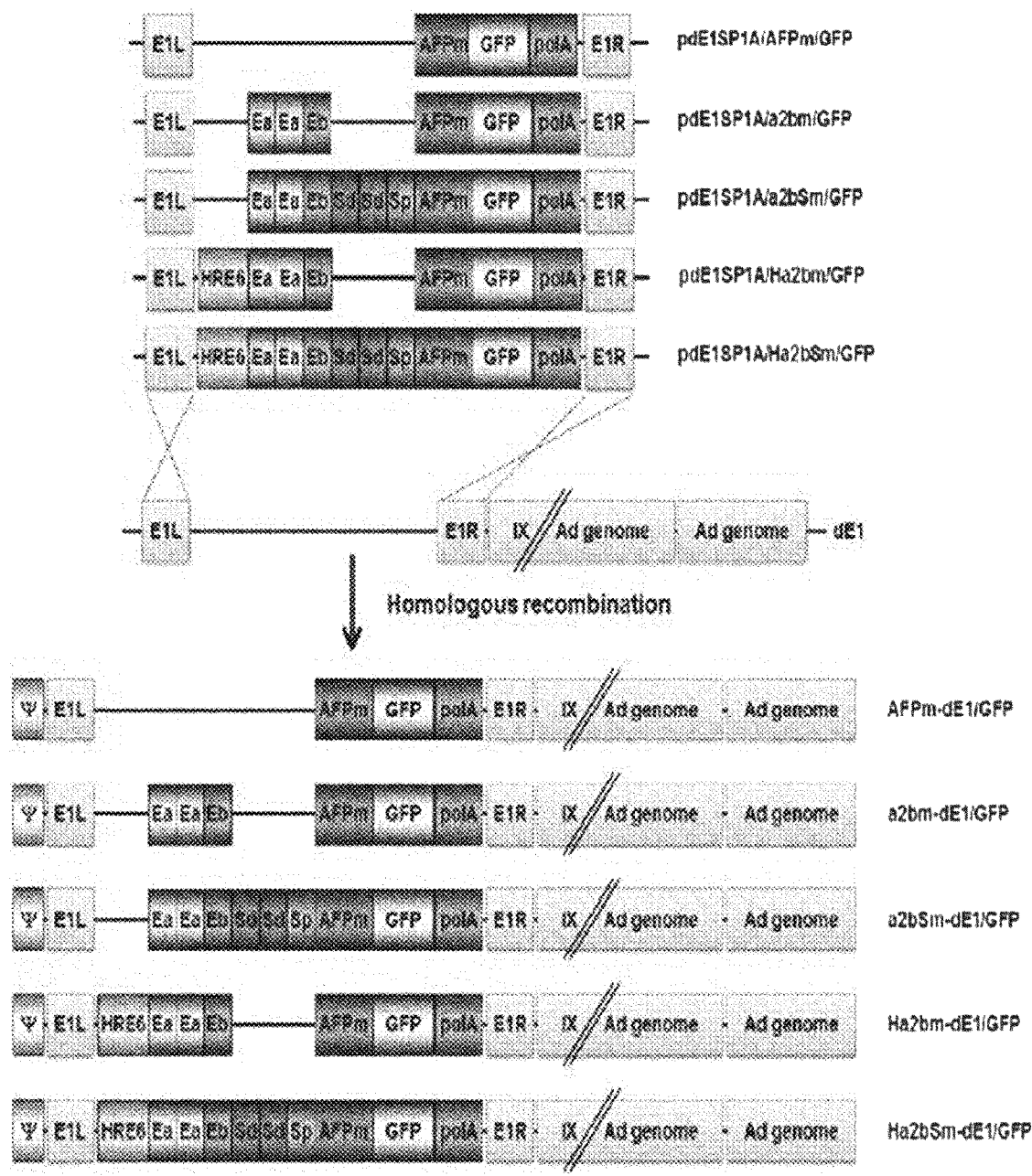
FIG. 4 illustrates the homologous recombination processes and structures of non-replicable adenoviruses with liver cancer-specific promoters produced according to an embodiment of the present invention.

Construction of Adenoviruses in which Gene Expression is Regulated by Modified AFP Promoters The five E1 shuttle vectors constructed in Experimental Example 1-3 were cleaved with restriction enzyme XmnI to be linearized, and the adenovirus total vector dE1 was cleaved with restriction enzyme BstBI to be linearized, followed by homologous recombination of the shuttle vector and the total vector in BJ5183 *E. coli*, thereby finally constructing adenoviruses AFPm-dE1/GFP, $a_2bm$-dE1/GFP, $a_2bSm$-dE1/GFP, $Ha_2bm$-dE1/GFP, and $Ha_2bSm$-dE1/GFP (see FIG. 4).

Subsequently, the five types of plasmid DNAs constructed in Experimental Example 1-3 were cleaved with restriction enzyme PacI to be linearized, followed by transfection of HEK293, which is an adenovirus-producing cell line, using Lipofectamine, thereby producing viruses. The HEK293 cell line was infected again with the produced adenoviruses, concentrated using a CsCl gradient method, purely isolated, and then limiting dilution assay and optical density (O.D) by absorbance of the viral genome were used to determine the titers of the adenoviruses.

Experimental Example 1-5

Confirmation of Whether Liver Cancer-Specific Gene Expression is Regulated by Modified AFP Promoters To confirm whether the adenoviruses, which comprise the recombinant AFP promoters (AFPm, $a_2bm$, $a_2bSm$, $Ha_2bm$, and $Ha_2bSm$) constructed in Experimental Example 1-1 and in which the expression of a liver cancer-specific gene is regulated, regulate the expression of the GFP gene, liver cancer cell lines exhibiting different levels of AFP expression (Huh7, HepG2, Hep3B, and Hep1), a cancer cell line of other tissues (A549), and a human normal cell line (HaCaT) were infected with each of the non-replicable adenoviruses (AFPm-dE1/GFP, $a_2bm$-dE1/GFP, $a_2bSm$-dE1/GFP, $Ha_2bm$-dE1/GFP, and $Ha_2bSm$-dE1/GFP), and after 48 hours, the population of GFP-expressing cells was confirmed using FACS. In addition, experimental groups for determining the activity of each promoter in a hypoxic state were infected with each adenovirus and then cultured under a hypoxic (1% $O_2$) condition, followed by culture under a normal oxygen concentration condition, wherein this cycle was repeated a total of two times. The results thereof are shown in FIGS. 6A, 6B, 6C, 6D, 6E, and 6F.

As illustrated in FIGS. 6A, 6B, 6C, 6D, and 6F, GFP expression by $Ha_2bm$-dE1/GFP was highest in AFP-expressing liver cancer cell lines (Huh7, HepG2, and Hep3B), and GFP expression by $Ha_2bSm$-dE1/GFP came in second highest. It was also confirmed that the expression level was increased by $Ha_2bm$-dE1/GFP and $Ha_2bSm$-dE1/GFP under a hypoxic condition, rather than under a normoxic condition, not only in AFP-positive liver cancer cell lines (Huh7, HepG2, or Hep3B), but also in a liver cancer cell line (Hep1) that does not express AFP and a lung cancer cell line (A549). In contrast, it was confirmed that, in normal cells (HaCaT, see FIG. 6E), all vectors exhibited a very low GFP expression level. Thus, it was confirmed that the promoters constructed according to the present invention are cancer-specific promoters, and among the five candidate viruses, $Ha_2bm$-dE1/GFP is the most potent cancer-specific gene expression virus, and the following experiments were conducted.

Experimental Example 1-6

Confirmation of Regulation of Cancer-Specific Gene by Modified AFP Promoters in Liver Cancer Cell Tissue To confirm whether the adenoviruses constructed in Experimental Example 1-4 are able to regulate gene expression by the AFP promoters in a liver cancer-specific manner in cancer tissue, a tumor was formed using the liver cancer cell line Hep3B, and the adenovirus $a_2$bm-dE1/GFP or $Ha_2$bm-dE1/GFP was injected into the tumor and whether or not GFP expression occurred was observed by fluorescence.

To confirm whether the liver cancer-specific gene is expressed by the modified AFP promoters in liver cancer tissue, $1\times10^7$ Hep3B cells were injected subcutaneously into 6-week-old nude mice to form a tumor and, when the size of the tumor reached about 200 mm³, $5\times10^9$ VP of $a_2$bm-dE1/GFP or $Ha_2$bm-dE1/GFP was directly injected into the tumor three times at intervals of two days. After 3 days, the tumor was extracted and embedded in a paraffin block, which was then sectioned to a thickness of 3 μm and attached to a slide, and the resulting slide was sequentially immersed in xylene and a 100%, 95%, 80%, or 70% ethanol solution to be deparaffinized. The resulting tumor was immersed in a 0.5% NP40 solution to enhance tissue permeability, and then allowed to react with an anti-pimonidazole antibody (HP1-100, Chemicon, Temecula, CA, USA), which is used for labeling a hypoxic state, at 4° C. overnight to stain the hypoxic region red. The next day, the hypoxic region was hybridized with an Alexa 568-conjugated secondary antibody at room temperature for 2 hours and allowed to react again with an anti-GFP antibody (MAB3580, Chemicon, Temecula, CA, USA) at 4° C. overnight to stain the GFP protein green. The next day, the resulting product was allowed to react with an Alexa 448-conjugated secondary antibody at room temperature for 2 hours, stained with DAPI (cell nuclei were stained blue), mounted with a fluorescence-only mounting solution, and observed using a confocal laser microscope.

Figure 7:
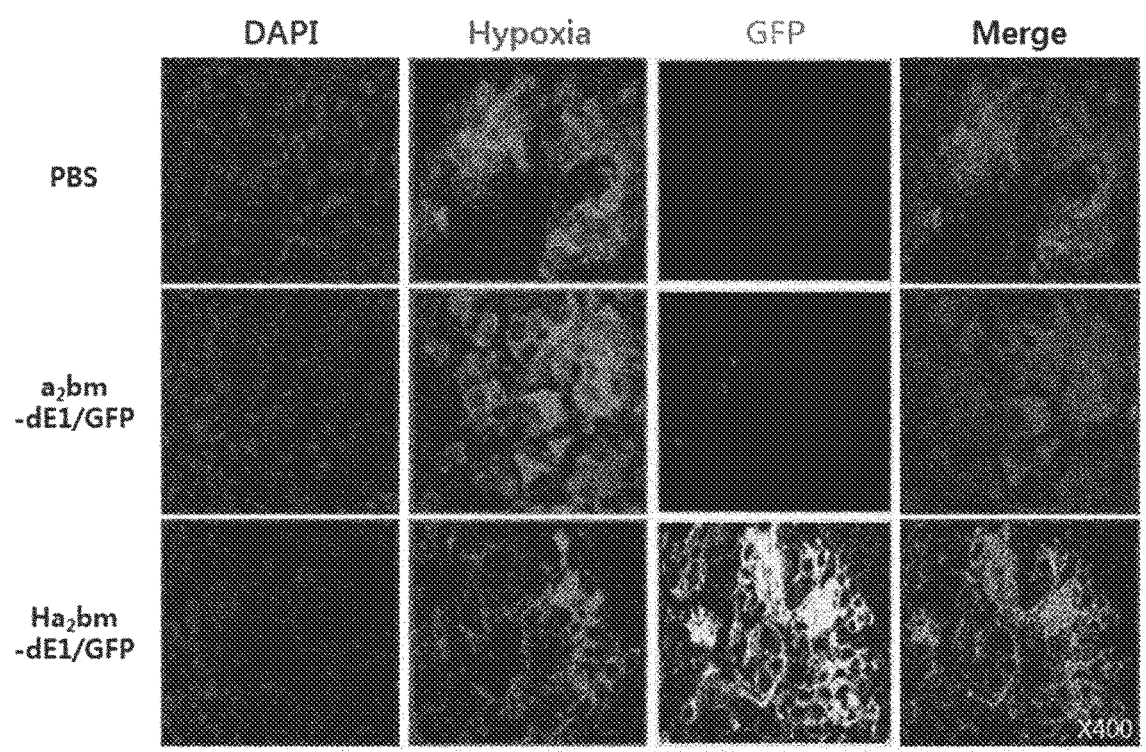
FIG. 7 illustrates the results of confirming, by fluorescence, the degree of GFP expression in tumor tissue of adenoviruses with liver cancer-specific promoters produced according to an embodiment of the present invention.

As illustrated in FIG. 7, it was confirmed that the adenovirus ($Ha_2$bm-dE1/GFP) in which the HRE-comprising promoter was loaded exhibited high gene expression in tumor cells, compared to the HRE-free promoter, and GFP expression was maintained due to the insertion of HRE not only in a normoxic region but also in a hypoxic region in the tumor.

Experimental Example 1-7

Construction of Liver Cancer-Specific Oncolytic Adenoviruses of which Replication is Regulated by Modified AFP Promoters Based on the research results obtained using the above-described non-replicable adenoviruses, $a_2$bm and $Ha_2$bm promoters with the highest efficiency and specificity were selected from among various types of promoters and used to construct liver cancer-specific oncolytic adenoviruses.

Figure 8:
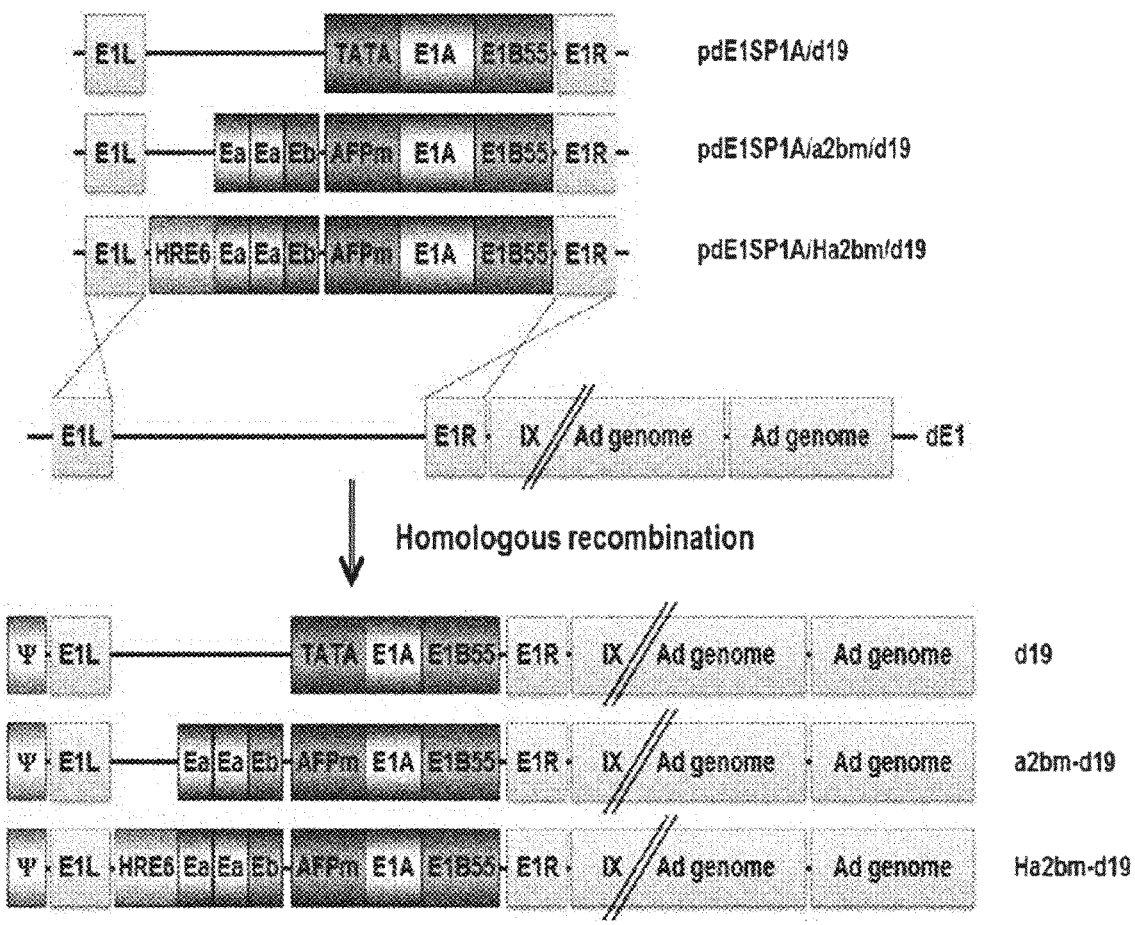
FIG. 8 illustrates the structures of liver cancer-specific oncolytic adenovirus shuttle vectors in which the replication of the adenoviruses is regulated by modified AFP promoters.

To construct liver cancer-targeting adenoviruses (HCC-targeting oAd vector), pΔE1sp1A/$a_2$bAFPm and pΔE1sp1A/$Ha_2$bAFPm vectors were cleaved with XhoI and BglII, and then the $a_2$bm and $Ha_2$bm promoters were respectively inserted into adenovirus shuttle vectors with an excellent cell-killing capacity due to the removal of E1B19Dka, thereby constructing pΔE1sp1A/$a_2$bAFPm/d19 and pΔE1sp1A/$Ha_2$bAFPm/d19 shuttle vectors (see FIG. 8).

Figure 9:
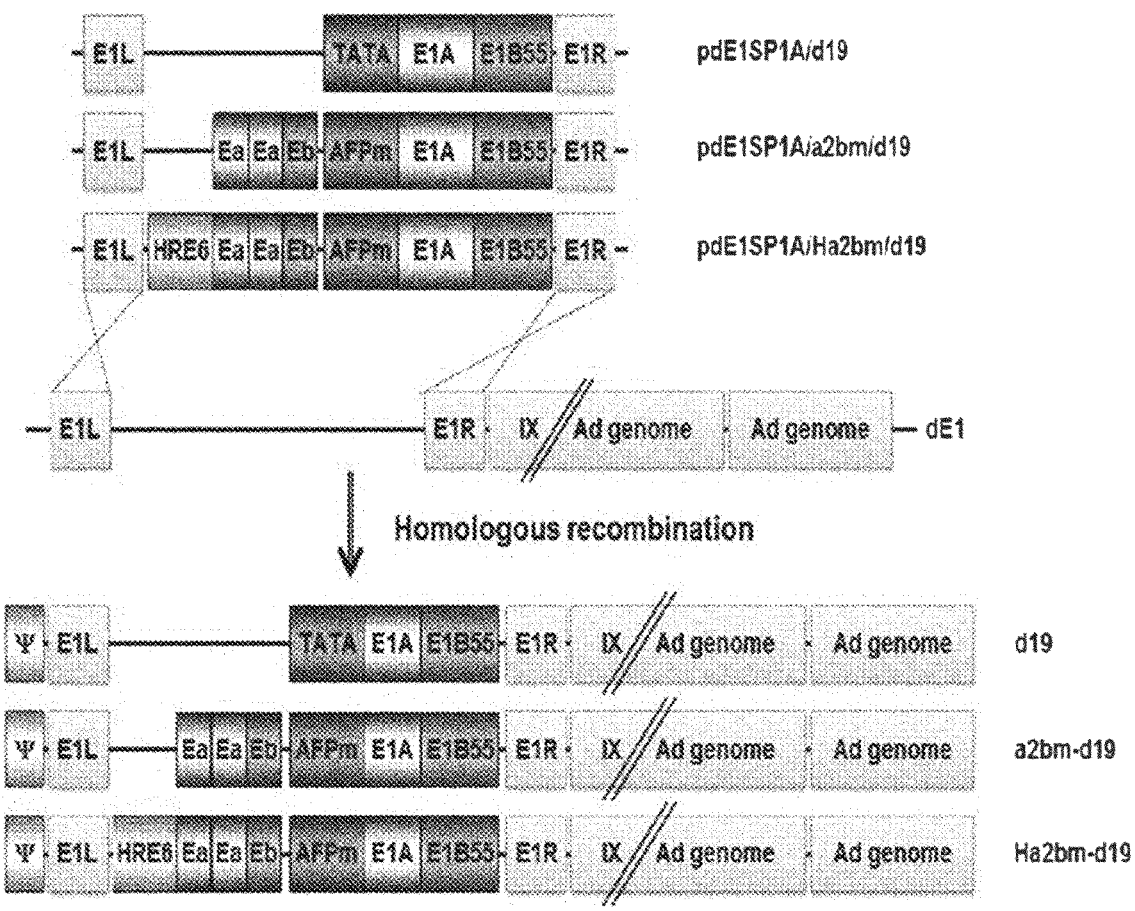
FIG. 9 illustrates the homologous recombination processes and structures of liver cancer-specific oncolytic adenoviruses in which the replication of the adenoviruses is regulated by modified AFP promoters.
Figure 10A:
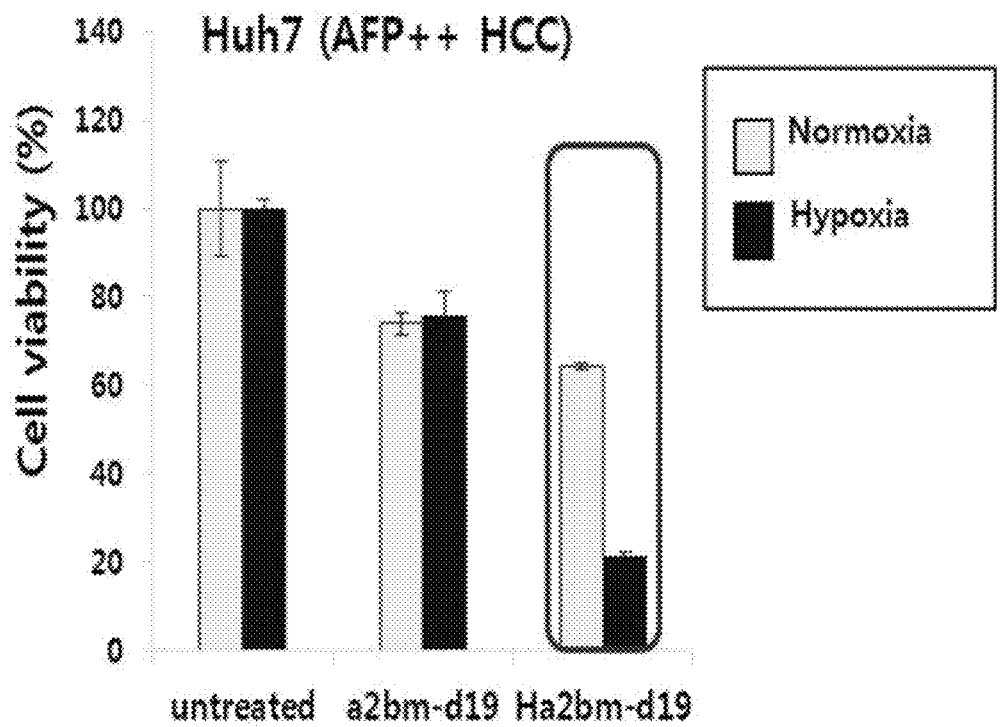
Figure 10B:
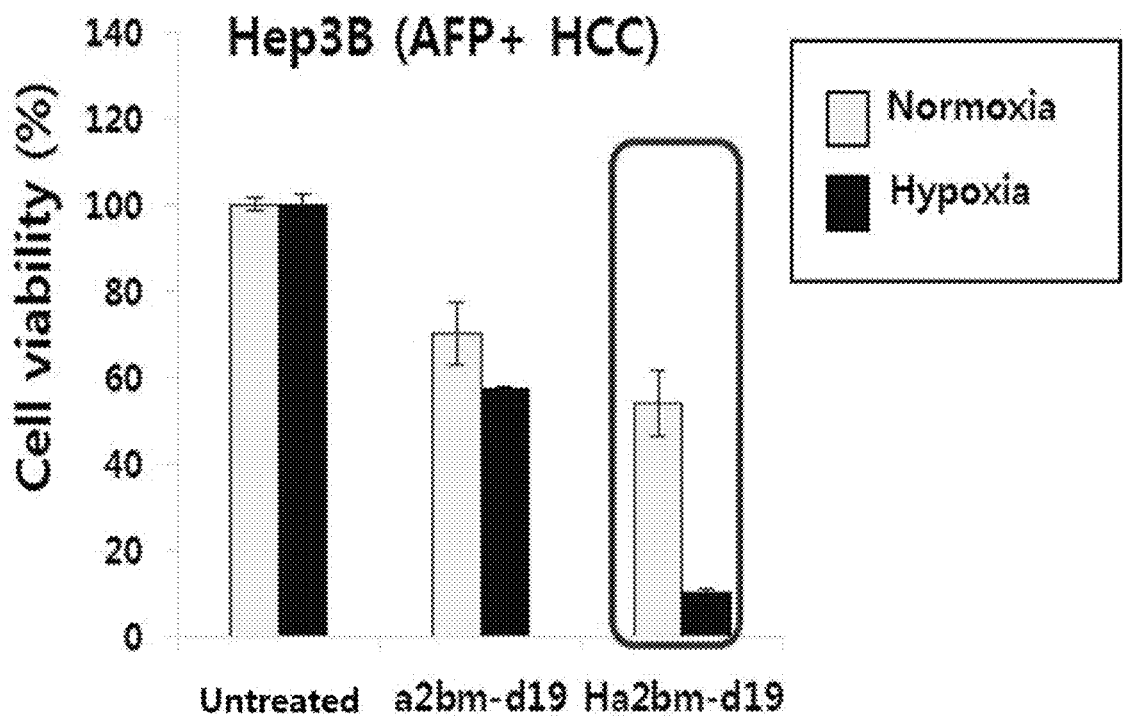
Figure 10C:
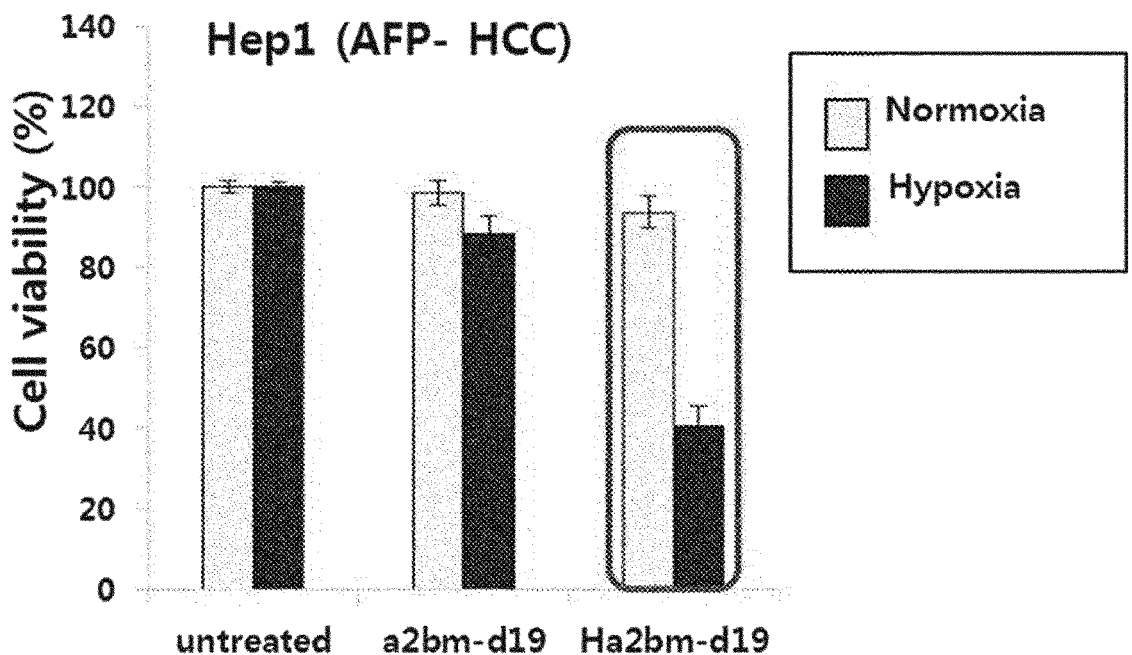
Figure 10D:
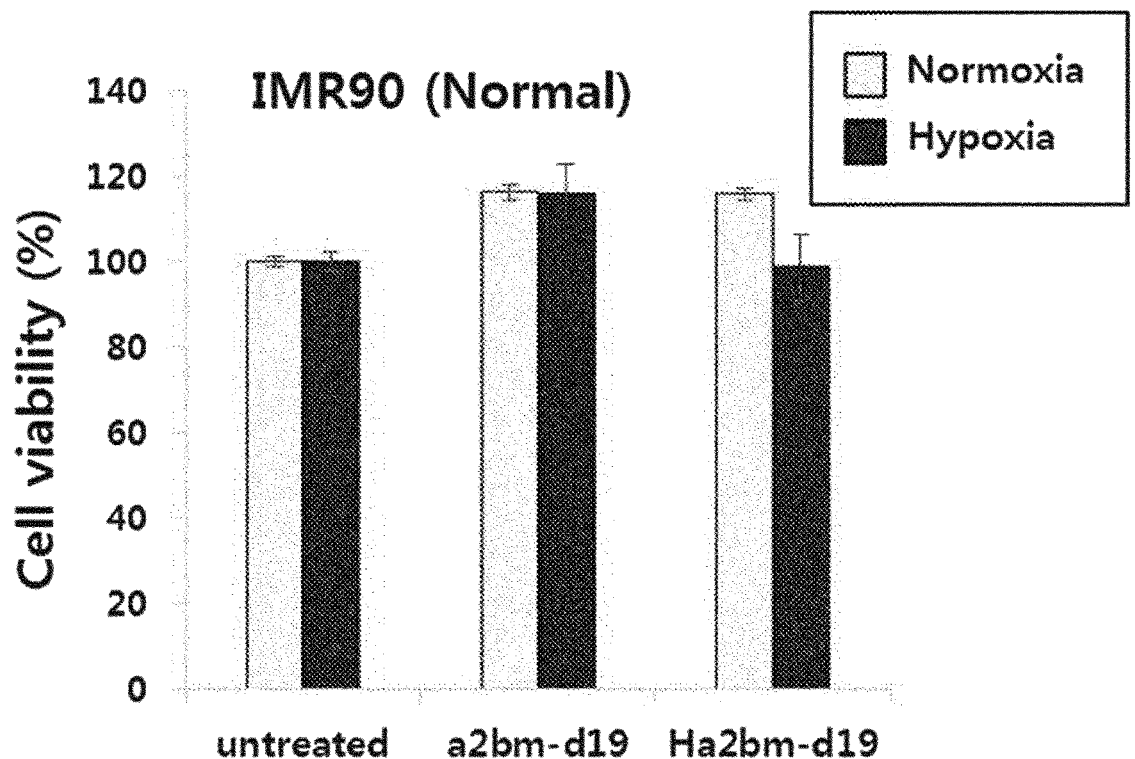
Figure 10E:
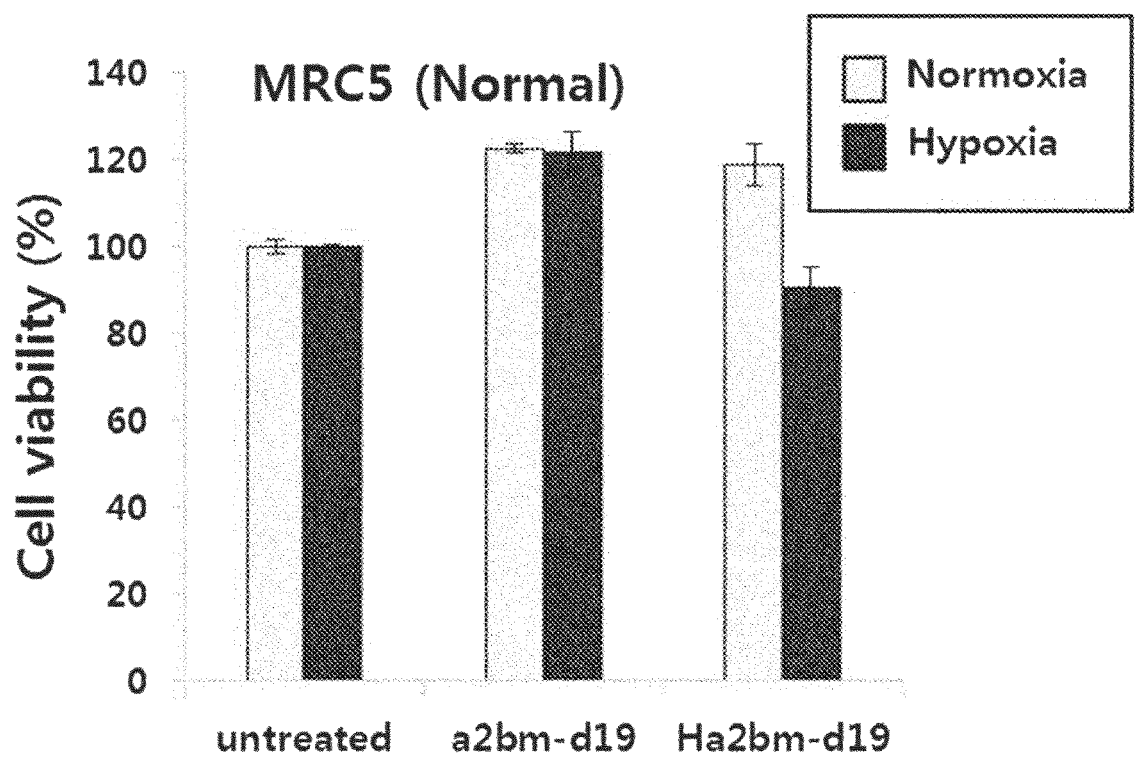

Next, the two shuttle vectors and a pΔE1sp1A/d19 shuttle vector as a control were cleaved with restriction enzyme XmnI to be linearized, and the adenovirus total vector dE1 was cleaved with restriction enzyme BetB I to be linearized, and then each shuttle vector and the total vector were transfected together into *E. coli* BJ5183 and subjected to E1 homogenous recombination, thereby finally constructing the control virus and two types of liver cancer-specific oncolytic adenoviruses, i.e., d19, $a_2$bm-d19, and $Ha_2$bm-d19 (see FIG. 9).

The produced plasmid DNAs were cleaved with restriction enzyme PacI to be linearized, followed by transfection of HEK293, which is an adenovirus-producing cell line, using Lipofectamine, thereby producing viruses. The HEK293 cell line was infected again with the produced adenoviruses, concentrated using a CsCl gradient method, and purely isolated, and then limiting dilution assay and optical density (O.D) by absorbance of the viral genome were used to determine the titers of the adenoviruses.

Experimental Example 1-8

Confirmation of Cell Killing Capacities of Liver Cancer-Specific Oncolytic Adenoviruses of which Replication is Regulated by Modified AFP Promoters To compare liver cancer-specific cell killing capacities by the adenoviruses constructed in Experimental Example 1-7, various cell lines (Huh7, Hep3B, Hep1, IMR90, and MRC5) were infected with the d19, $a_2$bm-d19, or $Ha_2$bm-d19 adenovirus, respectively, and then MTT assay was performed.

As illustrated in FIGS. 10A, 10B, 10C, 10D, and 10E, it was confirmed that the cell killing capacity of the d19 adenovirus was highly shown in all cells used in the experiment, i.e., cancer cells (Huh7, Hep3B, Hep1) and normal cells (IMR90, MRC5). However, in the case of infection with the $a_2$bm-d19 adenovirus, a cell killing capacity was shown only in the cell line cells with a high AFP expression level, and particularly, the cell viability of the IMR90 and MRC5, which are normal cells, was almost similar or higher than that of a non-treated cell group. In addition, when infected with the $Ha_2$bm-d19 adenovirus, in which HRE was additionally inserted, the cell killing capacity in AFP-expressing cells was remarkably increased under a hypoxic condition. In particular, in the Hep3B cell line was exhibited a cell killing capacity that is similar to that of the d19 adenovirus with a potent cell killing capacity. However, in the normal cell lines such as IMR90 and MRC5 was exhibited cell viability that is similar to that of an experimental group not treated with a virus, from which it was confirmed that the adenoviruses with modified AFP promoters according to the present invention had a cell killing capacity in a liver cancer-specific manner. In the Hep1 cell line, which does not express AFP, was exhibited an increased cell killing capacity of about 60% under a hypoxic condition when infected with the $Ha_2$bm-d19 adenovirus, from which it was expected that the adenovirus can kill not only AFP-expressing cancer cells, but also cancer cells that do not express AFP in liver cancer tissue with high heterogeneity, and thus has a more potent oncolytic effect.

Experimental Example 1-9

Confirmation of Viral Replication Ability of Liver Cancer-Specific Oncolytic Adenoviruses of which Replication is Regulated by Modified AFP Promoters To confirm whether the phenomenon, in which the adenoviruses of the present invention exhibited a significantly enhanced cell killing capacity in a hypoxia state, is correlated with an increase in viral replication ability, the liver cancer cell line Hep3B and the lung cancer cell line A549 were infected with a$_2$bm-d19 or Ha$_2$bm-d19 adenoviruses, respectively, and then a cell culture solution and living cells were all collected and the cell line HEK293 was re-infected therewith to perform limiting dilution assay.

Figure 11:
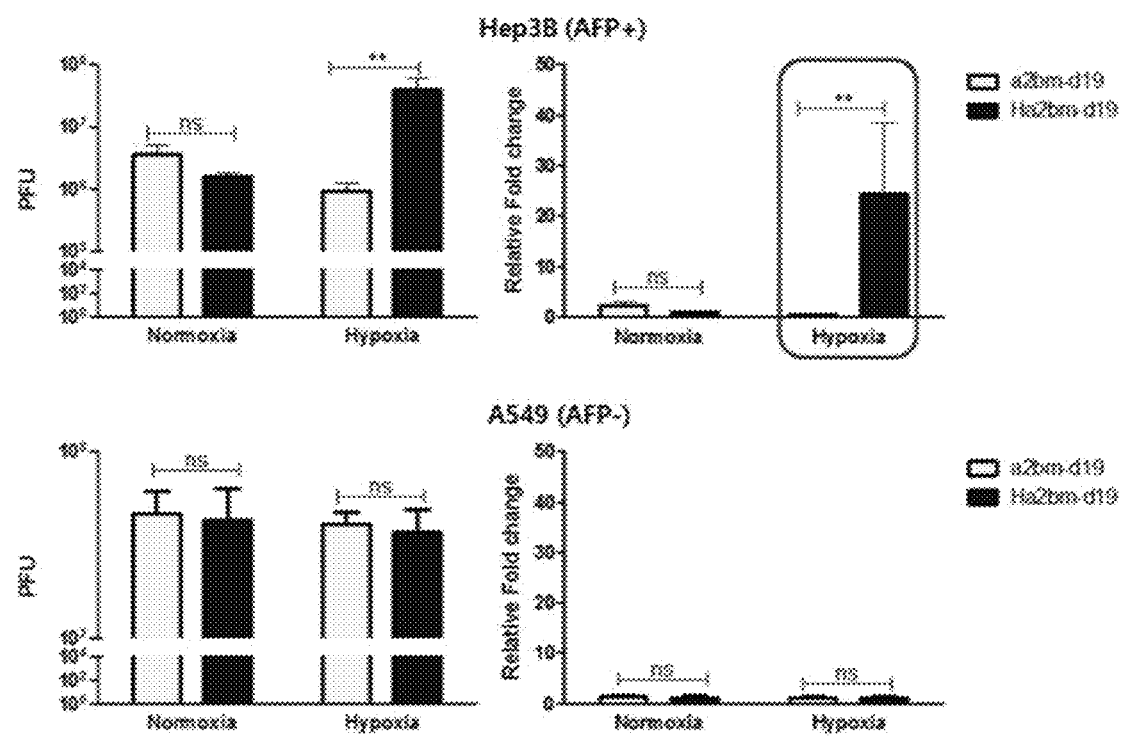
FIG. 11 illustrates the results of confirming the replication capabilities of recombinant adenoviruses with liver cancer-specific promoters constructed according to an embodiment of the present invention under normoxic and hypoxic conditions.

As illustrated in FIG. 11, it was confirmed that there was no difference between the replication abilities of the a$_2$bm-d19 and Ha$_2$bm-d19 adenoviruses in the lung cancer cell line, whereas the replication of the virus was not inhibited even in a hypoxia state in the Hep3B cell line infected with the Ha$_2$bm-d19 adenovirus and was rather increased 40-fold, compared to a normoxia condition and cells infected with the a$_2$bm-d19 virus.

Experimental Example 1-10

Verification of Replication Abilities of Liver Cancer-Specific Oncolytic Adenoviruses in Spheroids To allow a hypoxic region to be naturally formed inside cancer tissue in vitro, the liver cancer cell line Hep3B was injected into a nude mouse to form a tumor, and the tumor was extracted to perform spheroid culture. Spheroid sections obtained by infection with two types of adenoviruses a$_2$bm-d19 or Ha$_2$bm-d19 during the spheroid culture were subjected to a tissue immunostaining method using antibodies against the E1A protein related to the replication of an adenovirus.

Figure 12:
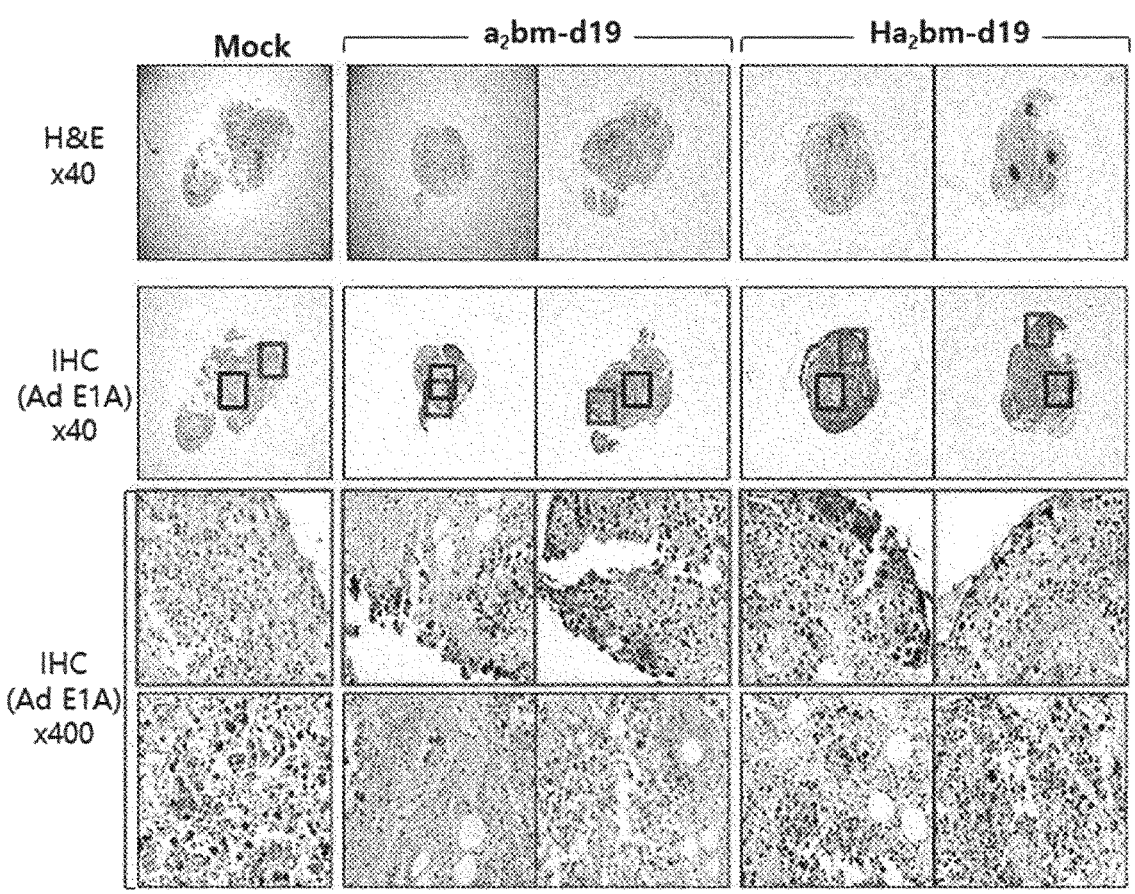
FIG. 12 illustrates the results of confirming, through fluorescence staining in spheroid-cultured liver cancer tissue (Hep3B organoid system), the replication capabilities of recombinant adenoviruses with liver cancer-specific promoters constructed according to an embodiment of the present invention at a normoxia concentration (tumor peripheral regions; normoxia, red boxes) and at a hypoxia concentration (tumor central regions; hypoxia, blue boxes).

As a result, as illustrated in FIG. 12, E1A was observed only in a spheroid margin, which is expected to be a normoxia region where the virus is easily accessible, in tissue infected with a$_2$bm-d19, whereas, in tissue infected with Ha$_2$bm-d19, the E1A protein was observed not only in the spheroid margin but also inside tissue, which is expected that a hypoxia condition was naturally formed. This suggests that the replication ability of Ha$_2$bm-d19, which is a cancer-specific oncolytic adenovirus, is not inhibited not only in vitro but also in a hypoxia condition in vivo.

Experimental Example 1-11

Verification of In Vivo Replication Abilities and Cell Killing Abilities of Liver Cancer-Specific Oncolytic Adenoviruses To verify the in vivo cell killing abilities and replication abilities of liver cancer-specific oncolytic adenoviruses on the basis of the in-vitro experimental results, the Hep3B cell line was injected subcutaneously into nude mice to form tumors, and PBS, adenovirus a$_2$bm-d19, or adenovirus Ha$_2$bm-d19 was respectively administered to the tumors. Using this, the expression pattern of the E1A protein, which is related to the replication of an adenovirus in tumor tissue, was examined and the degrees of cell killing were compared through TUNEL assay.

Figure 13:
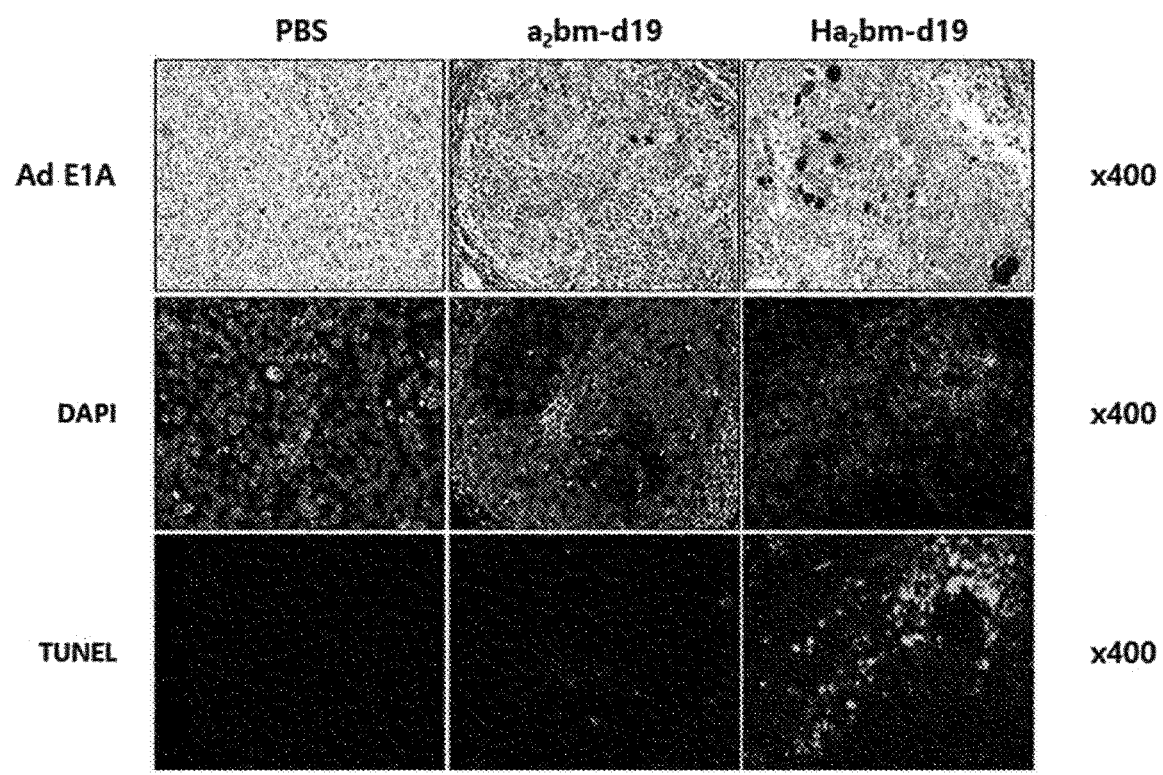
FIG. 13 illustrates the results of confirming the proliferative capabilities and antitumor effects (necrocytosis) of recombinant adenoviruses with liver cancer-specific promoters constructed according to an embodiment of the present invention in a liver cancer subcutaneous xenograft model (AFP+ Hep3B xenograft model).

As illustrated in FIG. 13, as a result of performing immunostaining using antibodies against the E1A protein of an adenovirus, a significant increase in expression of the E1A protein was observed in the experimental group treated with HRE-inserted Ha$_2$bm-d19, compared to the experimental group treated with a$_2$bm-d19, and it was observed that E1A was uniformly distributed over a wide area of the tumor tissue of the Ha$_2$bm-d19-treated group. From the TUNEL assay results, it was observed that, like E1A, TUNEL-positive cells where necrocytosis had been progressed were uniformly distributed inside tumor tissue in the experimental group treated with HRE-inserted Ha$_2$bm-d19. Through this, it was confirmed that HRE-inserted Ha$_2$bm-d19 exhibited an excellent cell killing effect without inhibition of the replication ability thereof even in a hypoxic condition in tumor tissue, compared to HRE-free Ha$_2$bm-d19.

Experimental Example 1-12

Verification of In Vivo Antitumor Effects of Liver Cancer-Specific Replicable Adenoviruses Using Orthotopic Model 6-week-old male nude mice (BALB/c-nu) were purchased from Orient Inc., Korea to conduct animal experiments. The temperature and humidity of an animal breeding room were maintained at 22±2° C. and 55-60%, respectively, light/dark cycles were adjusted to 12 hours, and the animals were allowed to freely eat solid feed (Central Lab Animal Inc., Seoul, Korea) sterilized with radiation and freely drink sterilized water.

To establish an orthotopic model, which is the closest to an actual tumorigenic model, the abdominal subcutaneous tissues of 6-week-old male nude mice were incised, 1×10$^6$ Hep3B cells suspended with 20 µl of HBSS and stably expressing luciferase were mixed with 20 µl of Matrigel (BD Bioscience, San Jose, CA, USA), the mixture was directly injected into the left hepatic lobe, and the incision was sutured. 2 weeks after cell injection, blood was collected from the mice, serum was separated, and then an AFP ELISA kit (R&D Systems, Minneapolis, MN, USA) was used to measure the level of AFP expression in the blood, and the mice having an AFP expression level of 700 ng/mL or more were divided into three groups and used for the experiment. 2.5×10$^{10}$ VP of PBS or each of the two types of adenovirus (a$_2$bm-d19 and Ha$_2$bm-d19) was intravenously injected three times at intervals of two days into the tail of each mouse, and 200 mg/kg of luciferin (Promega, Madison, WI, USA) was intraperitoneally administered to each mouse at intervals of 1 week, followed by optical imaging using IVIS 100 (Xenogen, Alameda, CA, USA). Signals obtained through imaging were quantitatively analyzed using the IGOR-PRO Living Image software (Xenogen, Alameda, CA, USA). 5 weeks after virus injection, blood was collected, serum was separated, the level of AFP expression in the blood was measured by ELISA, liver cancer tissue was extracted and weighed, and then embedded in paraffin blocks. PBS, a$_2$bm-d19, or Ha$_2$bm-d19 was respectively injected intravenously, and then optical imaging was performed every week to confirm antitumor effects.

Figure 5:
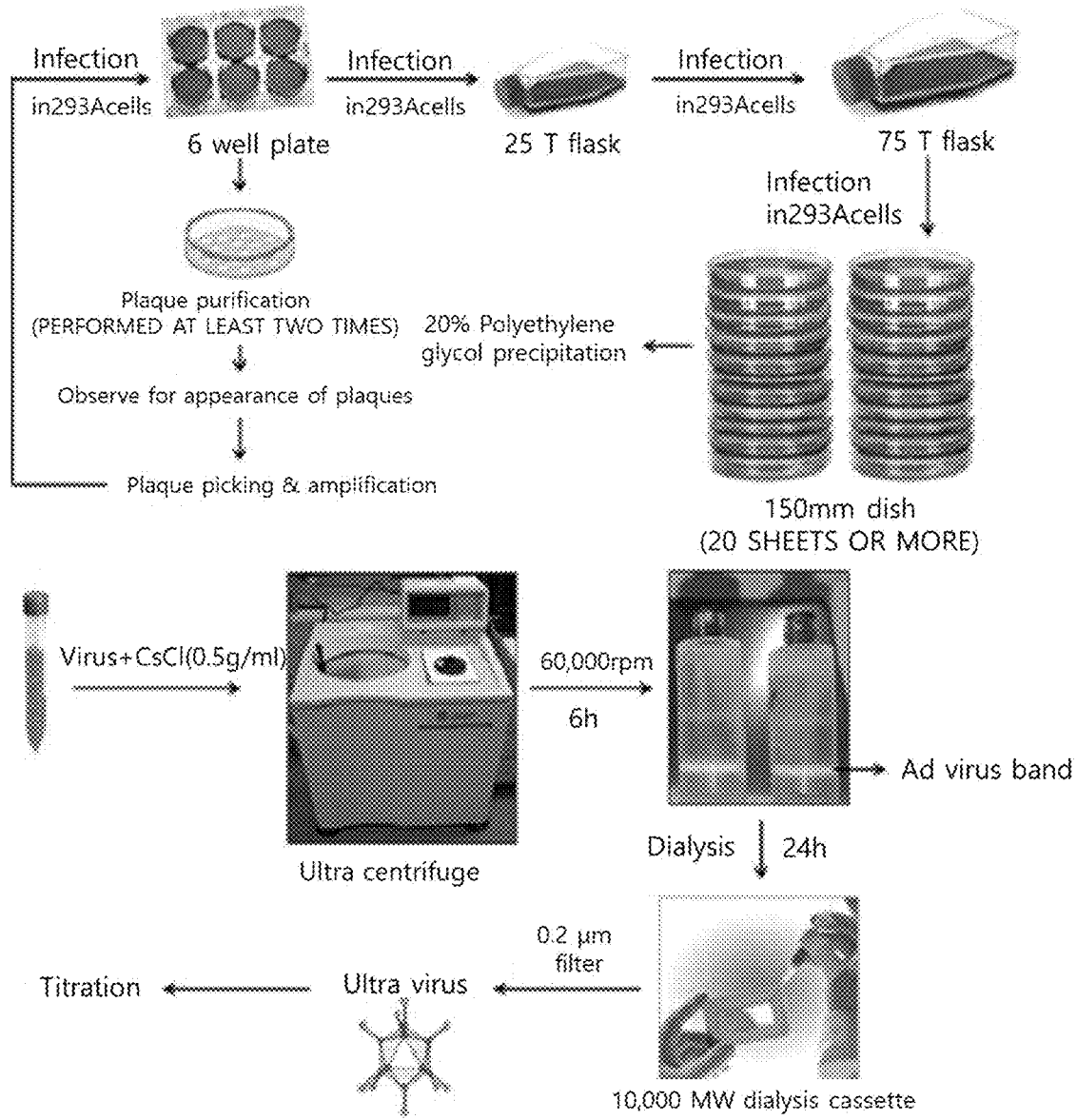
FIG. 5 illustrates a process of constructing an adenovirus in which gene expression is regulated by a modified AFP promoter according to an embodiment of the present invention.
Figure 6A:
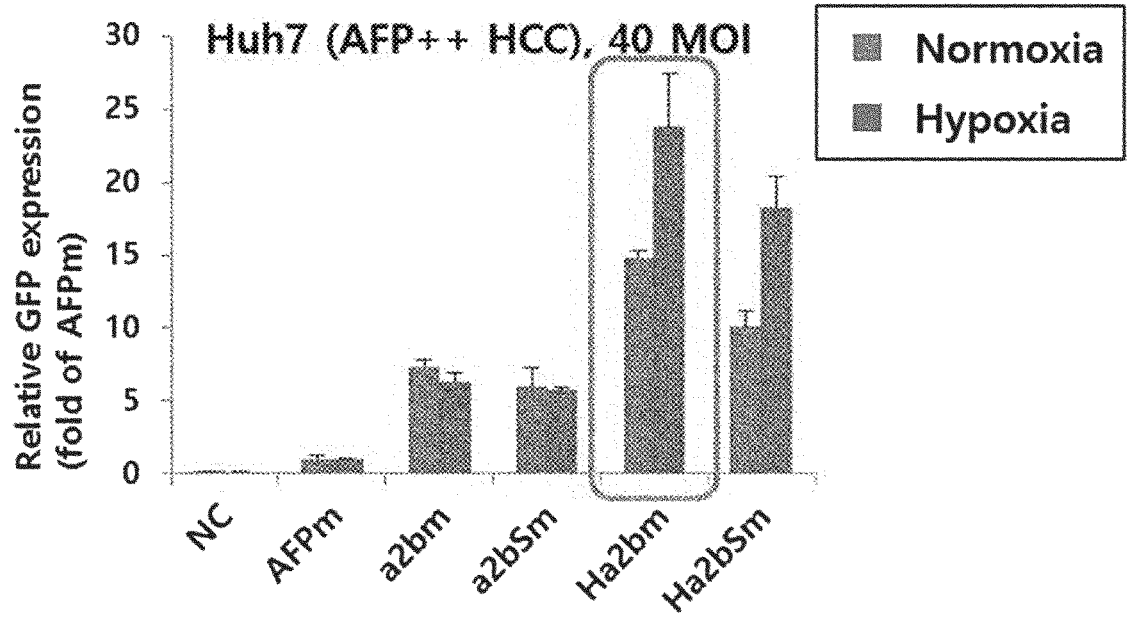
FIGS. 6A, 6B, 6C, 6D, 6E, and 6F are graphs showing the results of confirming the presence or absence of the gene expression activities of recombinant adenoviruses with liver cancer-specific promoters loaded therein and produced according to an embodiment of the present invention, depending on cell lines, and of confirming an increase in gene expression thereof in a hypoxia state.
Figure 6B:
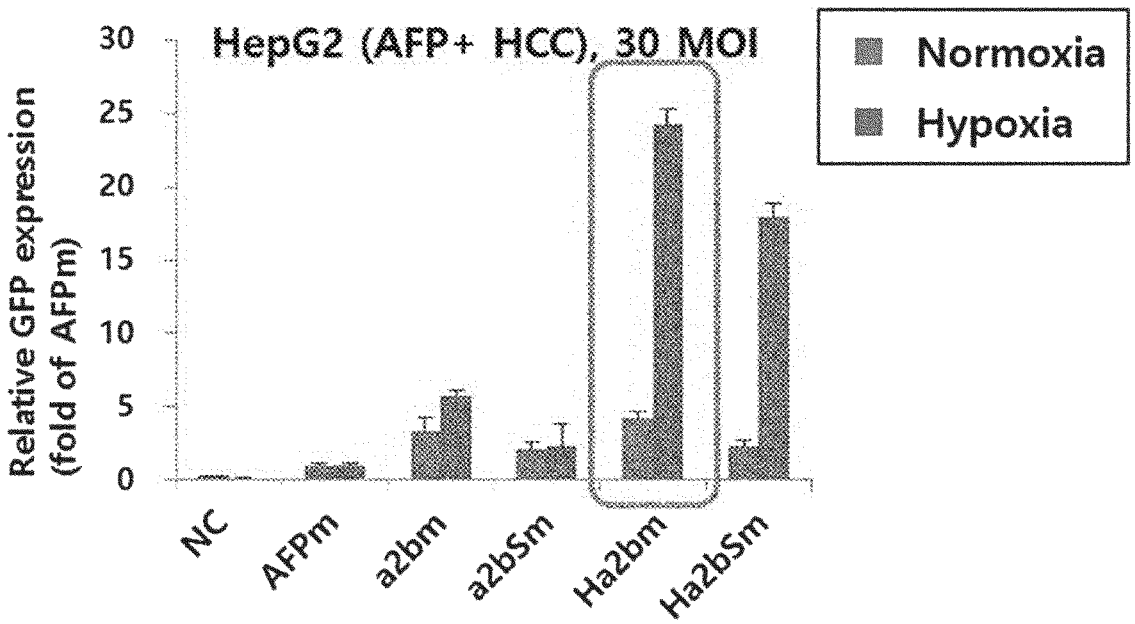
Figure 6C:
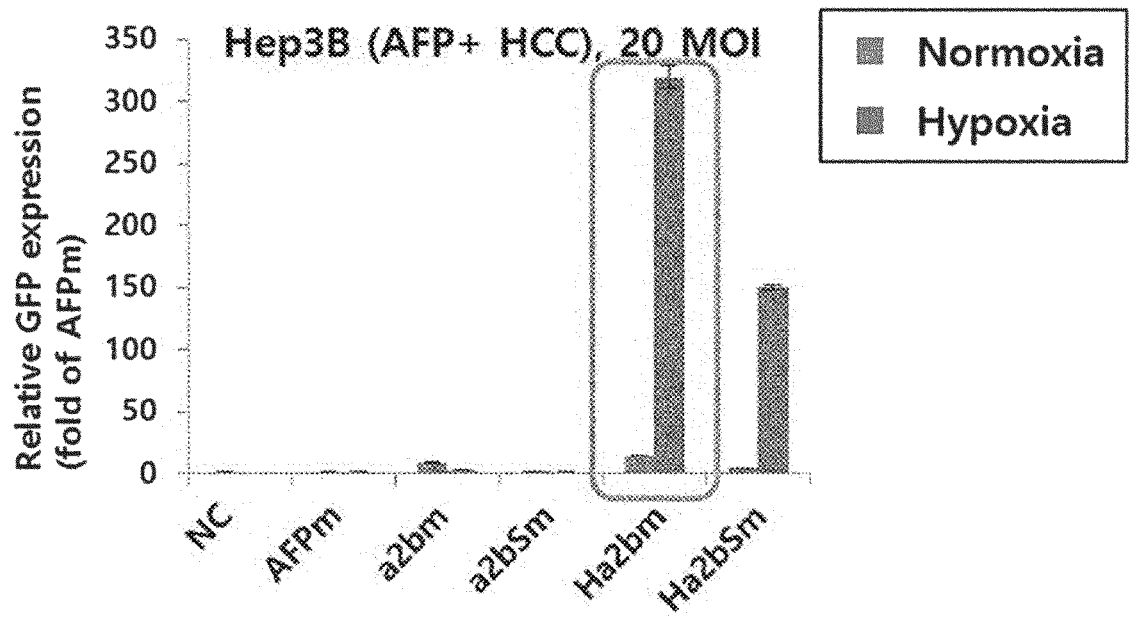
Figure 6D:
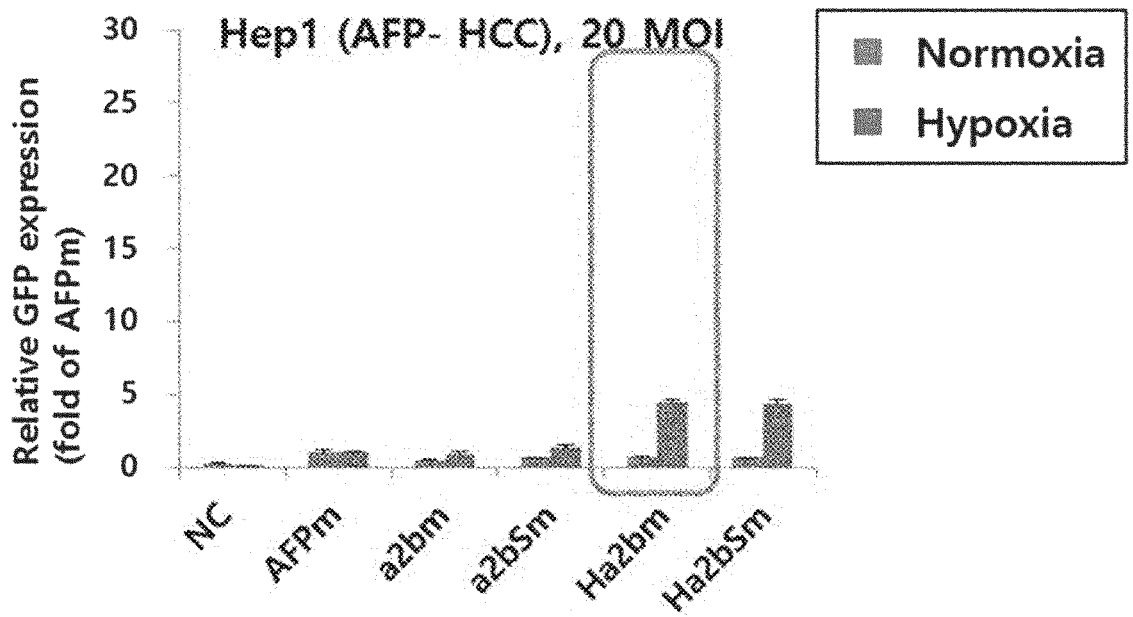
Figure 6E:
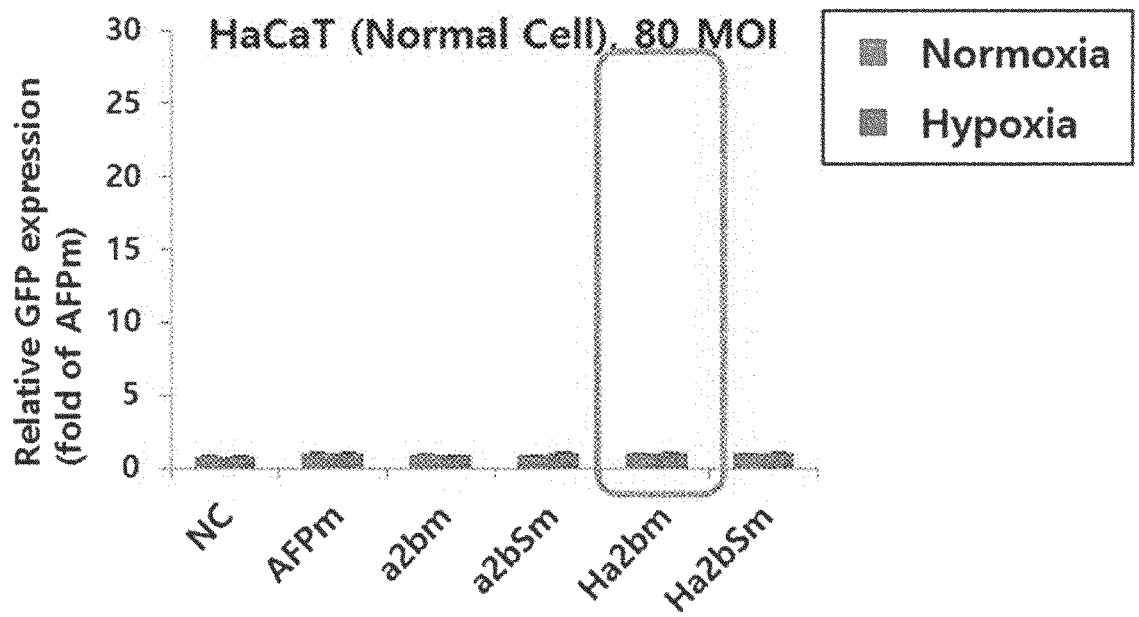
Figure 6F:
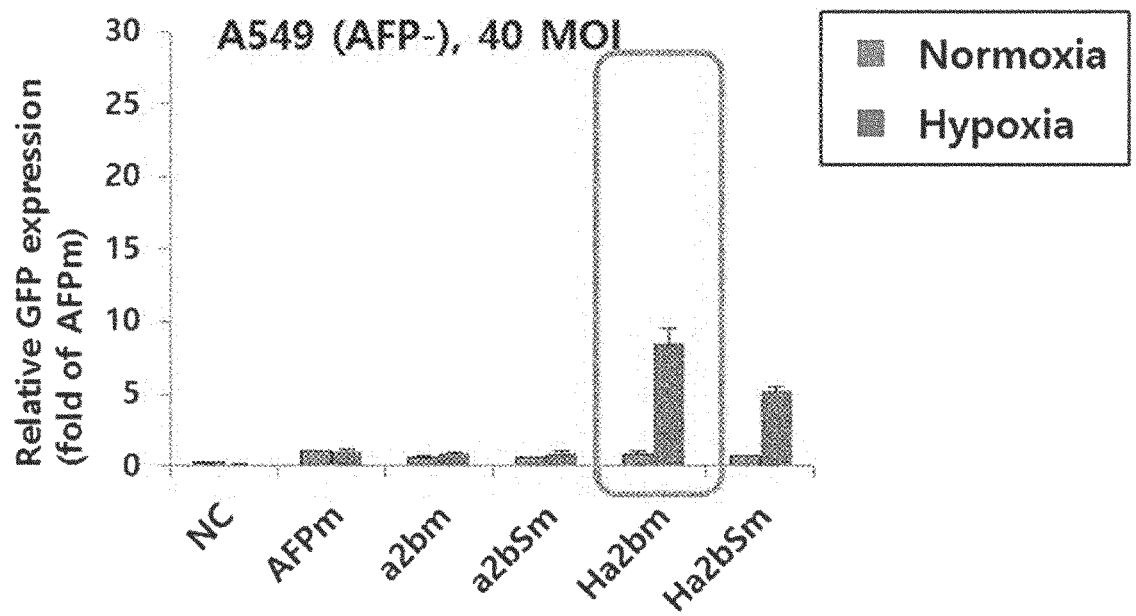
Figure 14:
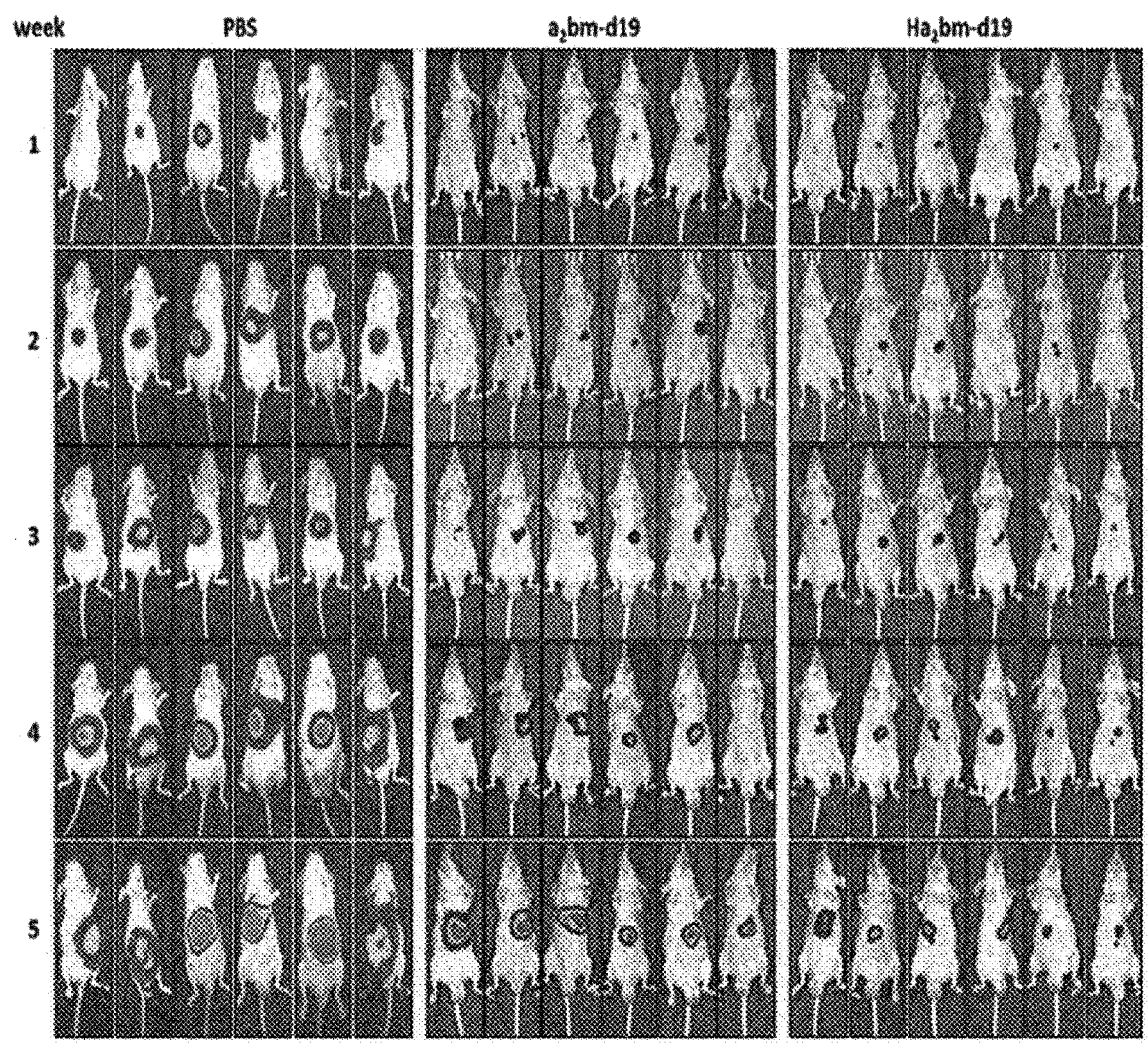
FIG. 14 illustrates the results of confirming the antitumor effects of recombinant adenoviruses with liver cancer-specific promoters constructed according to an embodiment of the present invention in a liver cancer orthotopic xenograft model.
Figure 15:
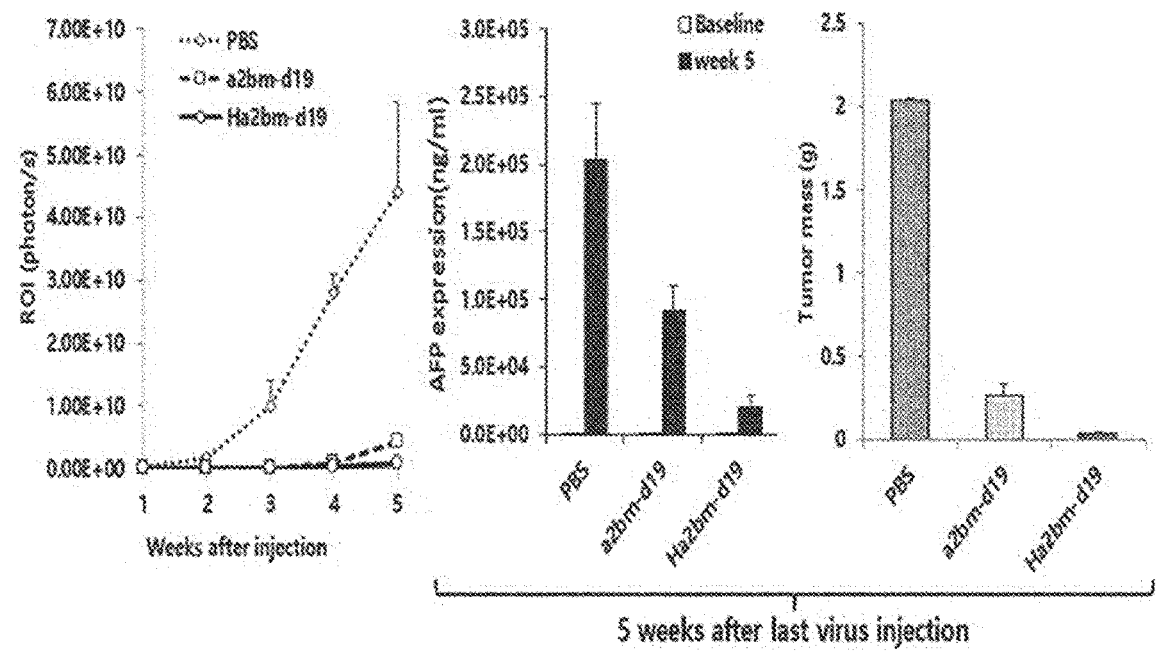
FIG. 15 is a set of graphs showing the results of confirming the antitumor effects of recombinant adenoviruses with liver cancer-specific promoters constructed according to an embodiment of the present invention.

As illustrated in FIGS. 14 and 15, 5 weeks after the adenoviruses were injected, the three groups showed the most significant difference in antitumor effect. In the case of the a$_2$bm-d19-administered group, it was confirmed that all six mice showed a continuously great increase in the size of a tumor. In contrast, it was confirmed that, in the case of the Ha$_2$bm-d19-administered group, the growth rate of a tumor was reduced in most mice, and it was consequently confirmed that, 5 weeks after virus administration, the size of a tumor was smaller in the Ha$_2$bm-d19-administered group than in the a$_2$bm-d19-administered group. As a result of quantifying changes in tumor size using a total flux value, 5 weeks after virus administration, the Ha$_2$bm-d19-administered group exhibited a 5-fold lower value compared to that of the a$_2$bm-d19-administered group. This means a tumor growth inhibitory effect of about 82%, from which it was confirmed that the administration of Ha$_2$bm-d19 provides an excellent antitumor effect. In addition, as a result of comparing the levels of AFP expression in serum (5 weeks after virus administration) together with images to confirm antitumor effects by the liver cancer-specific oncolytic adenoviruses, like the total flux value, the Ha₂bm-d19-administered group expressed a 5-fold lower concentration of AFP than that of the a₂bm-d19-administered group.

Example 2

Production of Stem Cells for Loading Liver Cancer-Specific Oncolytic Adenoviruses Experimental Example 2-1

Optimization of Loading Efficiency of Adenovirus into MSC

To confirm the transduction efficiency of adenoviruses into mesenchymal stem cells (MSCs, Pharmicell Corporation), the mesenchymal stem cells (MSCs, Pharmicell Corporation) were infected with, at an MOI of 0-200, each of three types of viruses, dE1/LacZ, dEl-k35/LacZ, and dEl-RGD/LacZ in which LacZ gene-expressing fibers are different from one another, and after two days, LacZ expression was confirmed through X-gal staining.

Figure 16A:
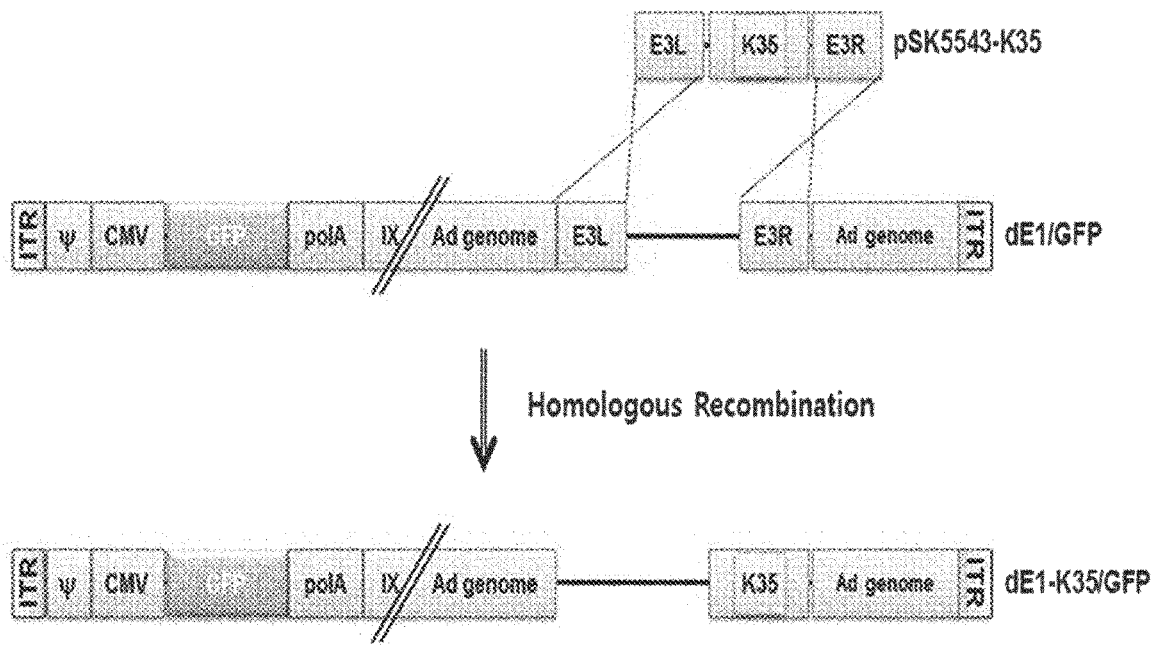
FIG. 16A illustrates a method of constructing a non-replicable adenovirus expressing an adenovirus serotype 35 fiber (K35).
Figure 16B:
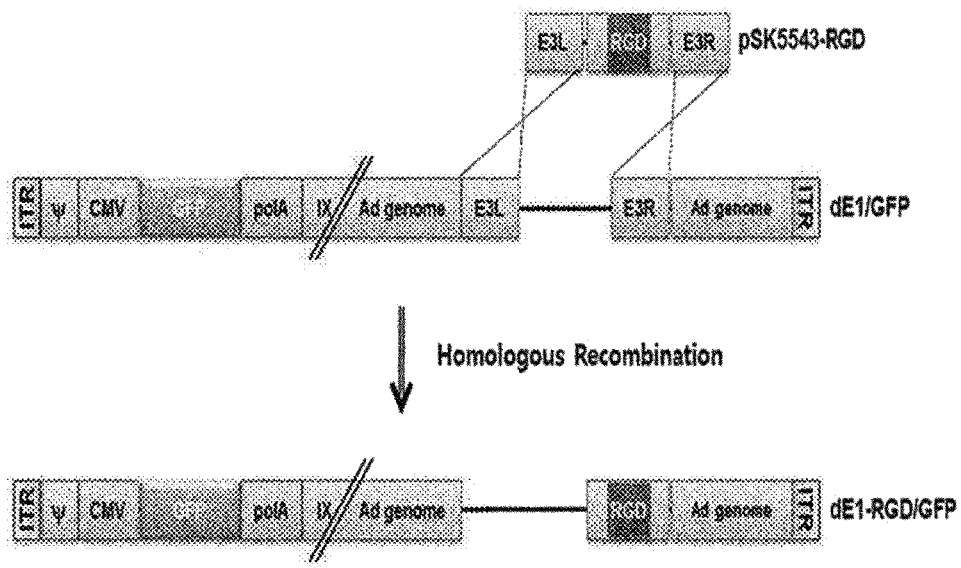
FIG. 16B illustrates a method of constructing a non-replicable adenovirus expressing RGD at an adenovirus fiber terminal end.

Each of the fiber-modified adenoviruses was constructed according to the following method.

pSK5543-K35, which is an adenovirus shuttle vector into which the adenovirus type 35 (serotype 35) fiber sequence of SEQ ID NO: 1 was inserted, and dE1/GFP, which is a non-replicable adenovirus in which the GFP gene was inserted into the adenovirus E1 region, were subjected to homogenous recombination, thereby constructing a dE1-35/GFP virus (see FIG. 16A). In addition, pSK5543-RGD, which is an adenovirus shuttle vector in which RGD was inserted into the fiber end of the adenovirus, and dE1/GFP, which is a non-replicable adenovirus in which the GFP gene was inserted into the adenovirus E1 region, were subjected to homogenous recombination, thereby constructing a dE1-RGD/GFP virus (see FIG. 16B). The constructed adenoviruses were infected into the HEK293 cell line and mass-proliferated, thereby producing adenoviruses.

Figure 16C:
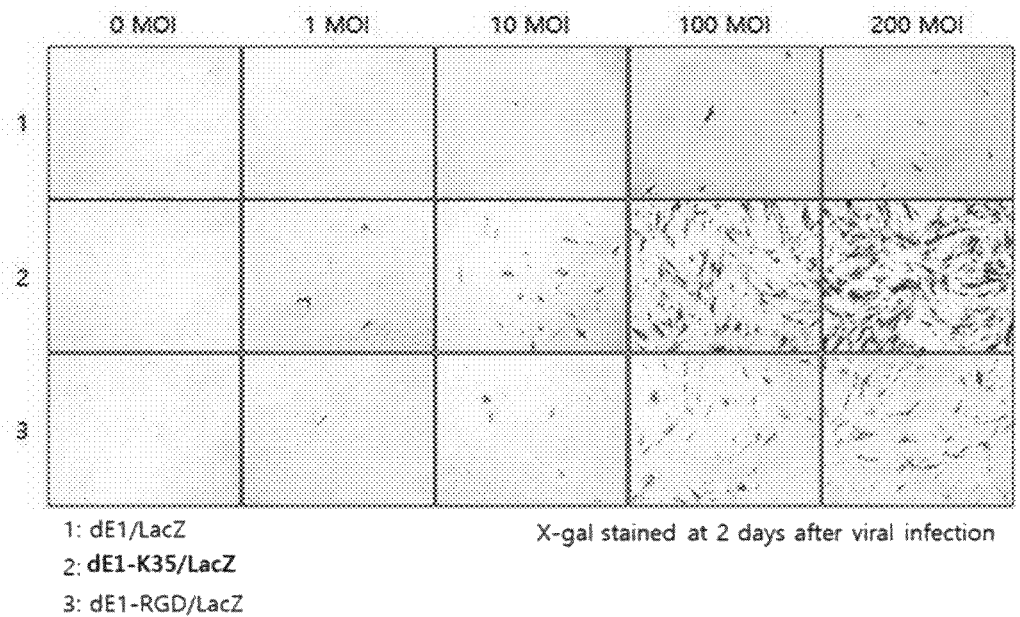
FIG. 16C illustrates the results of confirming the transduction efficiency into mesenchymal stem cells according to adenovirus fiber modification.

As illustrated in FIG. 16C, when MSCs were infected with the dEl-k35/LacZ virus, the highest gene transduction efficiency was exhibited.

In addition, to optimize the transduction efficiency of Ad into MSCs, the transduction efficiency was examined using GFP-expressing Ad5 having different fiber types: dE1/GFP (Ad5 vector having wild-type fiber), dEl-k35/GFP (chimeric Ad5 having Ad serotype 35 fiber knob), dEl-RGD/GFP (Ad5 vector comprising an RGD motif in the HI loop of the Ad fiber), dEl-k3S/GFP (chimeric Ad5 comprising an Ad5 cleaved fiber shaft and an Ad3 fiber knob), dE1-VSVG (12L)/GFP, dE1-VSVG(12C)/GFP, and dE1-VSVG(12R)/GFP. Before gene delivery, MSCs were inoculated into a 24-well plate at a density of 5×10⁴ cells/well for 24 hours. The MSC cells were treated with each Ad at 0, 5, 20, or 100 MOI, and incubated at 37° C. for 48 hours. GFP expression was measured using a fluorescent microscope (Olympus IX81; Olympus Optical, Tokyo, Japan).

As illustrated in FIG. 17, dE1/GFP and dE1-RGD/GFP exhibited significantly very low transduction efficiency into MSCs at all multiplicities of infection (MOI). dE1-k3S/GFP exhibited a higher GFP expression level in a dose-dependent manner, while exhibiting significantly very low efficiency. However, dEl-k35/GFP exhibited very high transduction efficiency into MSCs. This coincided with the results of LacZ expression. In particular, it was confirmed that the adenovirus having the Ad serotype 35 fiber knob of SEQ ID NO: 1 was well infected into mesenchymal stem cells even at 5 MOI, and thus had a significantly excellent effect as an adenovirus for loading into mesenchymal stem cells. Subsequently, the viral vector comprising the fiber sequence of SEQ ID NO: 1 was used to conduct experiments. 2-2. Verification of Cell Killing Ability and Virus Replication Ability of MSCs by Adenovirus in MSCs MSCs were infected with an oncolytic adenovirus (H5cmT-Rd19-k35/Luc) at the titer of 0.02, 0.05, 0.1, 0.2, 0.5, or 1 MOI, and the cell killing capacity thereof was confirmed through MTT assay. In addition, to confirm the amount of virus produced in the MSCs, virus replication capacity was confirmed through Q-PCR.

H5cmT-Rd19 was constructed as follows.

To construct an adenovirus comprising 6 copies of HRE enhancer (SEQ ID NO: 6) and in which the expression of the E1A gene is regulated by a 5MMTERT promoter, first, the Rb7Δ19/E1B55 region was amplified by polymerase chain reaction (PCR) using the total adenovirus gene as a template to obtain a desired gene site. 5'-GCGGAATTCACTCTT-GAGTGCCAGCGAGTA-3' as a sense primer and 5'-CGCGGATCCACATTTCAGTACCTCAATCTG-3' as an antisense primer were used, and for convenience in cloning, EcoRI and BamHI restriction enzyme sites were inserted. The resulting PCR product was cleaved with EcoRI and BamHI, and then inserted into a pBluescript II SK(+) vector, and a vector comprising a 5MMTERT promoter constructed in the laboratory was cleaved with ClaI and EcoRI, and then inserted thereinto. Finally, the previously constructed vector pBluescript II SK(+)/5MMTERT/Rb7Δ19 was cleaved with XhoI and SalI and 6 copies of the HRE sequence were inserted into the vector pBluescript II SK(+)/5MMTERT/Rb7Δ19. The recombinant enhancer and promoter were cleaved, with XhoI and BamHI, from the resulting vector pBluescriptSK(+)/HRE65MMTERT/Rb7Δ19 and inserted into the E1 shuttle vector pΔE1sp1B. The E1 shuttle vector constructed using the above method was cleaved with restriction enzyme XmnI, and then simultaneously transfected into E. coli BJ5183 along with the adenovirus dl324BstB which had become single-stranded through treatment with restriction enzyme BstB, thereby inducing genetic homologous recombination. The recombinant plasmid DNA obtained in BJ5183 was transfected again into E. coli DH5α to amplify DNA. The homologous recombinant plasmid DNA was obtained from E. coli DH5α and treated with restriction enzyme HindIII to screen respective adenovirus genomes. The knob site of the virus using the H5cmT-Rd19 as a backbone was substituted with a k35 sequence (SEQ ID NO: 1), and for imaging, the Luc gene was inserted thereinto and used.

As illustrated in FIG. 18, it was confirmed that the cell killing ability and virus proliferation ability of the pan-cancer-specific oncolytic adenovirus were increased depending on infection time or concentration. Based on the above results, it was confirmed that, when MSCs are used as a cell therapy carrier, the replication of a virus with cell killing efficacy can induce more killing of cancer cells, and thus the MSCs have a further enhanced anticancer effect compared to the case of using other carriers. It was also confirmed that, after a certain period of time after being injected into the body, the MSCs were removed by the adenovirus, thus alleviating concerns about the retention of MSCs in the body when conventional MSCs are used as a cell therapeutic agent. Accordingly, a cell therapeutic agent in which an adenovirus is loaded in MSCs increases the productivity of the virus, thereby maximizing anticancer efficacy, and has the effect of minimizing the side effects of MSCs.

Experimental Example 2-3

Establishment of Human Liver Cancer Orthotopic Model

Figure 19:
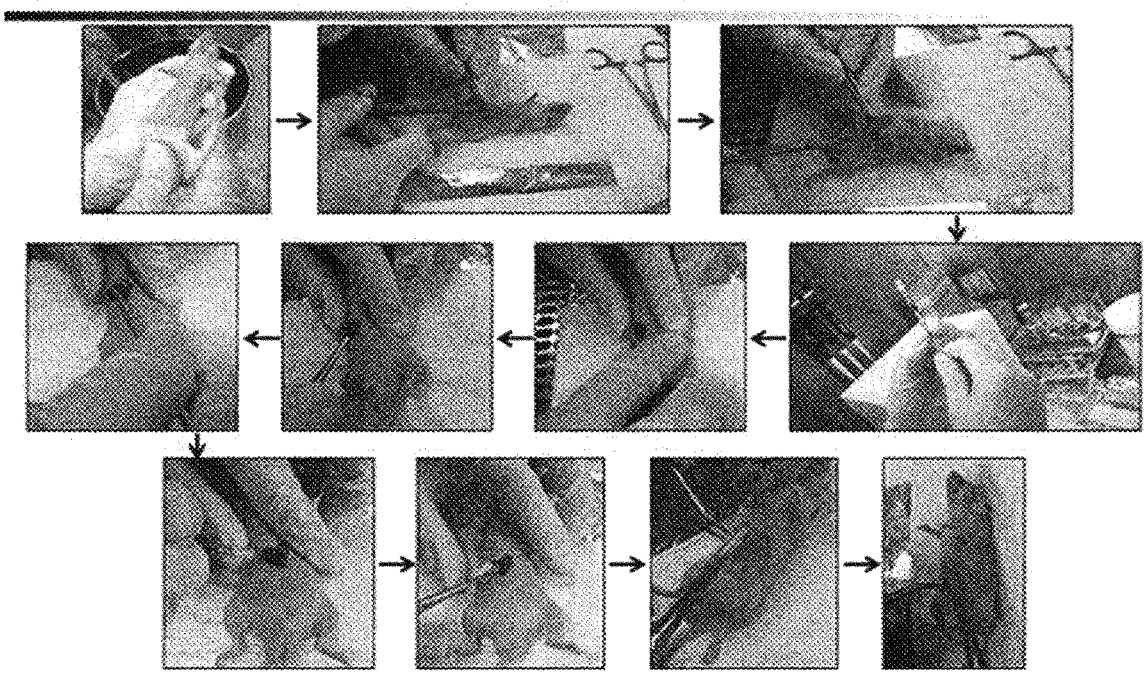
FIG. 19 illustrates a process of establishing a human liver cancer orthotopic model according to an embodiment of the present invention.
Figure 20:
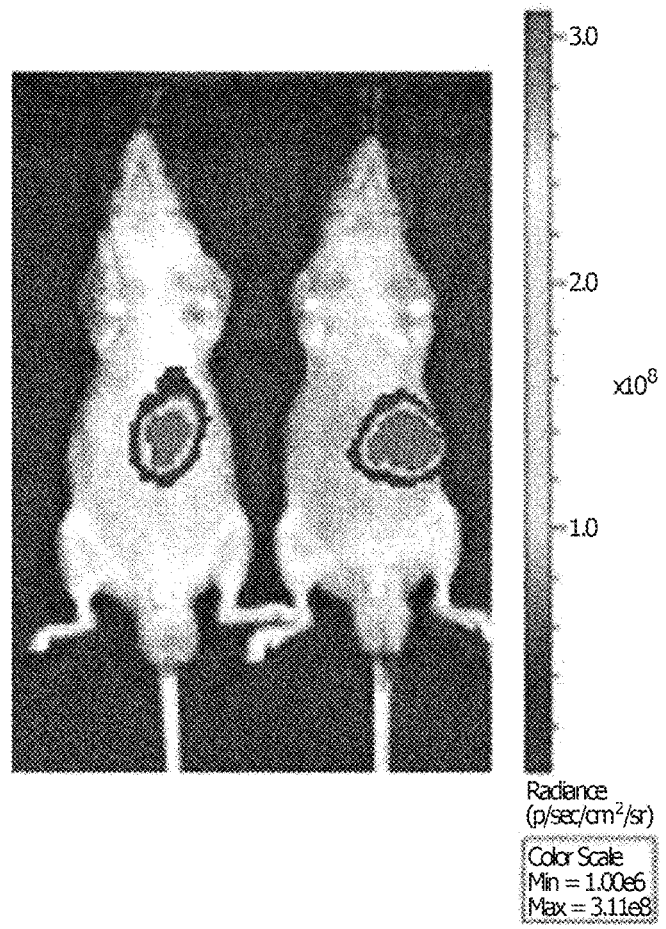
FIG. 20 is a luminescence (luciferase) image confirming the generation and growth of a tumor in a human liver cancer orthotopic model established according to an embodiment of the present invention.

To establish an orthotopic model, which is the closest to an actual tumorigenic model, the abdominal subcutaneous tissues of 6-week-old male nude mice were incised, $1\times10^6$ Hep3B cells suspended with 20 μl of HBSS and stably expressing luciferase were mixed with 20 μl of Matrigel, the mixture was directly injected into the left hepatic lobe (see FIG. 19). 2 weeks after cell injection, blood was collected from the mice, serum was separated, and then an AFP ELISA kit was used to measure the level of AFP expression in the blood, and the mice having an AFP expression level of 300 ng/mL or more were used in the experiment. In addition, tumor growth and changes in the nude mice to which the luciferase-expressing liver cancer cell line was administered were observed through luminescence imaging in real time (see FIG. 20).

Experimental Example 2-4

Cancer Targeting of Gene Therapeutic Agent by Oncolytic Adenovirus-Loaded Stem Cells To confirm tumor-specific localization of Ad-MSC and liver cancer-specific replication of adenoviruses in a liver cancer orthotopic model, first, MSCs were infected with H5cmT-Rd19-k35/Luc at 0.2 MOI, 0.5 MOI, and 1 MOI, respectively. After 24 hours, the respective mesenchymal stem cells were administered into the liver cancer orthotopic model (nude mice) at a density of $1\times10^6$ cells/mouse via the tail vein. In addition, PBS as a control was administered into the liver cancer orthotopic model via the tail vein. From 2 hours to 28 days after administration, the migration and replication ability of the virus were observed through luminescence imaging in real time.

Figure 21:
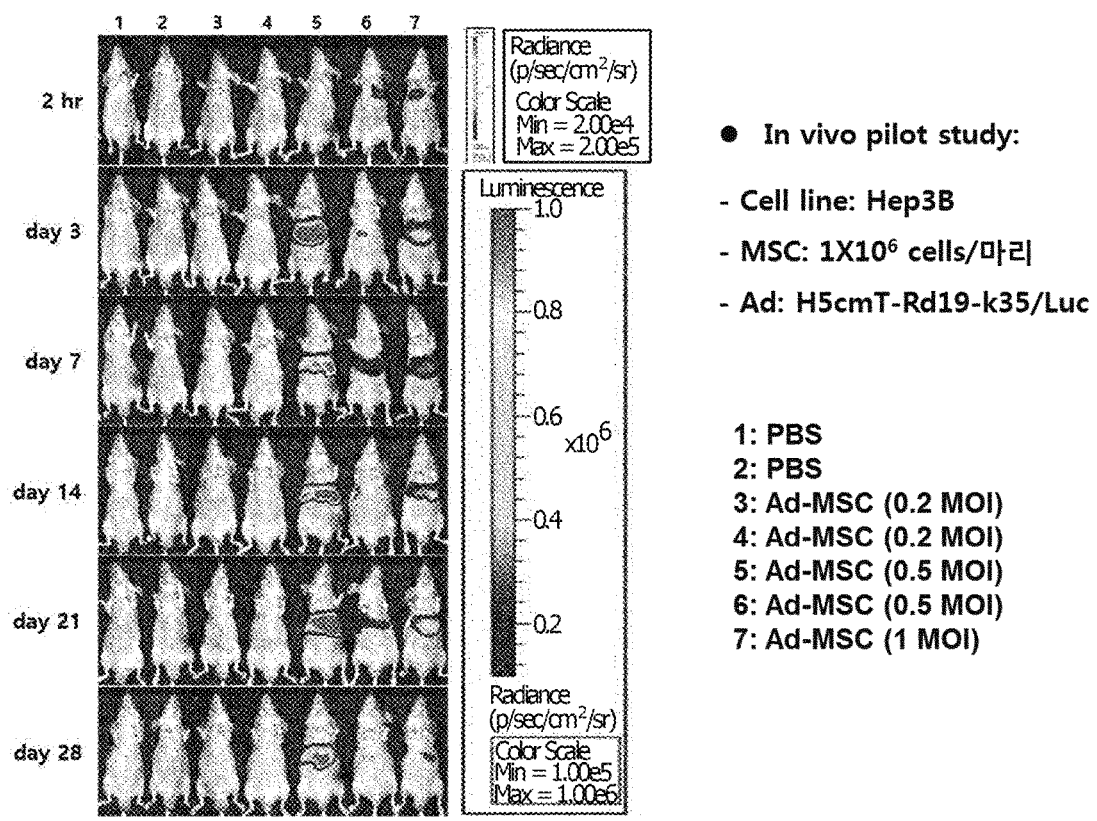
FIG. 21 is a set of luminescence (luciferase, Luc) images showing the results of confirming targeting of tumor tissue in the body and the proliferative capacity of an adenovirus when Ad-MSC constructed according to an embodiment of the present invention was administered.

As illustrated in FIG. 21, it was confirmed that, in the group administered Ad-MSCs infected with a pan-cancer-specific oncolytic adenovirus at a concentration of 0.5 MOI and 1 MOI, the Ad-MSCs were successfully delivered to a tumor site and, up to day 28 after administration, the virus exhibited a therapeutic effect while surviving. This suggests that the oncolytic virus according to the present invention actively replicates, and thus exhibits a therapeutic effect while being maintained for a long period of time in the tumor.

Experimental Example 2-5

Figure 22:
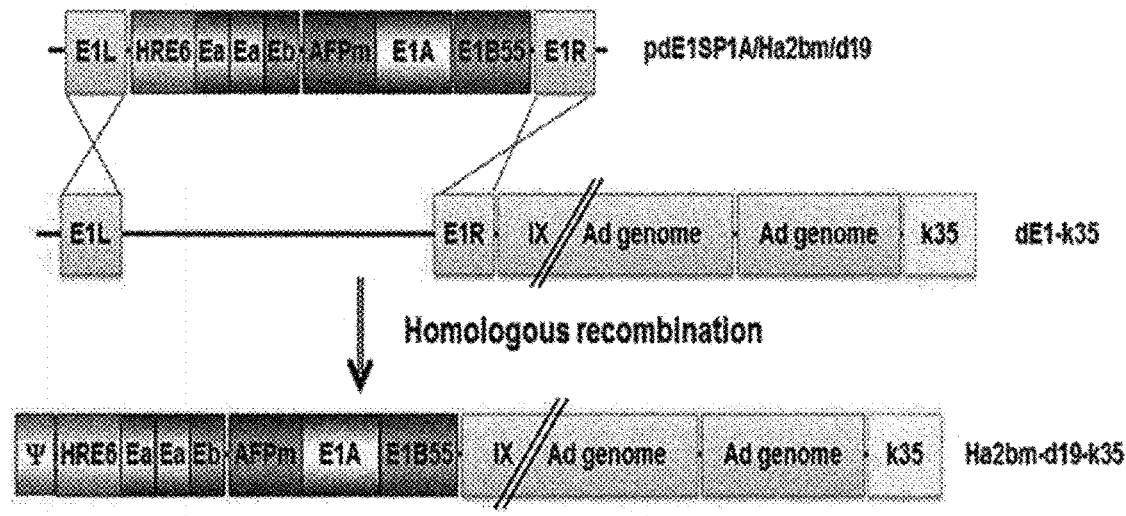
FIG. 22 illustrates the homogenous combination process and structure of a liver cancer-targeting oncolytic adenovirus capable of gene transduction into MSCs constructed according to an embodiment of the present invention.

Construction and Production of Cancer-Targeting Adenovirus for Loading in Stem Cell Through the experiment of Example 1 for comparison of the activities of the liver cancer-specific promoters, $a_2$bm having a small size and excellent promoter activity was selected, and HRE-inserted Ha$_2$bm, which is able to replicate even in a hypoxic condition, was finally selected as a liver cancer-specific promoter. In addition, based on the results of Experimental Example 2-1, a fiber with excellent gene transduction efficiency into an MSC and having a sequence of SEQ ID NO: 1 was selected, and in order to confirm gene transduction efficiency, the reporter gene Luc was inserted and Ha$_2$bm-d19-k35/Luc was finally selected as a candidate. To construct a virus, the shuttle vector ΔE1sp1A/Ha$_2$bm/d19 was linearized with XmnI, the total vector dE1-k35 was linearized with BstBI, followed by transfection into BJ5183 *E-coli* and E1 homogenous recombination, thereby constructing Ha$_2$bm-d19-k35 (see FIG. 22).

Figure 23A:
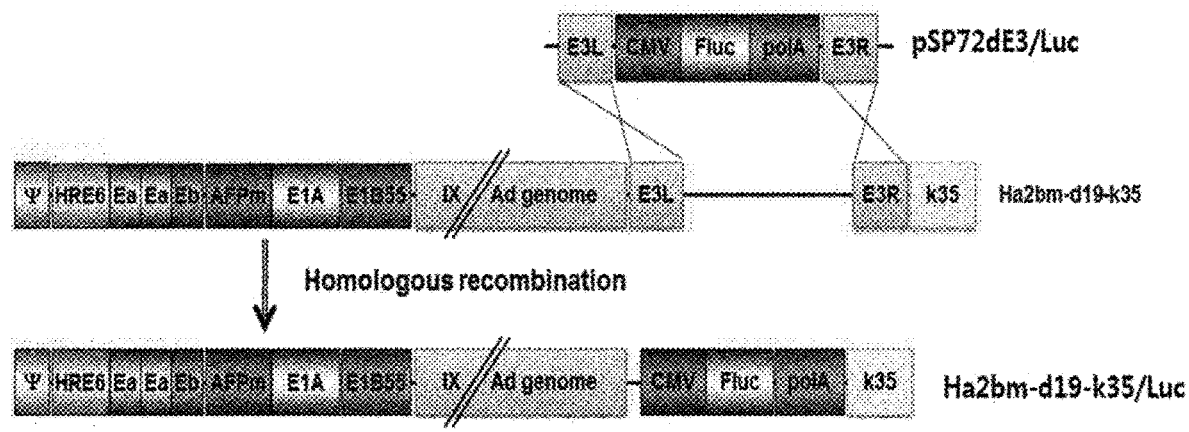
FIGS. 23A and 23B illustrate the homogenous combination process and structure of a Luc-expressing, liver cancer-targeting oncolytic adenovirus capable of gene transduction into MSCs constructed according to an embodiment of the present invention.
Figure 23B:
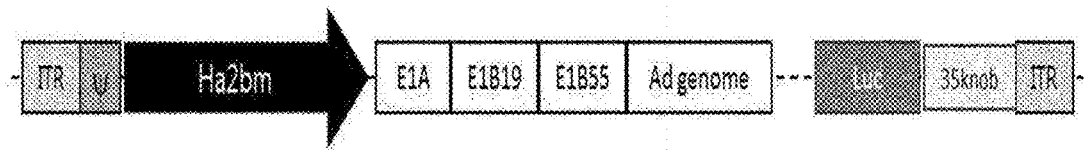

Next, a firefly luciferase expression cassette was ligated to an Ad E3 shuttle vector (pSP72 E3), thereby constructing a pSP72ΔE3/Luc Ad E3 shuttle vector. To construct a WNTi-expressing HCC-targeting oAd vector, a sequence encoding WNTi was subcloned from pCA14-sLRP6E1E2 [60], and then ligated to pSP72ΔE3, thereby constructing a pSP72ΔE3/WNTi_Ad E3 shuttle vector. The Ad E3 shuttle vectors (pSP72ΔE3/Luc and pSP72ΔE3/WNTi) were linearized using XmnI, and co-transformed into *E. coli* BJ5183 cells along with HCC-oAd(Ha$_2$bm-d19-k35)[48] linearized with SpeI, followed by homogenous recombination, thereby constructing a plasmid comprising either Ha$_2$bm-d19-k35/Luc (HCC-oAd-Luc) or Ha$_2$bm-d19-k35/WNTi (HCC-oAd-WNTi) (see FIG. 23A). Homogenous recombinant Ad plasmids were cleaved with PacI and transfected into HEK293 cells, which belongs to an adenovirus-producing cell line, using Lipofectamine, thereby constructing HCC-targeting HCC-oAd-Luc and HCC-oAd-WNTi (see FIG. 23B). When viral particles were produced in HEK293 cells, HCC-oAd-Luc and HCC-oAd-WNTi were propagated in A549 cells and purified by CsCl gradient centrifugation. The number of VPs was calculated from optical density measurements at 260 nm (OD$_{260}$) where an absorbance of 1 (OD$_{260}$=1) was equivalent to $1.1\times10^{12}$ VP/mL. The purified viruses were stored at −80° C. until use.

Experimental Example 2-6

Comparison of Transduction Efficiencies of, in MSCs, Liver Cancer-Targeting Adenoviruses for Loading in Stem Cell To confirm the transduction efficiencies of tumor-specific oncolytic adenoviruses into MSCs, each of the adenovirus vectors constructed in Experimental Example 2-1 and designed to express GFP was transduced at 500 MOI into mesenchymal stem cells and after 24 hours, the expression level of the GFP gene was examined.

In addition, MSCs were infected with Ha$_2$bm-d19-k35/Luc (HCC-oAd-Luc), which is liver cancer-specific oncolytic adenovirus expressing the Luc gene, at an MOI of 0, 50, 100, or 200 and after two days (48 hours after infection), the IVIS imaging system (Xenogen Corp, Alameda, CA) was used to confirm luciferase signals. The bioluminescence signal intensity was obtained as photons acquired per second (p/s) from the region of interest.

Figure 24A:
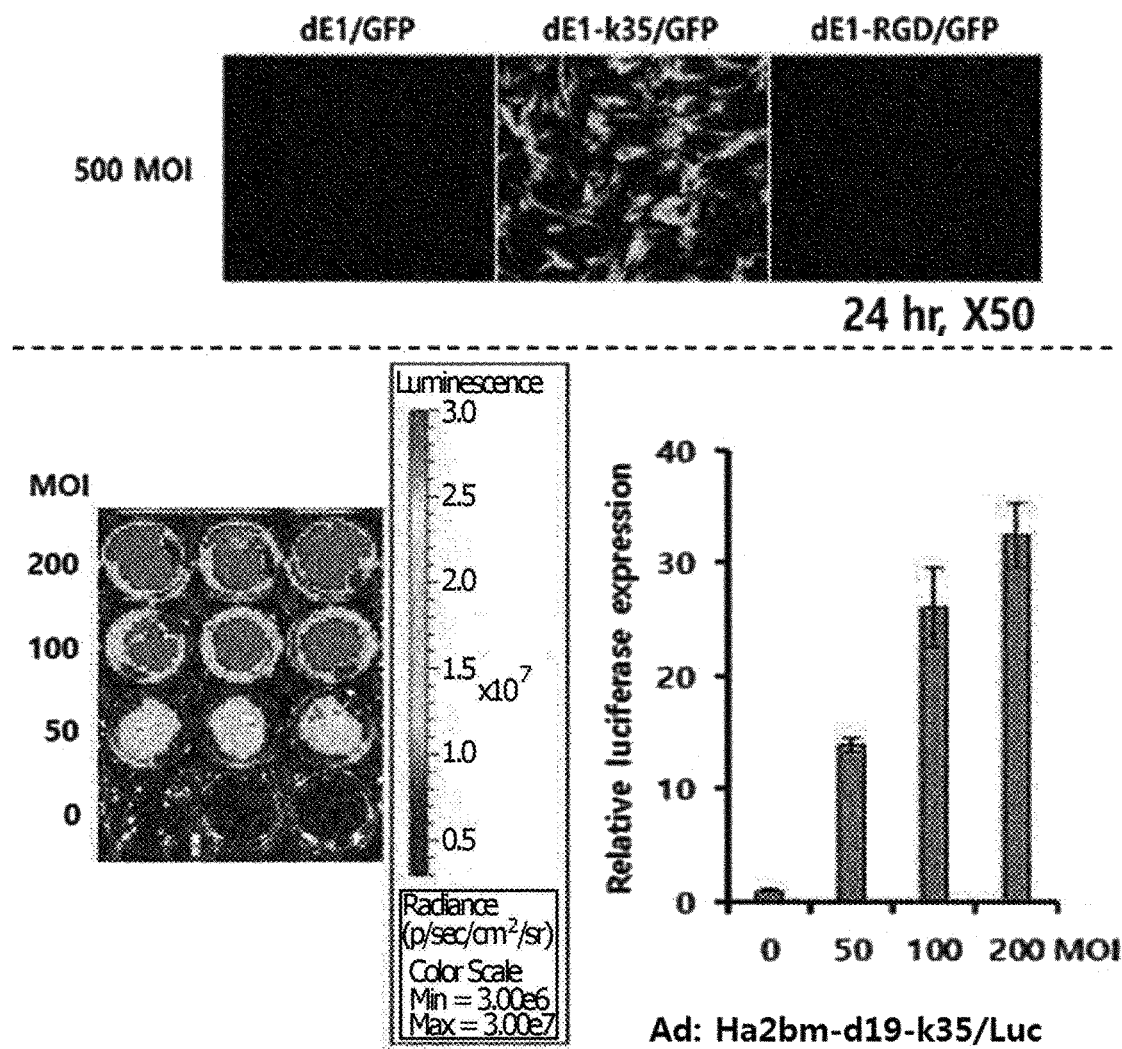
Figure 24B:
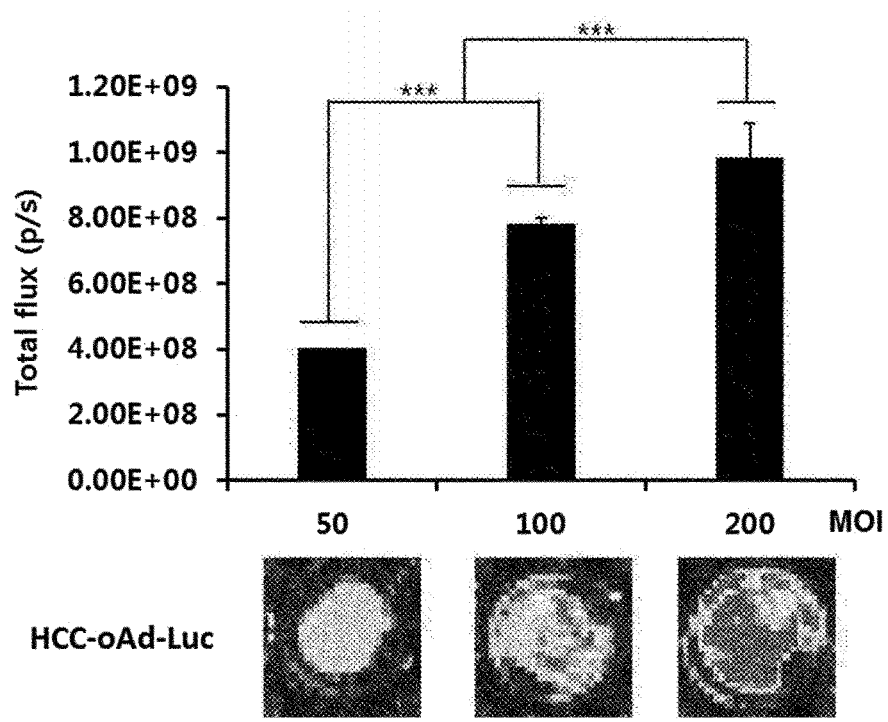

As illustrated in FIG. 24, it was confirmed that only the case of dE1-k35/GFP exhibited smooth gene transduction into MSCs and, when MSCs were infected with 50, 100, or 200 MOI of oAd, Luc expression was increased in a manner dependent on the concentration of the adenovirus (P<0.001). These results demonstrate that the Ad according to the present invention is efficiently transduced into MSCs, and thus is able to express a transgene.

Experimental Example 2-7

Figure 25:
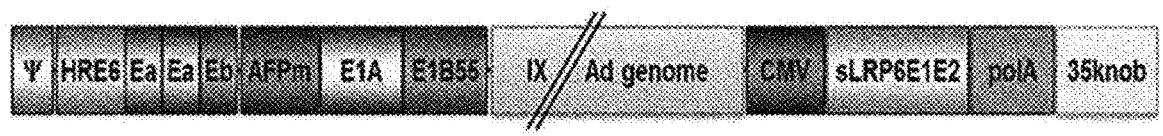
FIG. 25 illustrates the structure of a therapeutic gene-expressing, liver cancer-targeting adenovirus for loading in stem cells according to an embodiment of the present invention.
Figure 26:
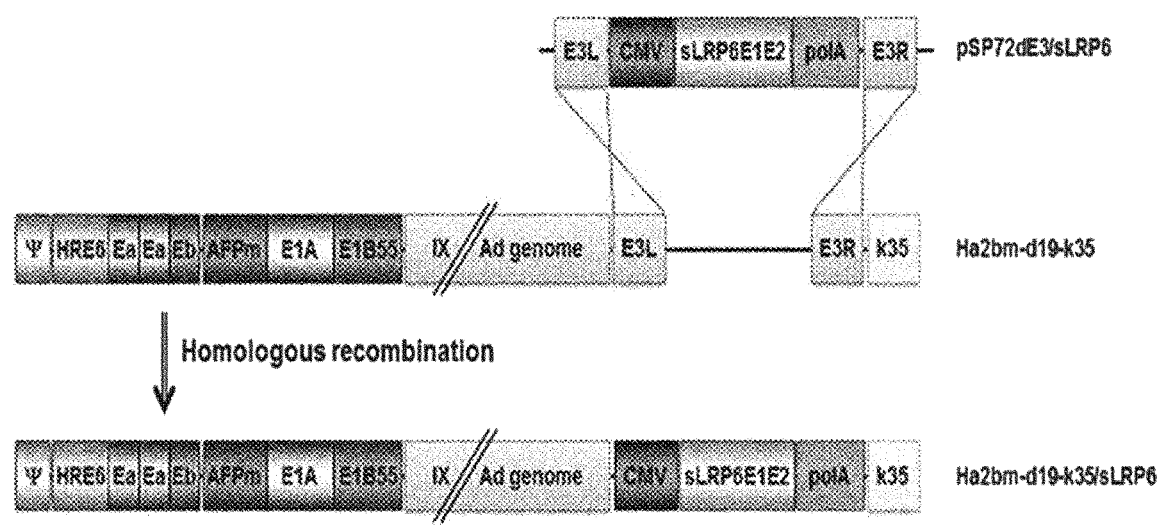
FIG. 26 illustrates the homologous recombination process and structure of a sLRP6-expressing, liver cancer-targeting adenovirus for loading in stem cells according to an embodiment of the present invention.

Construction and Production of Therapeutic Gene-Expressing Liver Cancer-Targeting Adenovirus for Loading in Stem Cell Through the experiment for comparison of the activities of the liver cancer-specific promoters, a$_2$bm having a small size and excellent promoter activity was selected, and HRE-inserted Ha₂bm, which is able to replicate even in a hypoxic condition, was finally selected as a promoter, thereby constructing a liver cancer-specific oncolytic adenovirus. To construct an sLRP6 gene-expressing adenovirus capable of blocking beta-catenin/wnt signaling in order to increase tumor cell-killing capability, a Ha₂bm-d19-k35 total vector was linearized with SpeI, a pSP72dE3/sLRP6 shuttle vector was linearized with XmnI, followed by transformation into BJ5183 E-coli and E3 homogenous recombination, thereby constructing a Ha₂bm-d19-k35/sLRP6 plasmid (see FIGS. 25 and 26).

The constructed plasmid DNA was cleaved with restriction enzyme PacI to be linearized, and then transformed into HEK293, which is an adenovirus-producing cell line, using Lipofectamine, thereby producing a virus. The HEK293 cell line was infected again with the produced adenovirus, concentrated using a CsCl gradient method, and purely isolated, and then limiting dilution assay and optical density (O.D) by absorbance of the viral genome were used to determine the titer of the adenovirus.

Experimental Example 2-8

Comparison of Liver Cancer Cell- and Normal Cell-Killing Capabilities of Liver Cancer-Targeting Oncolytic Adenoviruses To confirm the liver cancer cell-specific killing potency of liver cancer-specific oncolytic adenovirus Ha₂bm-d19-k35/sLRP6, liver cancer cell lines Hep3B, Huh7, and Hep1, and HDF as normal cells were infected therewith at 0.1, 0.5, 2, 10, and 50 MOI, respectively, and after 72 hours, cell-killing potency was examined through MTT assay.

Figure 27:
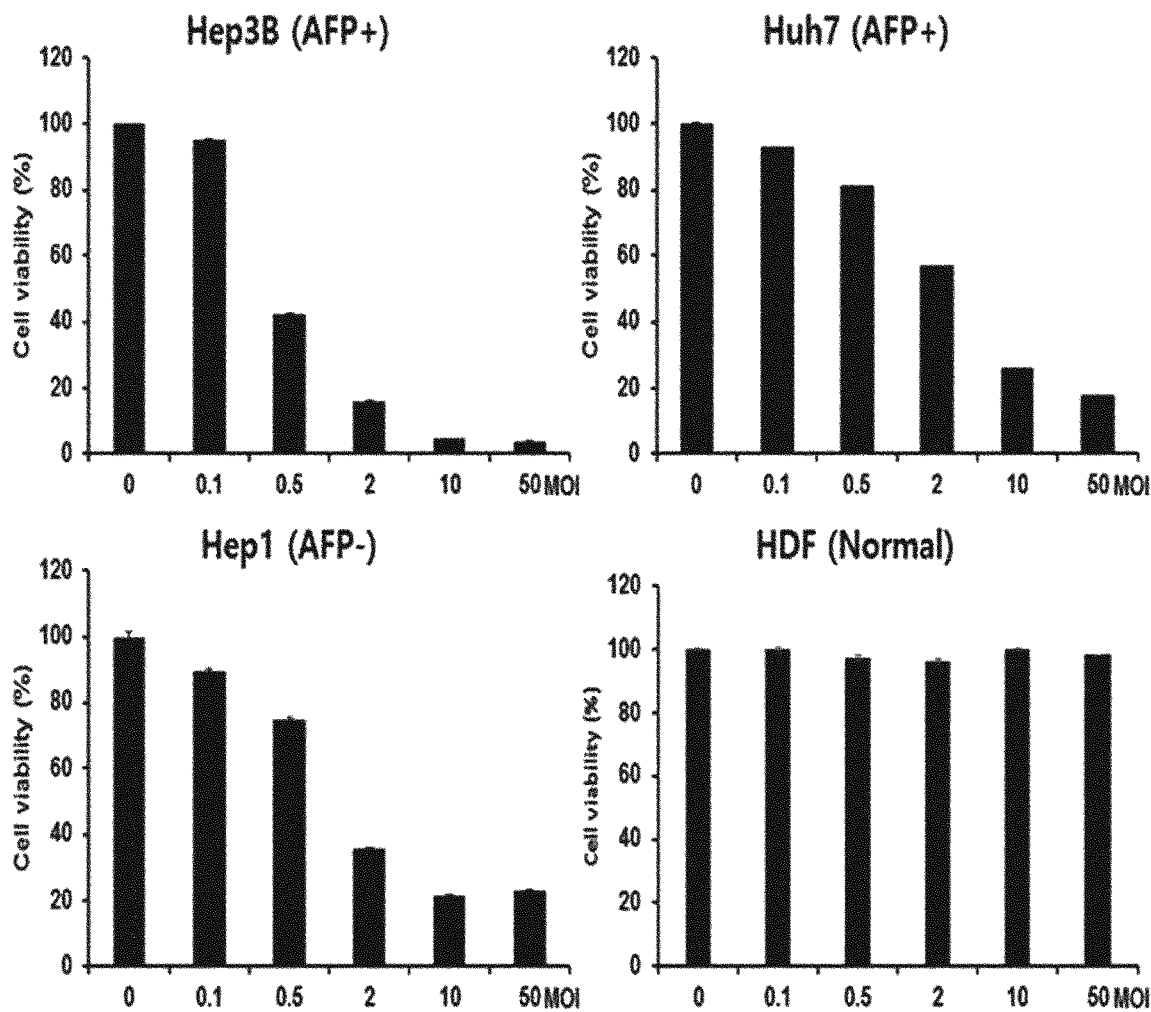
FIG. 27 is a set of graphs for comparing the killing effects of a liver cancer-specific oncolytic adenovirus constructed according to an embodiment of the present invention according to types of cell lines (liver cancer cells (Hep3B, huh7, and Hep1) and normal cells (HDF)).

As illustrated in FIG. 27, it was confirmed that the killing potency was increased, according to the concentration of a liver cancer-specific oncolytic adenovirus, in the liver cancer cell lines Hep3B, Huh7, and Hep1. It was also confirmed that the killing effect was not shown in HDF as normal cells. This means that Ha₂bm-d19-k35/sLRP6 does not exhibit a normal cell-killing effect and had an excellent ability to target only cancer cells. In addition, Ha₂bm-d19-k35/sLRP6 exhibited excellent cancer cell-killing potency not only in AFP-positive liver cancer cells (Hep3B and Huh7) but also in AFP-negative liver cancer cells (Hep1), which indicates that Ha₂bm-d19-k35/sLRP6 has excellent therapeutic capacity that is applicable to various phenotypes of clinical liver cancer patients.

Experimental Example 2-9

Optimization of Dose of oAd Loaded into MSCs

To prevent cells from being lysed at an early stage before reaching target tissue through systemic circulation, it is very important to optimize the loading dose of oAd loaded into MSCs as a carrier. Thus, the optimal dose of oAd for loading into MSCs was evaluated.

To confirm the cell-killing potency of a liver cancer-targeting oncolytic adenovirus in MSCs, MSCs were infected with the liver cancer-specific oncolytic adenovirus Ha₂bm-d19-k35/sLRP6 at 0.5, 1, 2, 5, 10, 20, and 50 MOI, respectively, and then on day 2 and day 5, MTT assay was performed to compare the cell viability of the mesenchymal stem cells.

Figure 28:
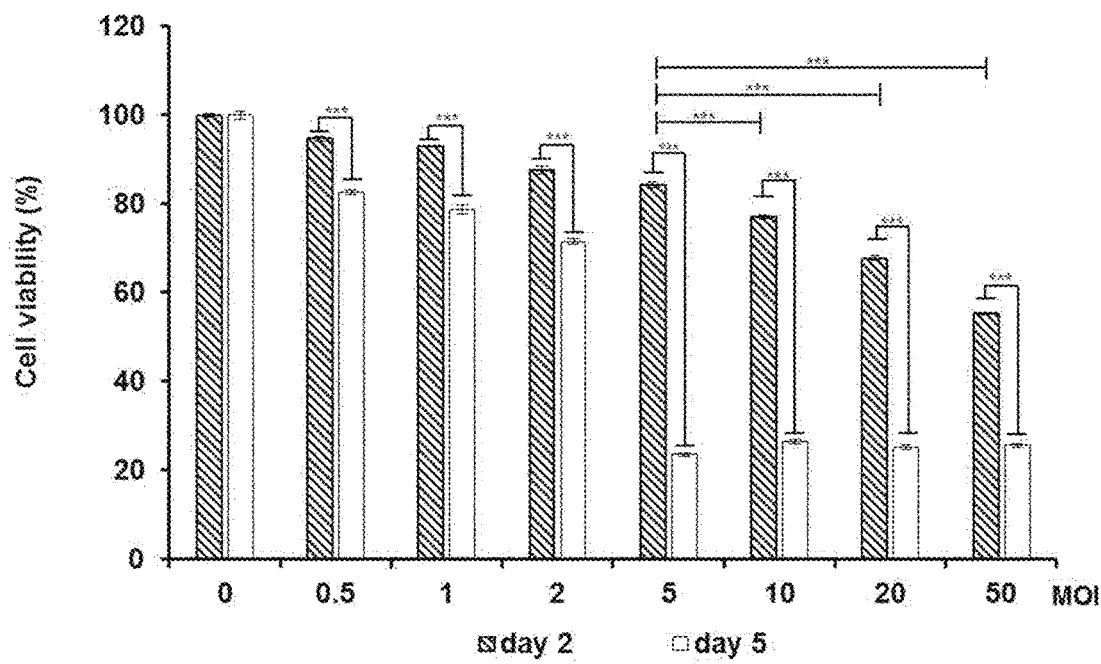
FIG. 28 is a graph showing the results of confirming the MSC-killing potency of a liver cancer-specific oncolytic adenovirus constructed according to an embodiment of the present invention, wherein, in the graph, the vertical axis denotes the cell viability of MSCs and the horizontal axis denotes the dose of an adenovirus (Ha2bm-d19-k35/sLRP6) which infected mesenchymal stem cells, and each treatment group denotes elapsed time (day 2 and day 5) after infection.

As illustrated in FIG. 28, the viability of MSCs was significantly lower (p>0.001) at all loading doses on day 5 after infection, compared to day 2 after infection. It was confirmed that the cell killing potency was increased according to an increase in concentration of virus and over time. Through this, it was confirmed that, when MSCs targeted a tumor and reached cancer tissue, not only tumor cells but also MSCs could be removed in vivo by the cell-killing effect of the virus, and thus concerns about the retention of MSCs in the body, caused when conventional MSCs are used as a cell therapeutic agent, could be alleviated. Thus, the cell therapeutic agent of the present invention in which an adenovirus is loaded in MSCs causes the amount of the virus to be increased through the proliferative effect of the virus in the MSCs while being delivered to cancer tissue, thereby maximizing anticancer action, and, after reaching the cancer tissue, may cause the MSCs to be removed, thereby minimizing side effects that may occur due to the retention of the MSCs in the body, thus presenting the possibility of enhancing the safety of the cell therapeutic agent.

Next, to further optimize oAd-loaded MSCs, the degree of viral proliferation in MSCs was measured.

Experimental Example 2-10

Confirmation of Production of Adenovirus in MSCs

To confirm the production of a liver cancer-specific oncolytic adenovirus in MSCs, MSCs were infected with the liver cancer-specific oncolytic adenovirus Ha₂bm-d19-k35/sLRP6 at 0.5, 1, 2, 5, 10, 20, 50, and 100 MOI, respectively, and then on day 2 and day 5, QPCR was performed to compare the production of the virus.

Figure 29:
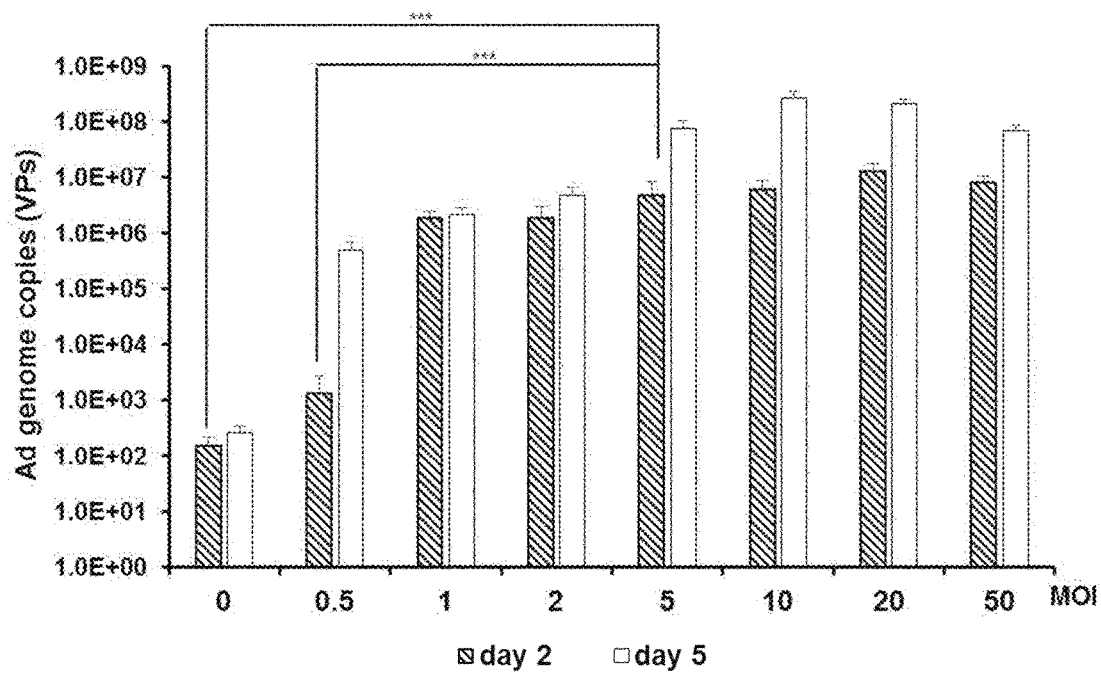
FIG. 29 is a graph showing the results of confirming the proliferative capacity of an adenovirus in mesenchymal stem cells in which a liver cancer-specific oncolytic adenovirus constructed according to an embodiment of the present invention is loaded, wherein, in the graph, the vertical axis denotes the number of adenoviruses (Ad genome copies, VP/ml) and the horizontal axis denotes the dose of an adenovirus (Ha2bm-d19-k35/sLRP6) which infected the MSCs, and each treatment group denotes elapsed time (day 2 and day 5) after infection

As illustrated in FIG. 29, on day 2 after infection, a 10-fold increase in the amount of the virus from 0.5 MOI to 5 MOI caused a 5,000-fold higher level of production of the virus. However, a similar level of increase from 5 MOI to 50 MOI showed only an approximately 1.8-fold minimum increase. An increase in the level of production of the virus exhibited a stable state at an MOI of 5 or more, and a significant dose-dependent decrease was observed in the viability of MSCs in the same dose range of the virus, and thus, when producing oAd-loaded MSCs, 5 MOI and infection for 2 days were used as optimal conditions for balancing the proliferation of the virus and the viability of MSCs.

Experimental Example 2-11

Verification of Antitumor Effect of Liver Cancer-Specific Oncolytic Adenovirus-Loaded Stem Cell (HCC-oAd-WNTi/MSC)

2-11-1. Characterization of WNTi-Expressing HCC-Targeting oAd

Figure 38A:
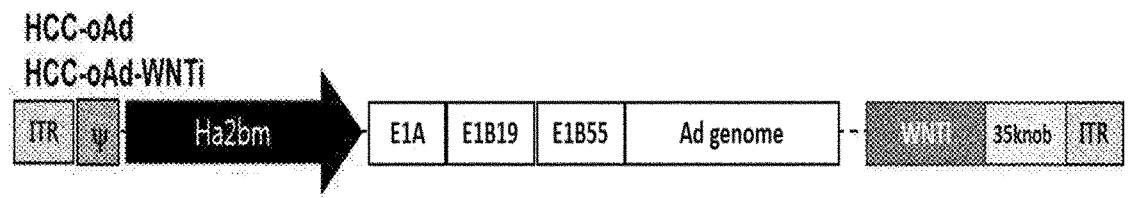

WNTi-expressing HCC-targeting oAd, i.e., HCC-oAd-WNTi (see FIG. 38A), was constructed using an enhancer site-modified AFP promoter (Ha₂bm).

To evaluate whether the HCC-oAd-WNTi constructed in the present invention is able to inhibit the Wnt signaling pathway, the expression levels of various downstream factors related to Wnt and the Wnt signaling pathway in Hep3B cells infected with HCC-oAd or HCC-oAd-WNTi were examined through western blotting.

Figure 38B:
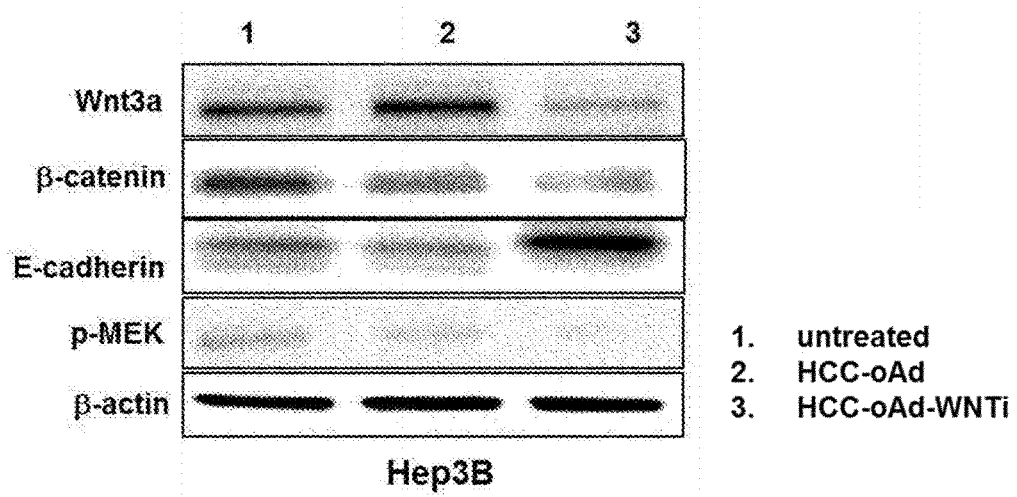

As illustrated in FIG. 38B, HCC-oAd-WNTi treatment induced a significantly low level of Wnt expression in Hep3B cells, compared to cells infected with oAd (HCC-oAd) as a control or a negative control (untreated group). In addition, the HCC-oAd-WNTi treatment significantly reduced the expression levels of various downstream factors such as β-catenin and phospho-MAPK/ERK (p-MEK), which are known to promote rapid cancer cell proliferation and EMT. In addition, the expression level of epithelial cadherin (E-cadherin), which is a mesenchymal marker, was significantly higher in Hep3B cells infected with HCC-oAd-WNTi than in untreated cells or HCC-oAd-infected cells. These results demonstrate that the Wnt signaling pathway of HCC cells is effectively inhibited by HCC-oAd-WNTi and ultimately prevent EMT.

Figure 38C:
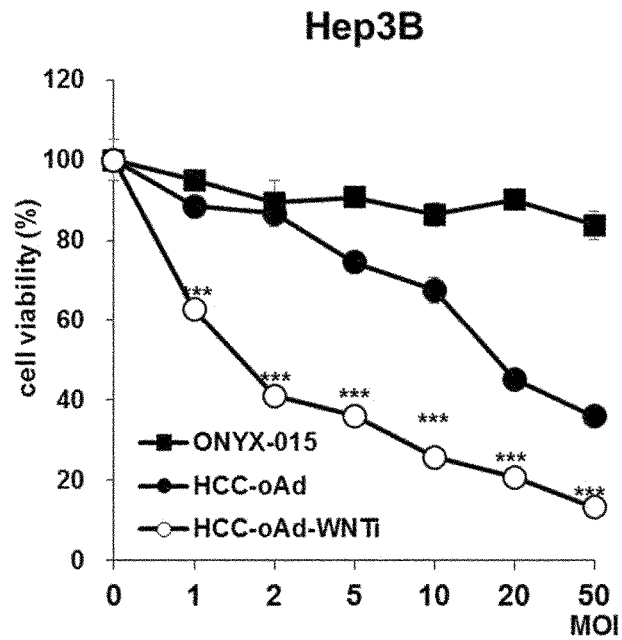

To evaluate whether WNTi expression by HCC-targeting oAd enhances the cancer cell-killing effect of oAd in HCC cells, AFP-positive HCC cells were infected with clinically approved oAd (H101), or HCC-oAd or HCC-oAd-WNTi as a homologous control at various MOIs. As illustrated in FIG. 38C, HCC-oAd-WNTi induced a significantly more potent cancer cell-killing effect in a dose-dependent manner at all MOIs in AFP-positive Hep3B cells, compared to H101 or the control HCC-oAd (P<0.001). This means that WNTi expression can enhance the cancer cell-killing effect of hepatocellular carcinoma (HCC)-specific oAd. HCC-oAd-WNTi exhibited 5.46-fold or 2.29-fold greater cytotoxicity on AFP-positive HCC cells (Hep3B) at 10 MOI than in H101 or HCC-oAd as a control.

Figure 38D:
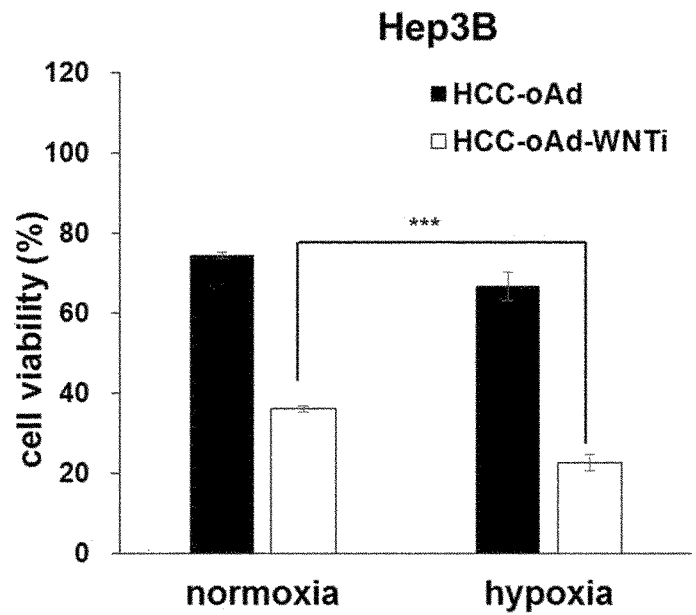

Since it was shown that the $Ha_2bm$ promoter overcomes hypoxia-medicated suppression of Ad replication in a hypoxic state, it was evaluated whether HCC-oAd-WNTi is able to induce a more potent cancer cell-killing effect in a hypoxia state under control of the $Ha_2bm$ promoter. As illustrated in FIG. 38D, HCC-oAd-WNTi exhibited an enhanced cancer cell-killing effect both in hypoxia and normoxia environments, compared to HCC-oAd. In addition, HCC-oAd-WNTi exhibited 1.2-fold greater cancer cell-killing efficiency in a hypoxic state than in a normoxic state (P<0.001). These results suggest that HCC-oAd-WNTi exhibits a potent cell-killing effect in AFP-positive HCCs and can overcome hypoxia-mediated downregulation of viral replication.

2-11-2. Potent Hepatoma Treatment Effect of HCC-oAd-WNTi/MSC

To evaluate the HCC-targeting oncolytic potency of HCC-oAd-WNTi/MSC, Hep3B cells and HCC-oAd-WNTi/MSC (MSCs infected with 5 MOI of virus for 2 days) were co-cultured at a cell ratio of 1:1.

Figure 39:
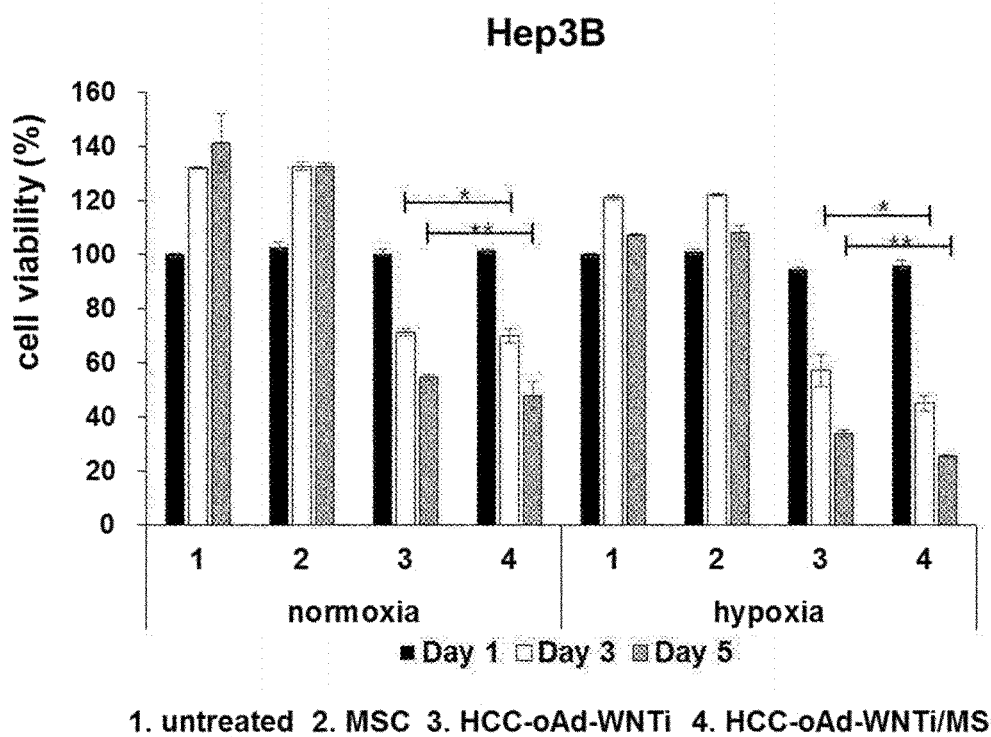
FIG. 39 is a graph showing the results of confirming the cancer cell-killing effect of HCC-oAd-WNTi-loaded mesenchymal stem cells (HCC-oAd-WNTi/MSC) according to an embodiment of the present invention, wherein an untreated group, a group treated with MSCs alone (MSC), and a group treated with naked Ad (HCC-oAd-WNTi) were used as controls for experiments.
Figure 40:
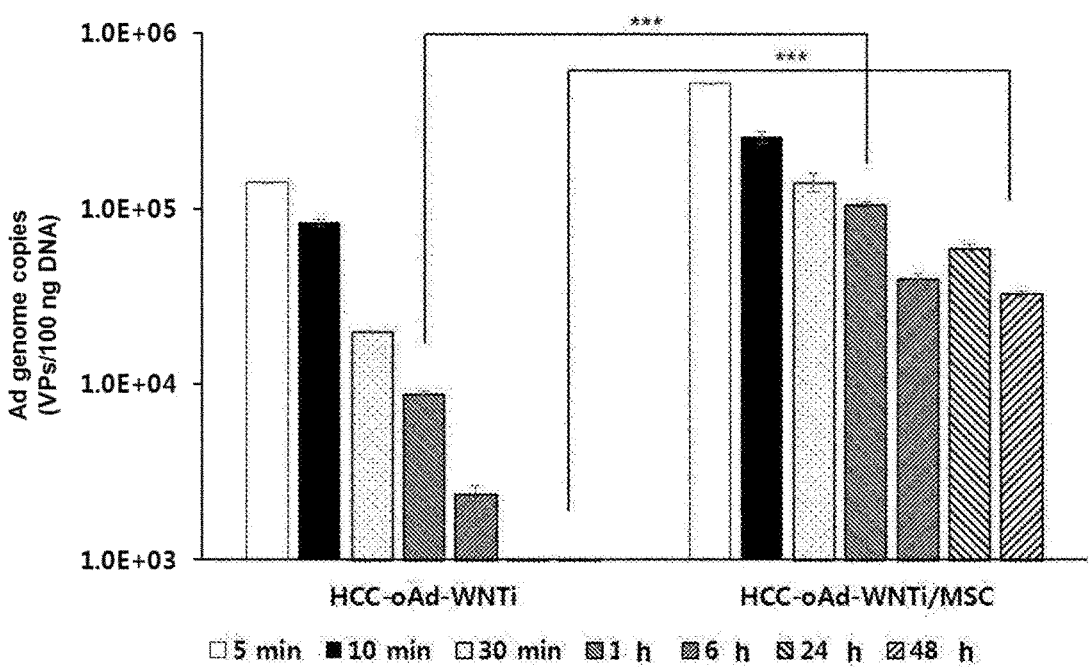
FIG. 40 illustrates the results of confirming the pharmacokinetic profile of HCC-oAd-WNTi-loaded mesenchymal stem cells (HCC-oAd-WNTi/MSC) according to an embodiment of the present invention.

As illustrated in FIG. 39, there was no significant difference in Hep3B viability between the untreated group and the MSC-administered group both under normoxic and hypoxic conditions from day 1 to day 5 after treatment, and thus it can be seen that MSCs do not affect the growth of cancer cells. In contrast, the Hep3B viability was significantly reduced in the group treated with HCC-oAd-WNTi or HCC-oAd-WNTi/MSC both under normoxic and hypoxic conditions on day 3 and day 5 after treatment, compared to the untreated group or the MSC-treated group, from which it was confirmed that both naked HCC-oAd-WNTi and Ad loaded in MSCs exhibited AFP-positive HCC cell-killing potency. In addition, Hep3B cells treated with HCC-oAd-WNTi or HCC-oAd-WNTi/MSC exhibit viability that is similar to that of the untreated group on day 1 after treatment, and from then on, a decrease in the viability of cancer cells caused by the oAd-comprising groups reconfirms that the decrease was due to replication-mediated effects. In addition, HCC-oAd-WNTi and HCC-oAd-WNTi/MSC exhibited a more potent cancer cell-killing effect under a hypoxic condition than under a normoxic condition on day 3 and day 5 after treatment due to $Ha_2bm$ promoter. For reference, HCC-oAd-WNTi/MSC treatment induced a more significantly potent HCC-killing effect in a normoxic condition or in a hypoxic condition (P<0.05, P<0.01) on day 3 or day 5 after treatment, compared to HCC-oAd-WNTi. These results demonstrate that, while the virus is delivered to HCC cells, the efficient viral replication of HCC-oAd-WNTi in MSCs can enhance the cancer cell killing effect of the oAd virus.

2-11-3. Verification of Antitumor Effect of Systemically Administered HCC-oAd-WNTi/MSC To evaluate the therapeutic efficacy of systemically administered Ad-MSC in an orthotopic HCC tumor model, luciferase-expressing orthotopic Hep3B tumor model mice were treated with PBS, MSC ($1\times10^6$ cells), HCC-oAd-WNTi ($5\times10^8$ VPs), or HCC-oAd-WNTi/MSC ($1\times10^6$ MSCs infected with $5\times10^8$ VP for 18 hours) via tail-vein injection.

Specifically, on day 8 and day 12 after liver cancer cell transplantation, MSCs were infected with 5 MOI of HCC-oAd-WNTi ($Ha_2bm$-d19-k35/sLRP6), which is a liver cancer-specific oncolytic adenovirus and after 24 hours, $1\times10^6$ MSCs were administered to the liver cancer orthotopic model (nude mice) via the tail vein. As controls, PBS, the same dose ($1\times10^6$ cells) of MSCs not infected with the virus, or the same dose ($5\times10^8$ VP) of Ad loaded in MSCs was administered via the tail vein.

Figure 30A:
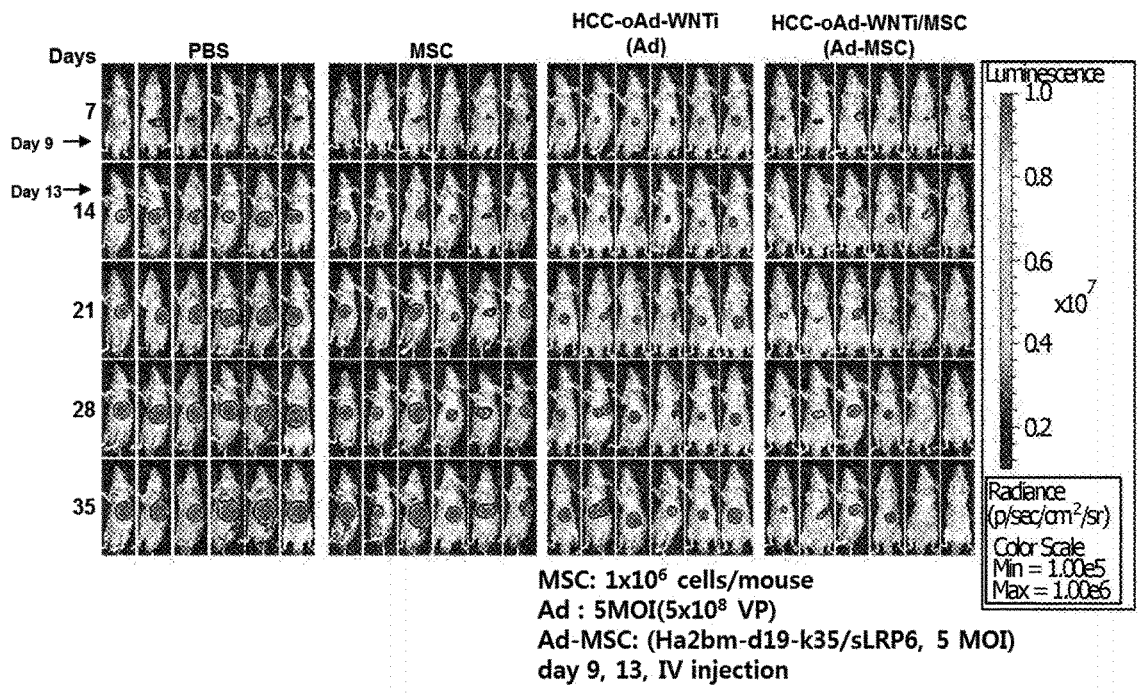
FIGS. 30A and 30B illustrate the results of confirming the in vivo antitumor effect of mesenchymal stem cells in which liver cancer-targeting oncolytic adenoviruses constructed according to an embodiment of the present invention are loaded.
Figure 30B:
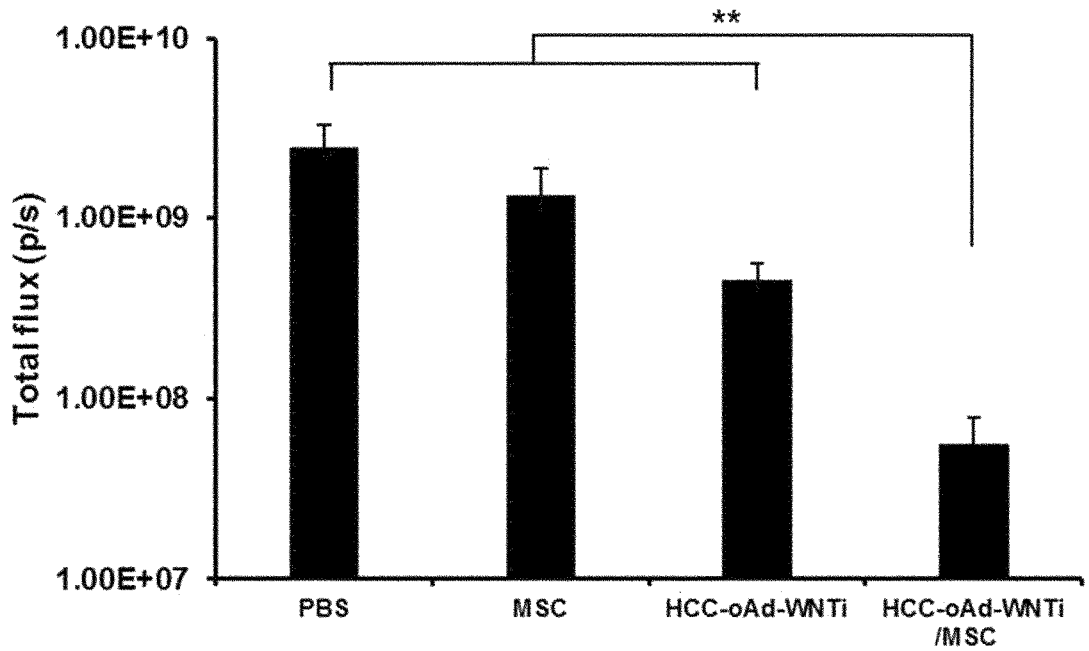
Figure 31:
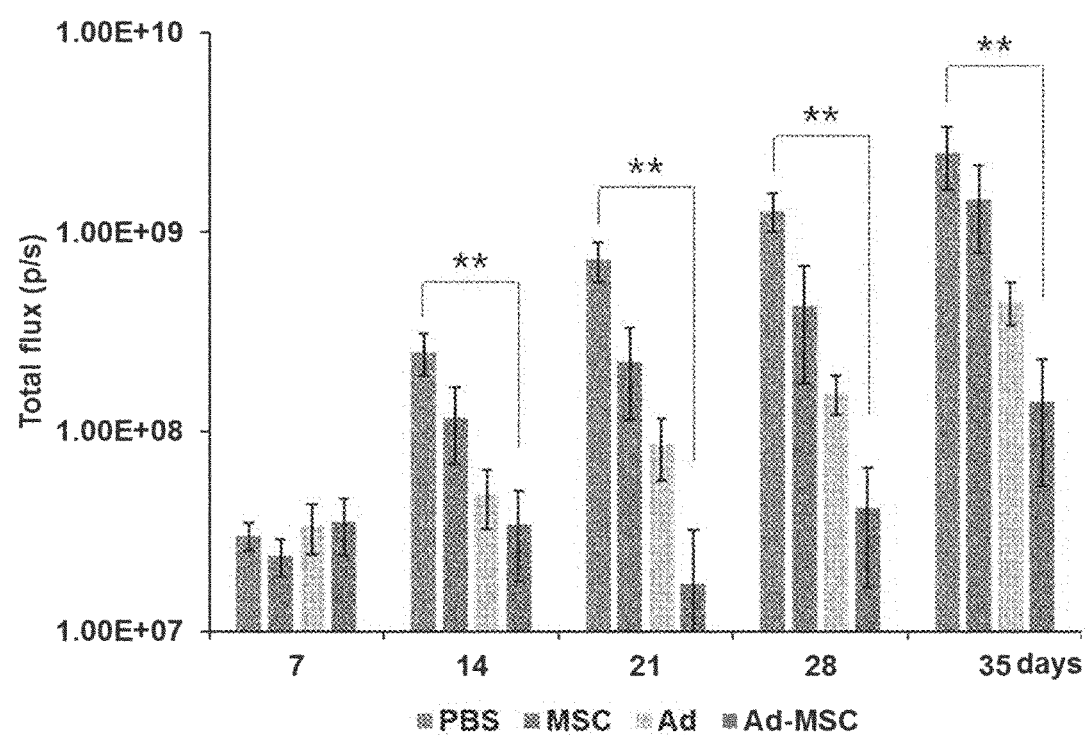
FIG. 31 is a graph showing, as quantification values, the results of confirming the in vivo antitumor effect of mesenchymal stem cells in which a liver cancer-targeting oncolytic adenovirus constructed according to an embodiment of the present invention is loaded.
Figure 32:
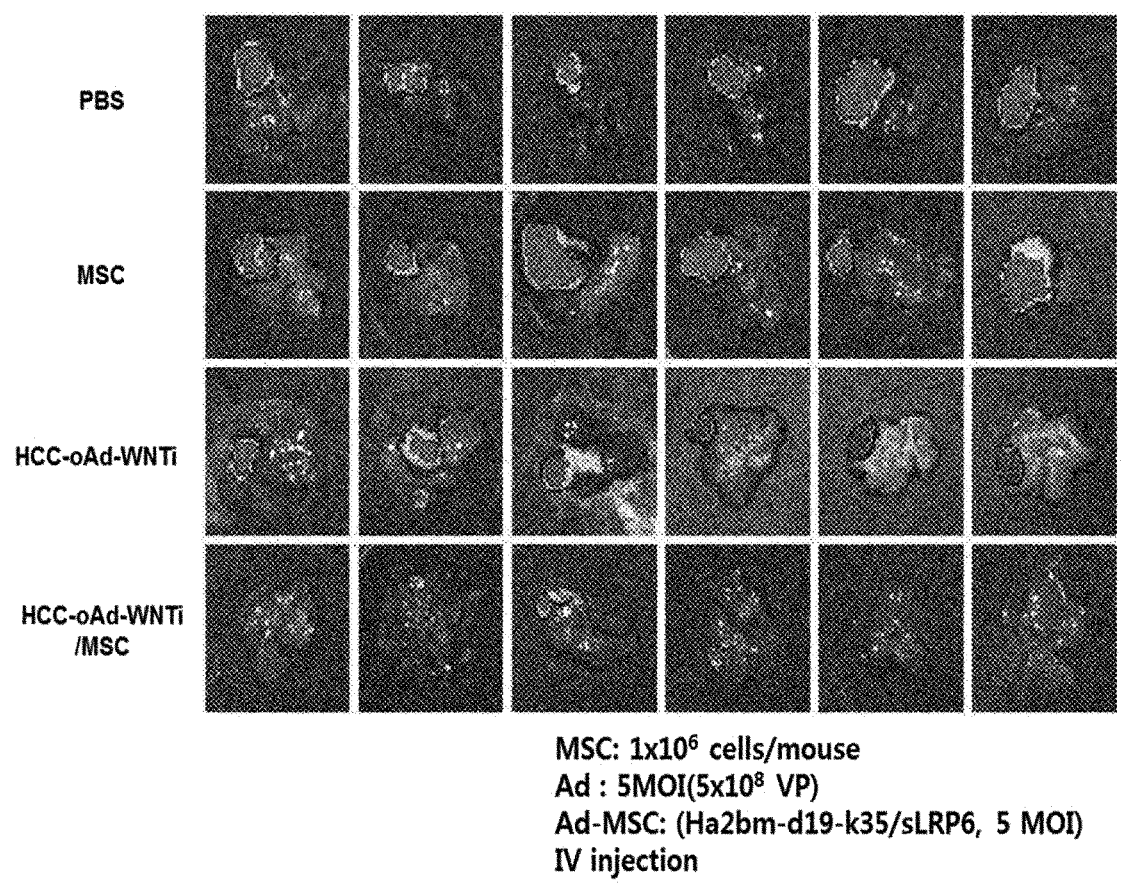
FIG. 32 illustrates the results of confirming, through ex vivo images, the antitumor effect of mesenchymal stem cells in which a liver cancer-targeting oncolytic adenovirus constructed according to an embodiment of the present invention is loaded.
Figure 33A:
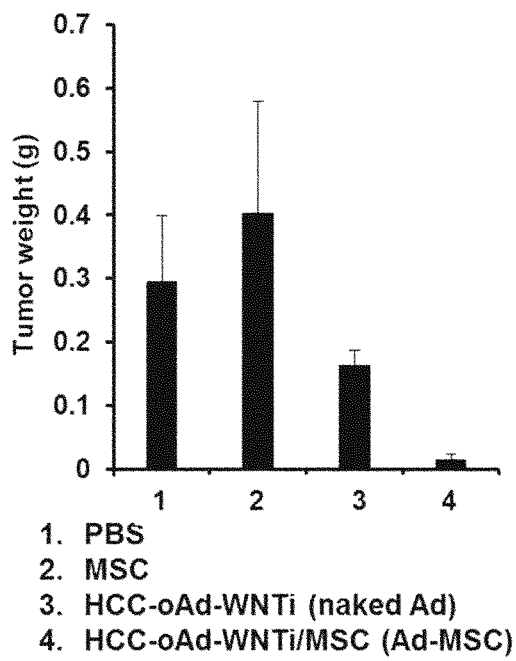
FIGS. 33A and 33B are graphs for comparing, according to the difference in tumor weight (33A) or a flux value (33B), the antitumor effect of mesenchymal stem cells in which a liver cancer-targeting oncolytic adenovirus constructed according to an embodiment of the present invention is loaded.
Figure 33B:
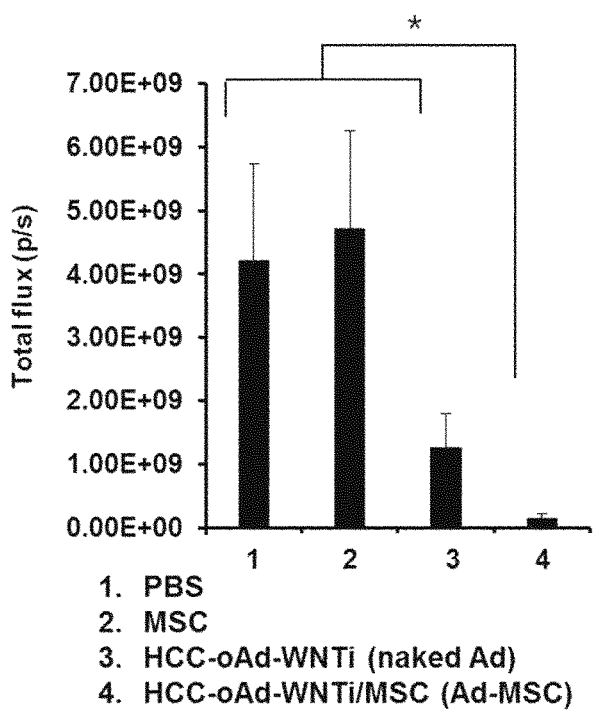

As illustrated in FIGS. 30A and 31, rapid tumor growth was observed in a control group (PBS), whereas remarkable inhibition of tumor growth was observed in the Ad-MSC-administered group. As illustrated in FIGS. 30A and 30B, the systemic administration of HCC-oAd-WNTi/MSC exhibited significantly more potent antitumor activity on day 35 after transplantation (P<0.01) compared to HCC-oAd-WNTi or the group administered MSCs alone, and exhibited a 447-fold, 24.0-fold, or 8.1-fold or greater therapeutic effect compared to PBS, MSC, or HCC-oAd-WNTi, respectively. It was also confirmed in ex-vivo images of orthotopic tumor model mice that a much larger tumor was observed in the liver treated with PBS, MSC, or HCC-oAd-WNTi, whereas a significantly smaller HCC tumor was observed in the liver treated with HCC-oAd-WNTi/MSC (see FIGS. 32 and 33A). These patterns were also observed as similar results when a tumor was evaluated by weight (see FIG. 33B). For reference, HCC-oAd-WNTi/MSC still exhibited a potent antitumor effect even when administered at a lower dose than the dose range of existing oAd (($\sim2\times10^{10}$ VP), which is commonly used in systemic treatment for mice with a tumor. These results suggest that loading of oAd into MSCs can significantly enhance therapeutic efficacy of the systemically administered virus and minimize dose-related side effects.

Experimental Example 2-12

Observation of Change in Liver Damage Index by Liver Cancer-Targeting Oncolytic Ad-MSC in Vivo To confirm liver function by the tumor therapeutic effect of Ad-MSC in a liver cancer orthotopic transplantation model, MSCs were infected with 5 MOI of $Ha_2bm$-d19-k35/sLRP6, which is a cancer-specific oncolytic adenovirus, for 18 hours, and the Ad-MSCs ($1\times10^6$ cells) were administered to the liver cancer orthotopic transplantation model (nude mice) via the tail vein. As controls, PBS, 200 μl of the same dose ($1\times10^6$ cells) of MSCs not infected with the virus, and naked Ad (tumor oncolytic adenovirus Ha2bm-d19-k35/sLRP6 not loaded in MSCs, $5\times10^8$ VP) were administered via the tail vein twice on day 9 and day 13. 3 days after the second injection, blood was collected from the four group of mice, and the serum levels of alanine transaminase (ALT) and aspartate aminotransferase (AST) were measured together with non-tumor normal mice as a control, to evaluate hepatotoxicity. Specifically, 0.5-1 mL of blood was collected from the mice, and then after 20-30 minutes, centrifuged at 3,000 rpm for 30 minutes. The supernatant as serum was collected and a toxicity testing institute was commissioned.

Figure 34:
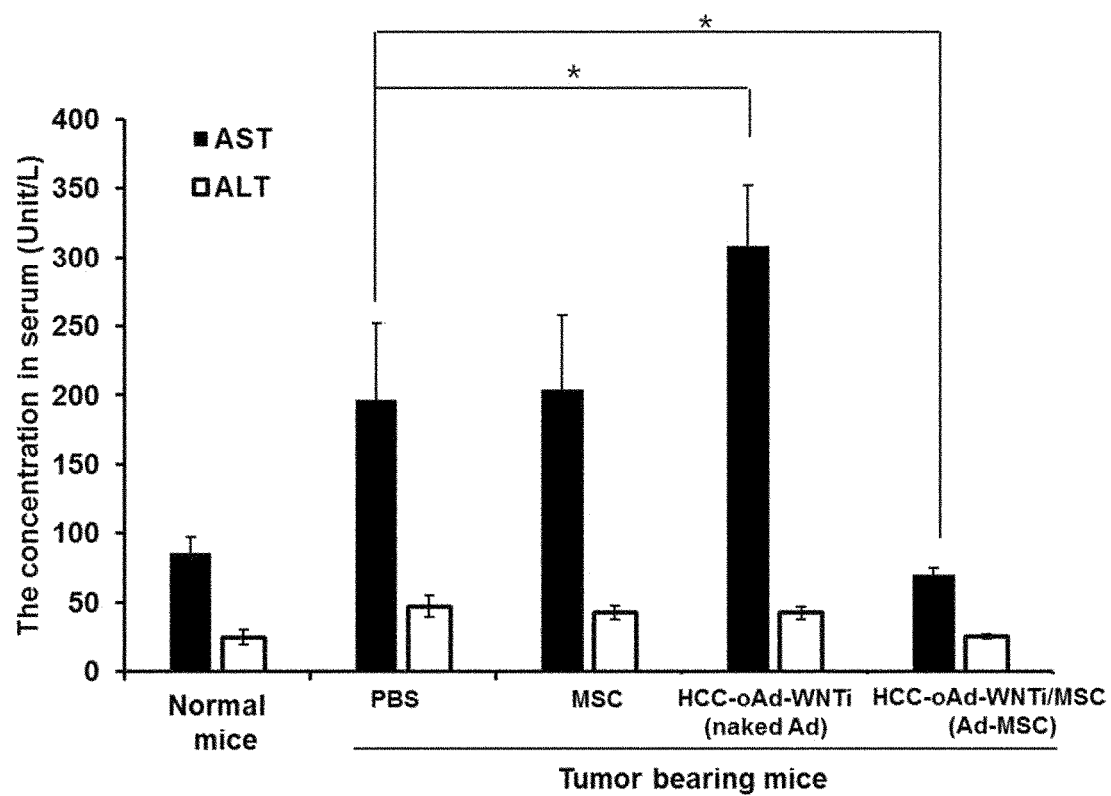
FIG. 34 is a graph showing the results of confirming in-vivo changes in a liver damage index that were caused by mesenchymal stem cells in which a liver cancer-targeting oncolytic adenovirus constructed according to an embodiment of the present invention is loaded.

As illustrated in FIG. 34, mice treated with HCC-oAd-WNTi exhibited the highest AST level (1.6-fold greater than that in PBS-treated group; P<0.05). In contrast, relative to the normal mouse group, a significant increase in AST level was not observed in mice treated with HCC-oAd-WNTi/MSC. Rather, it can be confirmed that the AST level is maintained at the same level as that of normal mice. This demonstrates that tumor-specific delivery of MSC-mediated oAd can prevent the occurrence of liver damage problems caused by HCC, as well as typical liver damage related to systemically administered Ad.

Experimental Example 2-13

Biodistribution Assay According to Systemic Administration of HCC-oAd-WNTi/MSC in Vivo Naked oAd is rapidly and nonspecifically sequestered in the liver after intravenous injection due to interactions with Kupffer cells and coagulation factors, resulting in hepatotoxicity and a limited antitumor effect. Thus, to examine whether HCC-oAd-WNTi/MSC can circumvent hepatic sequestration while enhancing oAd accumulation into a tumor, biodistribution profiles of systemically administered MSCs, HCC-oAd-WNTi, or HCC-oAd-WNTi/MSC were analyzed.

To analyze biodistribution, which is exhibited after systemic administration of tumor-specific oncolytic Ad-MSC in an orthotopic model, a Hep3B-Luc liver cancer orthotopic xenograft model was constructed, and then PBS, MSCs ($1\times10^6$ cells), Ha2bm-d19-k35/sLRP6 (HCC-oAd-WNTi, $5\times10^8$ VP), or MSCs (Ad-MSC, $1\times10^6$ cells) infected with $5\times10^8$ VP of Ha2bm-d19-k35/sLRP6 for 18 hours with were administered via the tail vein on day 9 and day 13, respectively, after tumor transplantation. 24 hours after the second administration to each group, the mice were anesthetized to collect blood, and then sacrificed, followed by extraction of liver cancer tissue, normal liver tissue, the stomach, spleen, lungs, pancreas, heart, and kidneys and DNA extraction. Specifically, the organs were frozen using liquid nitrogen, and then pulverized using a pestle and a mortar. 20 mg of each of the pulverized organs was placed in a new tube, and the organ was lysed using a lysis buffer to obtain DNA. The concentration of the DNA was measured using a Nanodrop spectrometer, 100 ng of DNA was extracted using a QIAamp DNA blood mini kit (Qiagen), and real-time quantitative polymerase chain reaction (PCR) was performed to measure the number of viral genomes in each sample. The number of viral genomes in each sample was quantitatively verified for the distribution of liver cancer-specific oncolytic adenovirus.

Figure 35:
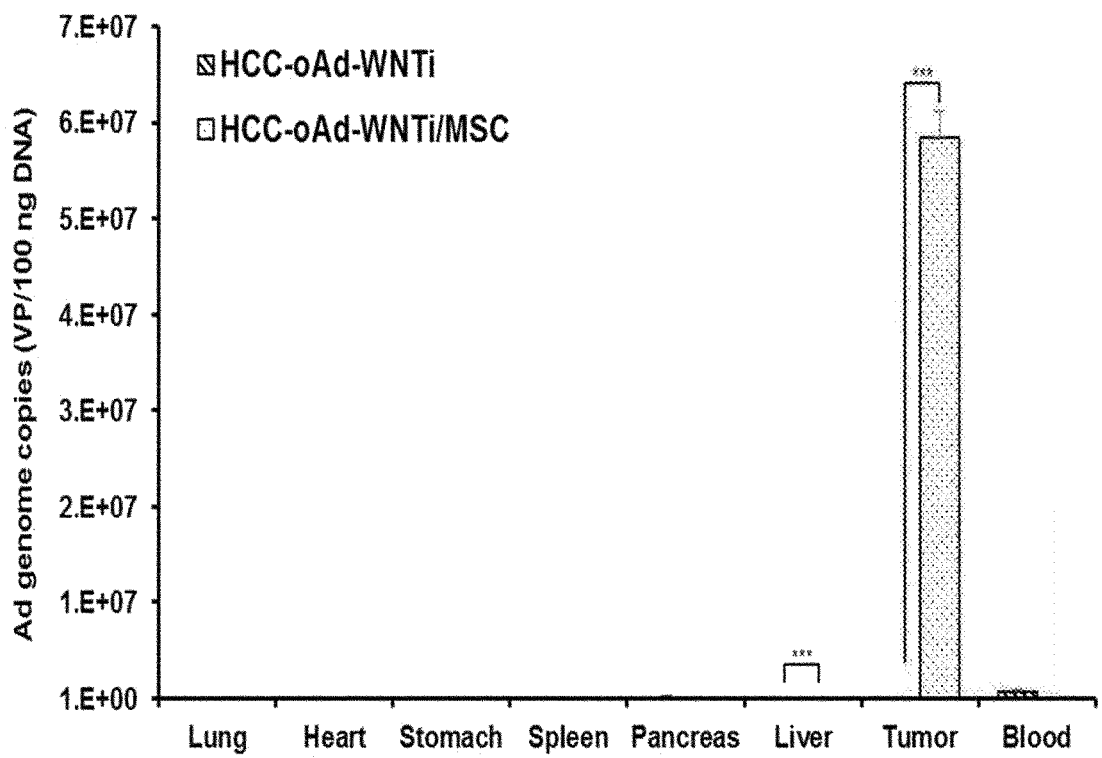
FIG. 35 is a graph showing the results of confirming the biodistribution of mesenchymal stem cells in which a liver cancer-targeting oncolytic adenovirus constructed according to an embodiment of the present invention is loaded, when systemically administered.

As illustrated in FIG. 35, HCC-oAd-WNTi/MSC absorbed into the liver exhibited a significant decrease (P<0.001) compared to naked HCC-oAd-WNTi. In addition, it is important that HCC-oAd-WNTi/MSC exhibits 4,824.2-fold greater intratumoral accumulation (P<0.001) than that of naked HCC-oAd-WNTi. These results demonstrate that MSCs can effectively protect oAd during systemic circulation, and reduces hepatic tropism of oAd, thereby inducing efficient intratumoral accumulation of the virus due to the tumor-targeting characteristic of MSCs. In addition, this data suggests that the intratumoral distribution of MSC-mediated oAd allows, even at a low dose of the virus, viral replication both in MSCs and tumor tissue while systemically circulating, thereby inducing a potent antitumor effect. Consequently, the tumor-to-liver ratio of HCC-oAd-WNTi/MSC was 6,480.8-fold greater than that of naked HCC-oAd-WNTi, which demonstrates that MSC-mediated oncolytic Ad delivery can overcome obstacles in systemic administration for enhancing the therapeutic efficiency of the virus and safety profiles, thus enhancing the effects.

Experimental Example 2-14

Observation of in Vivo Liver Cancer Histological Changes by HCC-Targeting Oncolytic Ad-MSC The tumor therapeutic effect of Ad-MSC in a liver cancer orthotopic xenograft model was histologically examined. MSCs were infected with 5 MOI of Ha$_2$bm-d19-k35/sLRP6 (HCC-oAd-WNTi) as oAd-MSC, which is a liver cancer-specific oncolytic adenovirus, for 24 hours.

Liver cancer cells were transplanted into a liver cancer orthotopic model (nude mice) and after 9 days and 13 days, $1\times10^6$ MSCs were administered to the liver cancer orthotopic model (nude mice) via the tail vein (Ad-MSC-treated group; HCC-oAd-WNTi/MSC). As controls, PBS (PBS-treated group), the same dose ($1\times10^6$ cells) of MSCs not infected with the virus, or the same dose ($5\times10^8$ VP) of Ad not loaded in MSCs (Ad-treated group; HCC-oAd-WNTi) was administered via the tail vein (n=6 mice/group).

3 days after the last administration, liver tissues were acquired from the four groups of mice, i.e., PBS-, MSC-, Ad-, and Ad-MSC-treated groups. The liver tissues were fixed in 10% formalin, embedded in paraffin, and cut into 5-μm sections. The sections were attached to slides and sequentially immersed in xylene and a 100%, 95%, 80%, or 70% ethanol solution to be deparaffinized, followed by hematoxylin and eosin (H&E) staining and Masson's trichrome staining for staining collagen fibrils. Next, the same tissues were subjected to immunohistochemistry staining using antibodies against CD90, which is a marker for human MSCs, and proliferating cell nuclear antigen (PCNA) for confirming the degree of cell proliferation. The tissue slides were sequentially immersed in xylene and a 100%, 95%, 80%, or 70% ethanol solution to be deparaffinized, and immersed in a 0.5% NP40 solution to enhance tissue permeability, and then allowed to react with a CD90 antibody (Abcam, Ltd., Cambridge, UK) or a PCNA antibody (DAKO, Glostrup, Denmark) at 4° C. overnight. The next day, a secondary antibody reaction was performed using an ABC-peroxidase kit (ChemMate DAKO Envision kit; DAKO, Carpinteria, CA), followed by hematoxylin staining, mounting with a mounting solution, and observation with a tissue microscope.

Figure 36:
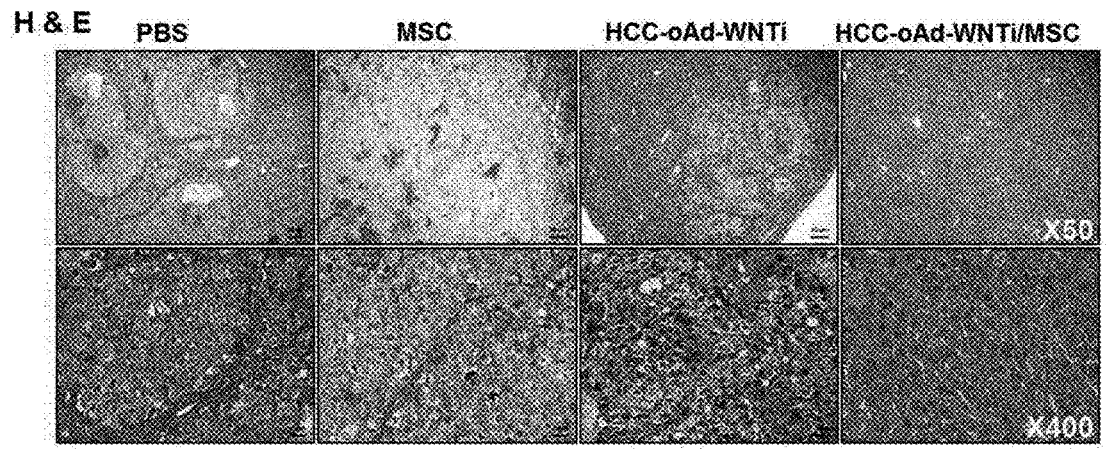
FIG. 36 is a set of images confirming liver cancer histological changes of stem cells in which liver cancer-specific oncolytic adenoviruses constructed according to an embodiment of the present invention are loaded.

As illustrated in FIG. 36, it was confirmed that a wide range of tumor distribution in liver tissue was confirmed in a control (PBS) or a group treated with MSCs or Ad, and the wide distribution of collagen fibers (stained in blue), which is a major component of the extracellular matrix and aid in the formation and growth of tumor tissue, was confirmed in cancer tissue boundary regions and cancer tissues, whereas no tumor tissue and collagen fiber were confirmed in the group administered Ad-MSC (HCC-oAd-WNTi/MSC) and a normal form of liver tissue was maintained.

Figure 37:
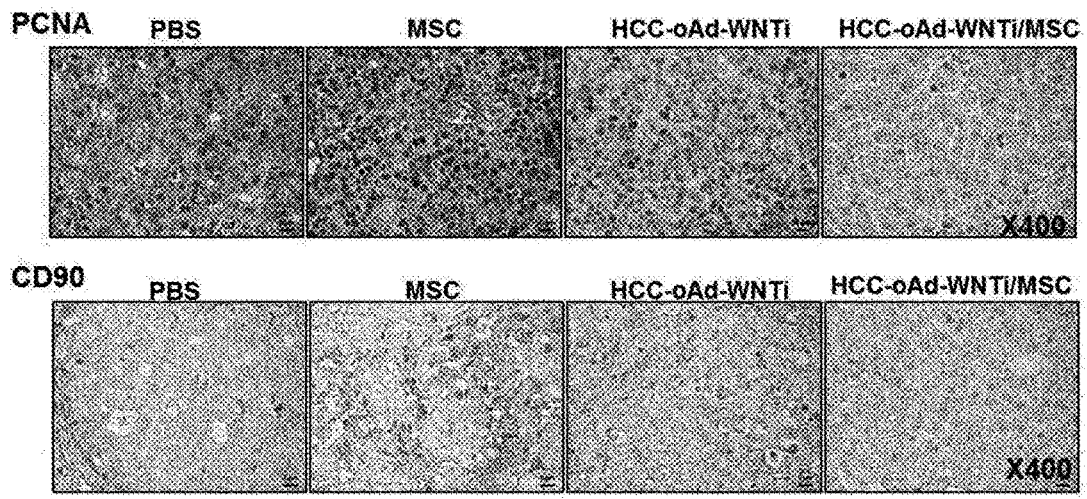
FIG. 37 is a set of images confirming liver cancer histological changes of stem cells in which liver cancer-specific oncolytic adenoviruses constructed according to an embodiment of the present invention are loaded.

In addition, as illustrated in FIG. 37, as a result of confirming the presence of MSCs through staining with CD90, which is an MSC marker, CD90 was positive in the liver tissues of mice treated with MSCs, and CD90 was negative in the liver tissues of mice treated with HCC-oAd-WNTi or HCC-oAd-WNTi/MSC. The result that MSCs remain in liver tissue for a long period of time only in the group administered MSCs alone indicates that MSCs having completed gene delivery are completely removed by Ad loaded therein, and considering that this means the exclusion of the possibility of causing side effects due to the remaining MSCs, the Ad-MSC of the present invention may have excellent characteristics as a therapeutic agent.

Next, as a result of confirming the degree of cell proliferation, excessive cancer cell-specific cell proliferation was confirmed only in a control (PBS) and the group administered MSCs or Ad, whereas no tumor cell was observed in a group administered the Ad-MSC of the present invention. It was confirmed that, compared to PBS, MSCs, or HCC-oAd-WNTi treatment, HCC-oAd-WNTi/MSC treatment significantly reduced the level of proliferating cells, and can effectively inhibit the proliferation of HCC tumors, thereby inducing a potent antitumor effect.

Experimental Example 2-15

Confirmation of Enhanced Pharmacokinetic Profile of HCC-oAd-WNTi/MSC

To effectively treat HCC tumors through a systemic administration method, the blood retention time of oAd needs to be extended for oAd delivery to target tumor tissue. Thus, in the present invention, it was evaluated whether to extend the blood retention time of HCC-targeting oAd-MSC.

To evaluate the rate at which Ad is removed from the blood of mice, real-time quantitative PCR (Q-PCR) was performed using whole blood samples of oAd-treated mice. $5 \times 10^8$ VP of naked HCC-oAd-WNTi or the same dose of HCC-oAd-WNTi/MSC (a total number of Ads loaded in MSCs is $5 \times 10^8$ VP) was systemically injected, and then 100 μL of whole blood was collected from the retro-orbital plexus of each mouse at 5 min, 10 min, 30 min, 1 h, 6 h, 24 h, or 48 h (n=3). Total DNA was extracted from whole blood aliquots using a QIAamp DNA blood mini kit (Qiagen, Hilden, Germany). The number of Ad genomes was measured by Q-PCR (Applied Biosystems). The samples were analyzed three times, and the experimental results were processed with the SDS 19.1 Software Package (Applied Biosystems).

Naked HCC-oAd-WNTi (Ad not loaded in MSCs) was rapidly removed from the blood. In contrast, HCC-oAd-WNTi/MSC was retained at 12-fold and 3,200-fold higher levels (P<0.001) in the blood at 1 hour and 24 hours, respectively, after injection, compared to naked HCC-oAd-WNTi, suggesting that MSCs effectively protect HCC-oAd-WNTi during systemic circulation.

The invention claimed is:

1. A mesenchymal stem cell (MSC) for treating cancer comprising a recombinant adenovirus comprising a target gene and the nucleic acid sequence set forth in SEQ ID NO: 1,
wherein the MSC is infected for 50 hours or less with the recombinant adenovirus at a concentration of greater than 0.01 MOI to less than 100 MOI.

2. The MCS for treating cancer of claim 1, wherein the recombinant adenovirus further comprises a gene expression regulatory sequence that regulates the expression of the target gene.

3. The MCS for treating cancer of claim 2, wherein the gene expression regulatory sequence comprises the AFP promoter sequence set forth in SEQ ID NO: 5 or the TERT promoter sequence set forth in SEQ ID NO: 8.

4. A composition for delivering a gene, the composition comprising a mesenchymal stem cell (MSC) in which a recombinant adenovirus comprising a target gene and the nucleic acid sequence set forth in SEQ ID NO: 1 is loaded,
wherein the MSC is infected for 50 hours or less with the recombinant adenovirus at a concentration of greater than 0.01 MOI to less than 100 MOI.

5. The composition of claim 4, wherein the recombinant adenovirus further comprises a gene expression regulatory sequence that regulates the expression of the target gene.

6. The composition of claim 4, wherein the composition is for systemic administration or local administration.

7. A pharmaceutical composition for treating cancer comprising a pharmaceutically effective amount of a mesenchymal stem cell (MSC) in which a recombinant adenovirus comprising a target gene and the nucleic acid sequence set forth in SEQ ID NO: 1 is loaded,
wherein the MSC is infected for 50 hours or less with the recombinant adenovirus at a concentration of greater than 0.01 MOI to less than 100 MOI.

8. The pharmaceutical composition of claim 7, wherein the recombinant adenovirus further comprises a gene expression regulatory sequence that regulates the expression of the target gene.

* * * * *